United States Patent
Castro Pineiro et al.

(10) Patent No.: US 9,139,594 B2
(45) Date of Patent: Sep. 22, 2015

(54) FUSED AMINODIHYDROPYRIMIDONE DERIVATIVES

(75) Inventors: Jose Luis Castro Pineiro, Hatfield (GB); Adrian Hall, Hatfield (GB); Andrew Madin, Hatfield (GB); Ngoc-Tri Vo, Hatfield (GB)

(73) Assignee: Eisai R&D Management Co., Ltd., Tokyo (JP)

(*) Notice: Subject to any disclaimer, the term of this patent is extended or adjusted under 35 U.S.C. 154(b) by 219 days.

(21) Appl. No.: 13/386,199

(22) PCT Filed: Jul. 21, 2010

(86) PCT No.: PCT/EP2010/060586
§ 371 (c)(1),
(2), (4) Date: Apr. 27, 2012

(87) PCT Pub. No.: WO2011/009897
PCT Pub. Date: Jan. 27, 2011

(65) Prior Publication Data
US 2012/0202828 A1    Aug. 9, 2012

(30) Foreign Application Priority Data
Jul. 22, 2009  (GB) .................... 0912777.0

(51) Int. Cl.
*A61K 31/519*    (2006.01)
*A61P 25/28*    (2006.01)
*C07D 491/048*    (2006.01)

(52) U.S. Cl.
CPC ................. *C07D 491/048* (2013.01)

(58) Field of Classification Search
None
See application file for complete search history.

(56) References Cited

U.S. PATENT DOCUMENTS

| | | |
|---|---|---|
| 3,227,713 A | 1/1966 | Behner et al. |
| 3,235,551 A | 2/1966 | Schubert et al. |
| 7,189,715 B2 | 3/2007 | Jerussi et al. |
| 7,648,983 B2 | 1/2010 | Audia et al. |
| 8,158,620 B2 | 4/2012 | Suzuki et al. |
| 8,198,269 B2 | 6/2012 | Motoki et al. |
| 8,338,407 B2 | 12/2012 | Hall et al. |
| 8,426,584 B2 | 4/2013 | Mitasev et al. |
| 8,501,733 B2 | 8/2013 | Motoki et al. |
| 2004/0110743 A1 | 6/2004 | Miyamato et al. |
| 2006/0052406 A1 | 3/2006 | Fisher et al. |
| 2006/0111370 A1 | 5/2006 | Zhu et al. |
| 2007/0021454 A1 | 1/2007 | Coburn et al. |
| 2007/0287692 A1 | 12/2007 | Wu et al. |
| 2008/0139538 A1 | 6/2008 | McGaughey et al. |
| 2008/0200445 A1 | 8/2008 | Zhu et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2010/0317850 A1 | 12/2010 | Suzuki et al. |
| 2011/0009395 A1 | 1/2011 | Audia et al. |
| 2011/0152253 A1 | 6/2011 | Motoki et al. |
| 2011/0207723 A1 | 8/2011 | Motoki et al. |
| 2012/0094984 A1 | 4/2012 | Suzuki et al. |

(Continued)

FOREIGN PATENT DOCUMENTS

| | | |
|---|---|---|
| EP | 1 942 105 | 7/2008 |
| EP | 2 233 474 | 9/2010 |

(Continued)

OTHER PUBLICATIONS

Soderberg, http://chemwiki.ucdavis.edu/Organic_Chemistry/Organic_Chemistry_With_a_Biological_Emphasis/Chapter_13%3A_Reactions_with_stabilized_carbanion_intermediates_I/Section_13.1%3A_Tautomers.*
Patani, Bioisosterism: A Rational Approach in Drug Design, Chem. Rev. 1996, 96, pp. 3147-3176.*
Dorwald, F.A., Side Reactions in Organic Synthesis, 2005, Wiley: VCH, Weinheim, p. IX.*
Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).
Ames et al., "Methods for detecting carcinogens and mutagens with the *Salmonella*/mammalian-microsome mutagenicity test," *Mutat. Res.*, 31:347-364 (1975).

(Continued)

*Primary Examiner* — San-Ming Hui
*Assistant Examiner* — Andrew Lee
(74) *Attorney, Agent, or Firm* — Fish & Richardson P.C.

(57) ABSTRACT

A compound represented by the general formula (I) or a pharmaceutically acceptable salt thereof or a solvate thereof, wherein Ring A is a $C_{6-14}$ aryl group or the like, L is —$NR^eCO$— or the like (wherein $R^e$ is a hydrogen atom or the like), Ring B is a $C_{6-14}$ aryl group or the like, X is a $C_{1-3}$ alkylene group or the like, Y is a single bond or the like, Z is a $C_{1-3}$ alkylene group or the like, $R^1$, $R^2$ and $R^x$ are each independently a hydrogen atom or the like, and $R^3$, $R^4$, $R^5$ and $R^6$ are independently a hydrogen atom, a halogen atom or the like, has an Aβ production inhibitory effect or a BACE1 inhibitory effect and is useful as a prophylactic or therapeutic agent for a neurodegenerative disease caused by Aβ and typified by Alzheimer-type dementia.

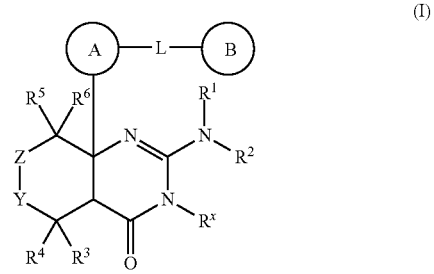

(I)

12 Claims, No Drawings

(56) References Cited

U.S. PATENT DOCUMENTS

| | | |
|---|---|---|
| 2012/0190672 A1 | 7/2012 | Hall et al. |
| 2012/0190848 A1 | 7/2012 | Mitasev et al. |
| 2012/0202804 A1 | 8/2012 | Ellard et al. |
| 2013/0197244 A1 | 8/2013 | Mitasev et al. |
| 2013/0203740 A1 | 8/2013 | Hall et al. |

FOREIGN PATENT DOCUMENTS

| | | |
|---|---|---|
| JP | 09-067355 | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | 2005/058311 | 6/2005 |
| WO | WO 2005/097767 | 10/2005 |
| WO | 2006/041404 | 4/2006 |
| WO | WO 2006/041405 | 4/2006 |
| WO | WO 2006/059234 | 6/2006 |
| WO | 2006/138264 | 12/2006 |
| WO | WO 2006138264 A2 * | 12/2006 |
| WO | WO 2007/011810 | 1/2007 |
| WO | WO 2007/049532 | 5/2007 |
| WO | 2007/114771 | 10/2007 |
| WO | WO 2007/139230 | 12/2007 |
| WO | 2008/073365 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2010/013302 | 2/2010 |
| WO | WO 2010/013794 | 2/2010 |
| WO | WO 2010/038686 | 4/2010 |
| WO | WO 2011/005738 | 1/2011 |
| WO | WO 2011/009897 | 1/2011 |
| WO | WO 2011/009898 | 1/2011 |
| WO | WO 2012/003274 | 1/2012 |
| WO | WO 2012/093148 | 7/2012 |
| WO | WO 2012/098461 | 7/2012 |
| WO | WO 2012/100179 | 7/2012 |

OTHER PUBLICATIONS

Aranyos et al., "Novel Electron-Rich Bulky Phosphine Ligands Facilitate the Palladium-Catalyzed Preparation of Diaryl Ethers," *J Am Chem Soc.*, 121(18):4369-4378 (1999).

Arnone et al., An Enantiospecific Entry to Fluoro Substituted Aminocyclopentanols through Intramolecular Nitrile Oxide, Nitrone, and Oxime Cycloaddition Reactions, *Tetrahedron: Asymmetry* 5(6):1019-1028 (1994).

Aschwanden et al., "Reduction of 2,3-dihydroisoxazoles to beta-amino ketones and beta-amino alcohols," *Org. Lett.*, 7(25):5741-5742 (2005).

Barange et al., "A Remarkable Accelerating Effect of Ag-Salt on Intramolecular Cyclization of o-(1-Alkynyl)benzenesulfonamides," *J. Org. Chem.*, 72(22):8547-8550 (2007).

Barlow et al., "Intervalence Transitions in the Mixed-Valence Monocations of Bis(triarylamines) Linked with Vinylene and Phenylene—Vinylene Bridges," *J. Am. Chem. Soc.*, 127(48):16900-16911 (2005).

Berge et al., "Pharmaceutical salts," *J. Pharm. Sci.*, 66:1-19 (1977).

Bobrov et al., "Interaction of Quinone Oxide with Thiourea" *Chemistry and Chemical Technology*, 33(10):15-18 (1990) (original and English language translation).

Brzostwska et al., "Chiral Prodyes: Synthesis and Full Characterization of (S)-1-Phenylethylamides of the Optically Active Q-Methyldihydrofluoresceins," *Heterocycles*, 32(10):1968-1972 (1991).

Chakrabarty et al., "DBU, a highly efficient reagent for the facile regeneration of (hetero)arylamines from their acetamides and benzamides: influence of solvent, temperature, and microwave irradiation," *Synth. Commun.*, 32(2):265-272 (2002).

Coates et al., "Annelative ring expansion via intramolecular [2+2] photocycloaddition of .alpha.,.beta.-unsaturated .gamma.-lactones and reductive cleavage: synthesis of hydrocyclopentacyclooctene-5-carboxylates," *J. Org. Chem.*, 47(19):3597-3607 (1982).

Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).

Crisp and Meyer, "Palladium-catalyzed, carbonylative, intramolecular coupling of hydroxyvinyl triflates. Synthesis of substituted .alpha.,.beta.-butenolides," *J. Org. Chem.*, 57(25):6972-6975 (1992).

Cross et al., International Union of Pure and Applied Chemistry (IUPAC) Rules for the Nomenclature of Organic Chemistry, Section E, Stereochemistry, *Pure & Applied Chemistry*, 45:11-30 (1976).

Danheiser et al., "An annulation method for the synthesis of highly substituted polycyclic aromatic and heteroaromatic compounds," *J Am. Chem. Soc.*, 112(8):3093-3100 (1990).

De Lucca et al., "Discovery and Structure—Activity Relationship of N-(Ureidoalkyl)-Benzyl-Piperidines as Potent Small Molecule CC Chemokine Receptor-3 (CCR3) Antagonists," *J. Med. Chem.*, 45(17)3794-3804 (2002).

Edwards et al., "Application of Fragment-Based Lead Generation to the Discovery of Novel, Cyclic Amidine β-Secretase Inhibitors with Nanomolar Potency, Cellular Activity, and High Ligand Efficiency," *J. Med. Chem.*, 50(24):5912-5925 (2007).

Fang et al., "Synthesis, Antibacterial, and Cytotoxic Evaluation of Certain 7-Substituted Norfloxacin Derivatives," *J. Med. Chem.*, 43(20):3809-3812 (2000).

Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).

Fuller et al., "Succinct Synthesis of β-Amino Acids via Chiral Isoxazolin," *J. Am. Chem. Soc.*, 127(15):5376-5383 (2005).

Fuller et al., "Synthesis and Structural Characteristics of Geminally Disubstituted β-Amino Acids," *SYNLETT.*, 8:1409-1413 (2004).

Fulop et al., "Synthesis of Stereoisomers 2-Phenylimino-3, 1-Perhydro-Benzoxazines and 3, 1-Perhydrobenzothiazines," *Org Prep Proced Int'l*, 20:73-82 (1988).

Glenner et al., "Alzheimer's Disease: Initial report of the purification and characterization of a novel cerebrovascular amyloid protein," *Biochemical and Biophysical Research Communications*, 120(3):885-890 (1984).

Gloor et al., "Molecular and cellular permeability control at the blood-brain barrier," *Brain Res. Rev.*, 36:258-264 (2001).

Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).

Gouras et al., "Intraneuronal Aβ42 Accumulation in Human Brain," *American Journal of Pathology*, 156(1):15-20 (2000).

Green et al., "Mutagen testing using TRP+ reversion in *Escherichia coli*," *Mutat. Res.*, 38:3-32 (1976).

Greene and Wuts, "Protective Groups in Organic Chemistry, Second Edition", *John Wiley & Sons* p. 327-330 (1991).

Greene and Wuts, "Protective Groups in Organic Chemistry, Third Edition", *John Wiley & Sons*, p. 17-245 (1999).

Greene and Wuts, "Protective Groups in Organic Chemistry, Third Edition", *John Wiley & Sons*, p. 506-507 (1999).

Greene and Wuts, "Protective Groups in Organic Chemistry, Third Edition", *John Wiley & Sons*, p. 293-329 (1999).

Greene and Wuts, "Protective Groups in Organic Chemistry, Third Edition", *John Wiley & Sons*, p. 494-572 (1999).

Greene and Wuts, "Protective Groups in Organic Chemistry, Third Edition", *John Wiley & Sons*, p. 531-537 (1999).

Greene and Wuts, "Protective Groups in Organic Chemistry, Third Edition", *John Wiley & Sons*, p. 642-643 (1999).

Greene et al., "Protective Groups in Organic Chemistry, Third Edition," *John Wiley & Sons*, 404-408 (1999).

Greene et al., "Protective Groups in Organic Chemistry, Third Edition," *John Wiley & Sons*, 518-525 (1999).

(56) References Cited

OTHER PUBLICATIONS

Gu et al., "Facile One-Pot Synthesis of 6-Monosubstituted and 6,12-Disubstituted 5,11-Dihydroindolo[3,2-b]carbazoles and Preparation of Various Functionalized Derivatives," *J. Org. Chem.*, 72(19):7207-7213 (2007).
Hall et al., "Comparative pharmacokinetic-pharmacodynamic responses in rat and cynomolgus monkey for a novel BACE inhibitor ER-901356," *11th Int'l Conf on Alzheimer's & Parkinson's Diseases (AD/PD 2013)*, 4 pages, (Mar. 6-10, 2013).
Han et al., "Diverse Synthesis of Novel Bisterpyridines via Suzuki-Type Cross-Coupling," *Org. Lett.*, 9(4):559-562 (2007).
Hassner et al. "Stereochemistry. 82. Conformation of fused five-membered heterocyclic rings derived from the intramolecular oxime olefin cycloaddition reaction," *J. Org. Chem.*, 58(17):4539-4546 (1993).
Hassner, "Interamolecular Oxime Olefin Cycloadditions. Stereospecific Formation of Functionalized Pyrrolidines," *Tetrahedron Letters*, 29 (41):5313-5316 (1988).
He et al., "Utility of unbound plasma drug levels and P-glycoprotein transport data in prediction of central nervous system exposure," *Xenobiotica*, 39:687-693 (2009).
Heany et al., "The influence of oxime stereochemistry in the generation of nitrones from omega-alkenyloximes by cyclization or 1,2-prototropy," *J. Chem. Soc., Perkin Trans.*, 1:341-349 (Jan. 1, 1998).
Hitchcock et al., "Structure-brain exposure relationships," *J. Med. Chem.*, 49:7559-7583 (2006).
Hock et al., "Antibodies against β-Amyloid Slow Cognitive Decline in Alzheimer's Disease," *Neuron*, 38:547-554 (2003).
Howbert et al., "Novel agents effective against solid tumors: the diarylsulfonylureas. Synthesis, activities, and analysis of quantitative structure-activity relationships," *J. Med. Chem.*, 33:2393-2407 (1990).
Hussain et al., "Oral administration of a potent and selective non-peptidic BACE-1 inhibitor decreases beta-cleavage of amyloid precursor protein and amyloid-beta production in vivo," *J. Neurochem.*, 100:802-809 (2007).
Iserloh et al., "Discovery of an orally efficaceous 4-phenoxypyrrolidine-based BACE-1 inhibitor," *Bioorg. Med. Chem. Lett.*, 18:418-422 (2008).
Ishikawa et al., "Synthesis of A-Ring Fragments of 1α,25-Dihydroxyvitamin $D_3$ and Taxane Diterpenoids: Effective Construction of Conjugated Formylcyclohexene Frameworks from Isoxazolines," *Tetrahedron*, 54(22):5869-5882 (1998).
Iwata et al., "Radiosynthesis of O-[$^{11}$C]methyl-L-tyrosine and O-[$^{18}$F]Fluoromethyl-L-tyrosine as potential PET tracers for imaging amino acid transport," *J Labelled Compounds & Radiopharmaceuticals*, 46(6):555-566 (2003).
Jarrett et al., "The Carboxy Terminus of the β Amyloid Protein is Critical for the Seeding of Amyloid Formation: Implications for the Pathogenesis of Alzheimer's Disease," *Biochemistry*, 32(18):4693-4697 (1993).
Ji et al., "Synthesis and Structure—Activity Relationship Studies of 3,6-Diazabicyclo[3.2.0]heptanes as Novel α4132 Nicotinic Acetylcholine Receptor Selective Agonists," *J. Med. Chem.*, 50(22):5493-5508 (2007).
Katagiri et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids," *Tetrahedron*, 53(16):5725-5746 (1997).
Kearney et al., "Solid-Phase Synthesis of 2-Aminothiazoles," *J. Org. Chem.*, 63(1):196-200 (1998).
Knauer and Kunz, "Palladium-catalysed C—C coupling reactions in the enantioselective synthesis of 2,4-disubstituted 4,5-dehydropiperidines using galactosylamine as a stereodifferentiating auxiliary," *Tetrahedron: Asymmetry*, 16(2):529-539 (2005).
Kuo et al., "A Synthesis of Estrone via Novel Intermediates, Mechanism of the Coupling Reaction of a Vinyl Carbinol with a βDiketone," *Journal of Organic Chemistry*, 33(8):3126-3132 (1968).
Kusuhara et al., "Efflux transport systems for drugs at the blood-brain barrier and blood-cerebrospinal fluid barrier (Part 1)," *Drug Discov. Today*, 6:150-156 (2001).
Kwong et al., "Copper-Catalyzed Coupling of Alkylamines and Aryl Iodides: An Efficient System Even in an Air Atmosphere," *Org. Lett.*, 4(4):581-584 (2002).
Leroux et al., "Trifluoromethoxy Substituted Anilines: Metalation as the Key Step for Structural Elaboration," *J. Org. Chem.*, 68(12):4693-4699 (2003).
Lin et al., "Role of P-glycoprotein in pharmacokinetics: clinical implications," *Clin. Pharmacokinet.*, 42:59-98 (2003).
Lin, "How significant is the role of P-glycoprotein in drug absorption and brain uptake?," *Drugs of Today*, 40:5-22 (2004).
Littke et al., "Versatile Catalysts for the Suzuki Cross-Coupling of Arylboronic Acids with Aryl and Vinyl Halides and Triflates under Mild Conditions," *J. Am. Chem. Soc.*, 122(17):4020-4028 (2000).
Liu et al., "A practical and chemoselective reduction of nitroarenes to anilines using activated iron," *Adv. Synth. Caral.*, 347:217-219 (2005).
Mahar et al., "Passive permeability and P-glycoprotein-mediated efflux differentiate central nervous system (CNS) and non-CNS marketed drugs," *J. Pharmacol. Exp. Ther.*, 303:1029-1037 (2002).
Malamas et al., "Design and synthesis of aminohydantoins as potent and selective human β-secretase (BACE1) inhibitors with enhanced brain permeability," *Bioorg. Med. Chem. Lett.*, 20:6597-6605 (2010).
Masters et al., "Amyloid plaque core protein in Alzheimer disease and Down syndrome," *Proceeding National Academy of Science USA*, 82:4245-4249 (1985).
Matassa et al., "Synthesis and in vitro LTD4 antagonist activity of bicyclic and monocyclic cyclopentylurethane and cyclopentylacetamide N-arylsulfonyl amides," *J. Med. Chem.*, 33(9):2621-2629 (1990).
Maurer, "Relationship between exposure and nonspecific binding of thirty-three central nervous system drugs in mice," *Drug Metab. Dispos.*, 33:175-181 (2005).
McCann et al., "Detection of carcinogens as mutagens in the *Salmonella*/microsome test: assay of 300 chemicals," *Proc. Natl. Acad. Sci. USA.*, 72:5135-5139 (1975).
McCann et al., "Detection of carcinogens as mutagens in the *Salmonella*/microsome test: assay of 300 chemicals: discussion," *Proc. Natl. Acad. Sci. USA*, 73:950-954 (1976).
Meredith et al., "P-Glycoprotein Efflux and Other Factors Limit Brain Amyloid βReduction by β-Site Amyloid Precursor Protein-Cleaving Enzyme 1 Inhibitors in Mice," *J. Pharmacol. Exp. Ther*, 326(2):502-513 (2008).
Nahm et al., N-Methoxy-N-Methylamides as Effective Acylating Agents, *Tetrahedron Lett.*, 22(39):3815-3818 (1981).
Nerdinger et al., "Combined Directed ortho Metalation/Suzuki—Miyaura Cross-Coupling Strategies. Regiospecific Synthesis of Chlorodihydroxybiphenyls and Polychlorinated Biphenyls," *J. Org. Chem.*, 72(16):5960-5967 (2007).
Nussbaumer et al., "Highly selective TFAA-cleavage of tertiary 2,4-dimethoxybenzylamines and its use in the synthesis of secondary amines," *Tetrahedron*, 47(26):4591-4602 (1991).
Prakash et al., "Perfluoroalkylation with Organosilicon Reagents," *Chem. Rev.*, 97:757-786 (1997).
Quach and Batey, "Ligand- and Base-Free Copper(II)-Catalyzed C—N Bond Formation: Cross-Coupling Reactions of Organoboron Compounds with Aliphatic Amines and Anilines," *Org. Lett.*, 5(23):4397-4400 (2003).
Rao et al., "Improved Synthesis of Mirtazapine," *Org. Prep. Proced. Int.*, 39(4):399-402 (2007).
Rolandsgard et al., "Stereoselective preparation of spirane bridged, sandwiched bisarenes," *Tetrahedron*, 61(16):4128-4140 (2005).
Romero et al., "Discovery, synthesis, and bioactivity of bis(heteroaryl)piperazines. 1. A novel class of non-nucleoside HIV-1 reverse transcriptase inhibitors," *J. Med. Chem.*, 37(7):999-1014 (1994).
Rosowsky et al., "Synthesis and biological activity of the 2-desamino and 2-desamino-2-methyl analogues of aminopterin and methotrexate," *J. Med. Chem.*, 34(1):227-234 (1991).
Sankaranarayanan et al., "First demonstration of cerebrospinal fluid and plasma A beta lowering with oral administration of a beta-site

(56) References Cited

OTHER PUBLICATIONS amyloid precursor protein-cleaving enzyme 1 inhibitor in nonhuman primates," *J. Pharmacol. Exp. Ther.*, 328:131-140 (2009).
Sankaranarayanan et al., "In Vivo β-Secretase 1 Inhibition Leads to Brain Aβ Lowering and Increased α-Secretase Processing of Amyloid Precursor Protein without Effect on Neuregulin-1," *J. Pharmacol. Exp. Ther*, 324(3):957-969 (2008).
Sapountzis et al., "Synthesis of Functionalized Nitroarylmagnesium Halides via an Iodine—Magnesium Exchange," *J. Org. Chem.*, 70(7):2445-2454 (2005).
Scheuner et al., "Secreted amyloid β-protein similar to that in the senile plaques of Alzheimer's disease is increased in vivo by the presenilin 1 and 2 and APP mutations linked to familial Alzheimer's disease," *Nature Medicine*, 2(8):864-870 (1996).
Schinkel, "P-Glycoprotein, a gatekeeper in the blood-brain barrier," *Adv. Drug Deliv. Rev.*, 36:179-194 (1999).
Schwizer et al., "Antagonists of the myelin-associated glycoprotein: A new class of tetrasaccharide mimics," *Bioorg. Med. Chem.*, 14:4944-4957 (2006).
Selles and Mueller, "Expedient Synthesis of Highly Substituted Fused Heterocoumarins," *Org. Lett.*, 6(2):277-279 (2004).
Shao et al., "4-(2-Pyridyl)piperazine-1-benzimidazoles as potent TRPV1 antagonists," *Bioorg. Med. Chem. Lett.*, 15(3):719-723 (2005).
Shing et al., "Intramolecular nitrile oxide-alkene cycloaddition of sugar derivatives with unmasked hydroxyl group(s)," *Org. Lett.*, 9(5):753-756 (2007).
Summerfield et al., "Central nervous system drug disposition: the relationship between in situ brain permeability and brain free fraction," *J. Pharmacol. Exp. Ther.*, 322:205-213 (2007).
Tamayo et al., Design and synthesis of potent pyridazine inhibitors of p38 MAP kinase, *Bioorg. Med. Chem. Lett.*,15(9):2409-2413 (2005).
Tao et al., "Copper-catalyzed synthesis of aryl azides and 1-aryl-1,2,3-triazoles from boronic acids," *Tetrahedron Lett.*, 48:3525-3529 (2007).
Trainor, "The importance of plasma protein binding in drug discovery," *Expert Opin. Drug Discov.*, 2:51-64 (2007).
Tzschucke et al., "Arenes to Anilines and Aryl Ethers by Sequential Iridium-Catalyzed Borylation and Copper-Catalyzed Coupling," *Org. Lett.*, 9(5):761-764 (2007).
Tzvetkov et al., Synthesis and photoinitiated radical cyclization of allyl- and propynyloxymethyl substituted cyclopentanones to tetrahydrocyclopenta[c]furanols, *Tetrahedron Lett.*, 46(45):7751-7755 (2005).
Ueno, "Molecular anatomy of the brain endothelial barrier: an overview of the distributional features," *Curr. Med. Chem.*, 14:1199-1206 (2007).
Uno et al., "Reaction of 2-Isoxazolines with Organolithiums in the Presence of Boron Trifluoride," *Bull. Chem. Soc. Jpn.*, 66:2730-2737 (1993).
Vedejs et al., "Enantiocontrolled Synthesis of (1S,2S)-6-Desmethyl-(methylaziridino)mitosene," *J. Am. Chem. Soc.*, 122(22):5401-5402 (2000).
Vedejs et al., "Synthetic Enantiopure Aziridinomitosenes: Preparation, Reactivity, and DNA Alkylation Studies," *J. Am. Chem. Soc.*, 125(51):15796-15806 (2003).
Watanabe et al., "A convenient method for the synthesis of Δ1,6-bicyclo[4.n.0]alken-2-ones," *Tetrahedron Lett.*, 40(46):8133-8136 (1999).
Whisler et al., "Synthetic applications of lithiated N-Boc allylic amines as asymmetric homoenolate equivalents," *J. Org. Chem.*, 68:1207-1215 (2003).
Amended Claims Filed in response to Communication from European Application No. 10734143.0-2101, 8 pages (Sep. 5, 2012).
Office Action from European Application No. 10734143.0-1452, 5 pages (May 13, 2013).
Search Report for International Patent Application PCT/EP2010/060586 dated Sep. 29, 2010.
Written Opinion for International Patent Application PCT/EP2010/060586 dated Sep. 29, 2010.

\* cited by examiner

FUSED AMINODIHYDROPYRIMIDONE DERIVATIVES

FIELD OF THE INVENTION

The present invention relates to a fused aminodihydropyrimidone derivative and pharmaceutical use thereof. More particularly, the present invention relates to a fused aminodihydropyrimidone derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydropyrimidone derivative as an active ingredient.

DESCRIPTION OF RELATED ART

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia. Aβ-proteins have, as main components, Aβ40 consisting of 40 amino acids and Aβ42 with two amino acids added at the C-terminal. The Aβ40 and Aβ42 are known to have high aggregability and to be main components of senile plaques. Further, it is known that the Aβ40 and Aβ42 are increased by mutation in APP and presenilin genes which is observed in familial Alzheimer's disease. Accordingly, a compound that reduces production of Aβ40 and Aβ42 is expected to be a progression inhibitor or prophylactic agent for Alzheimer's disease.

Aβ is produced by the cleavage APP by beta-secretase (BACE1) and subsequently by gamma-secretase. For this reason, attempts have been made to create gamma-secretase and beta-secretase inhibitors in order to inhibit Aβ production. Already known beta-secretase inhibitors are reported in Patent Documents 1 to 6 shown below and the like and Non-Patent Document 1.

[Patent Document 1] WO2007/114771 (AstraZeneca AB & Astex Therapeutics Ltd)
[Patent Document 2] WO2006/041404 (AstraZeneca AB & Astex Therapeutics Ltd)
[Patent Document 3] WO2005/058311 (Schering-Plough Corporation)
[Patent Document 4] US2006111370 (Schering-Plough Corporation)
[Patent Document 5] US2007287692 (Schering-Plough Corporation)
[Patent Document 6] US2008200445 (Schering-Plough Corporation)
[Non-Patent Document 1] J. Med. Chem 2007, 50, 5912

In particular, Patent Document 1 describes 2-aminopyrimidin-4-ones of the following formula:

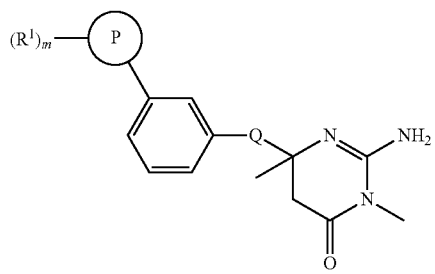

and their use for treating or preventing Aβ-related pathologies, e.g. Alzheimer's Disease.

Patent Document 2 describes substituted amino-compounds and their use in the treatment of Aβ-related pathologies, e.g. Alzheimer's Disease. Patent Documents 3 to describe aspartyl protease inhibitors and their use in the treatment of e.g. Alzheimer's Disease.

BRIEF SUMMARY OF THE INVENTION

An object of the present invention is to provide a fused aminodihydropyrimidone compound which has an Aβ production inhibitory effect or a BACE1 inhibitory effect and is useful as a prophylactic or therapeutic agent for a neurodegenerative disease caused by Aβ and typified by Alzheimer-type dementia, and pharmaceutical use thereof.

The present invention relates to:
[1] A compound represented by the formula (I):

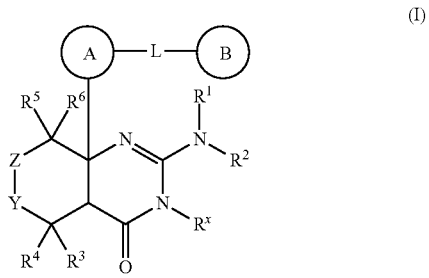

or a pharmaceutically acceptable salt thereof or a solvate thereof, wherein

Ring A is a $C_{6-14}$ aryl group which optionally has 1 to 3 substituents selected from Substituent Group α, a 5- to 6-membered heteroaryl group which optionally has 1 to 3 substituents selected from Substituent Group α or a 9- to 10-membered benzo-fused heterocyclic group which optionally has 1 to 3 substituents selected from Substituent Group α;

L is a single bond, an oxygen atom, a formula —NR$^e$CO— (wherein R$^e$ is a hydrogen atom or a $C_{1-6}$ alkyl group which optionally has 1 to 3 substituents selected from Substituent Group α), a formula —NR$^e$SO$_2$— (wherein R$^e$ is a hydrogen atom or a $C_{1-6}$ alkyl group which optionally has 1 to 3 substituents selected from Substituent Group α), a formula —NR$^e$— (wherein R$^e$ is a hydrogen atom or a $C_{1-6}$ alkyl group which optionally has 1 to 3 substituents selected from Substituent Group α), a $C_{1-6}$ alkylene group which optionally has 1 to 3 substituents selected from Substituent Group α, a $C_{2-6}$ alkenylene group which optionally has 1 to 3 substituents selected from Substituent Group α or a $C_{2-6}$ alkynylene group which optionally has 1 to 3 substituents selected from Substituent Group α;

Ring B is a $C_{3-8}$ cycloalkyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α;

Y is a single bond, —$NR^Y$— (wherein $R^Y$ is a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α), an oxygen atom, a sulfur atom, a sulfoxide or a sulfone;

Z is a single bond, a $C_{1-3}$ alkylene group which optionally has 1 to 3 substituents selected from Substituent Group α or a $C_{2-3}$ alkenylene group which may have 1 to 3 substituents selected from Substituent Group α;

$R^1$ and $R^2$ are each independently a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; and $R^3$, $R^4$, $R^5$ and $R^6$ are independently a hydrogen atom, a halogen atom, a hydroxy group, a $C_{1-6}$ alkyl group which optionally has 1 to 3 substituents selected from Substituent Group α, a $C_{1-6}$ alkoxy group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; or $R^4$ and $R^6$ together form a ring represented by the formula (II):

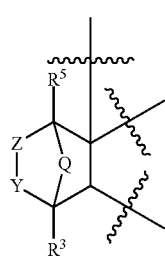

wherein Y, Z, $R^5$ and $R^3$ are the same as defined above and Q is an oxygen atom, a methylene group or an ethylene group;

$R^x$ is a hydrogen atom, a $C_{1-6}$ alkyl group which optionally has 1 to 3 substituents selected from Substituent Group α, a $C_{3-8}$ cycloalkyl group which optionally has 1 to 3 substituents selected from Substituent Group α, a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl-$C_{1-6}$ alkyl group which optionally has 1 to 3 substituents selected from Substituent Group α, a $C_{6-14}$ aryl-$C_{1-6}$ alkyl group which optionally has 1 to 3 substituents selected from Substituent Group α, a 5- to 10-membered heterocyclic-$C_{1-6}$ alkyl group which optionally has 1 to 3 substituents selected from Substituent Group α,

[Substituent Group α: a hydrogen atom, a halogen atom, a hydroxy group, a nitro group, a $C_{1-6}$ alkylthio group, a $C_{6-14}$ aryl group, aryloxycarbonyl group, a $C_{6-14}$, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group is optionally substituted with a $C_{1-6}$ alkyl group), a $C_{2-6}$ alkenyl group which optionally has 1 to 3 substituents selected from Substituent Group β, a $C_{2-6}$ alkynyl group which optionally has 1 to 3 substituents selected from Substituent Group β, a carbamoyl group which is optionally substituted with one or two $C_{1-6}$ alkyl groups, a $C_{1-6}$ alkoxy group which optionally has 1 to 3 substituents selected from Substituent Group β, a $C_{1-6}$ alkyl group which optionally has 1 to 3 substituents selected from Substituent Group β and a 5- to 10-membered heterocyclic group which optionally has 1 to 3 substituents selected from Substituent Group β;

Substituent Group β: a halogen atom, a cyano group, a hydroxy group, a $C_{1-6}$ alkoxy group, a $C_{1-6}$ alkyl group, a $C_{3-8}$ cycloalkyl group and an oxo group];

[2] The compound or pharmaceutically acceptable salt thereof or solvate thereof according to [1] above, wherein X is a methylene which optionally has 1 to 2 substituents selected from Substituent Group α;

[3] The compound or pharmaceutically acceptable salt thereof or solvate thereof according to [1] or [2] above, wherein Y is an oxygen atom;

[4] The compound or pharmaceutically acceptable salt thereof or solvate thereof according to any one of [1] to [3] above, wherein Z is a single bond;

[5] The compound or pharmaceutically acceptable salt thereof or solvate thereof according to any one of [1] to [4] above, wherein L is a single bond, a formula —$NR^eCO$— (wherein $R^e$ is a hydrogen atom or a $C_{1-6}$ alkyl group which optionally has 1 to 3 substituents selected from Substituent Group α) or a formula —$NR^eSO_2$— (wherein $R^e$ is a hydrogen atom or a $C_{1-6}$ alkyl group which optionally has 1 to 3 substituents selected from Substituent Group α);

[6] The compound or pharmaceutically acceptable salt thereof or solvate thereof according to [5] above, wherein L is a formula —$NR^eCO$— (wherein $R^e$ is a hydrogen atom or a $C_{1-6}$ alkyl group which optionally has 1 to 3 substituents selected from Substituent Group α);

[7] The compound or pharmaceutically acceptable salt thereof or solvate thereof according to any one of [1] to [6] above, wherein Ring A is a $C_{6-14}$ aryl group which optionally has 1 to 3 substituents selected from Substituent Group α;

[8] The compound or pharmaceutically acceptable salt thereof or solvate thereof according to any one of [1] to [6] above, wherein Ring B is a 5 to 10-membered heterocyclic group which optionally has 1 to 3 substituents selected from Substituent Group α;

[9] The compound or pharmaceutically acceptable salt thereof or solvate thereof according to any one of [1] to [8] above, wherein the compound is selected from:

N-(3-(2-amino-3-methyl-4-oxo-3,4,4a,5,7,7a-hexahydro-furo[3,4-d]pyrimidin-7a-yl)-4-fluorophenyl)-5-(difluoromethyl)pyrazine-2-carboxamide:

5

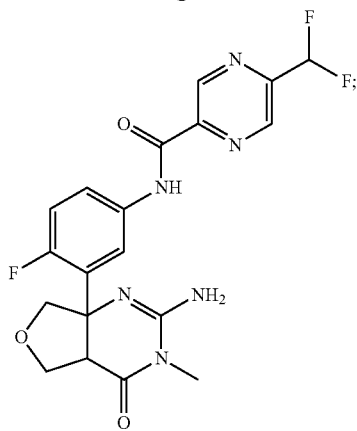

N-(3-(2-amino-3-methyl-4-oxo-3,4,4a,5,7,7a-hexahydro-furo[3,4-d]pyrimidin-7a-yl)-4-fluorophenyl)-5-methoxy-pyrazine-2-carboxamide:

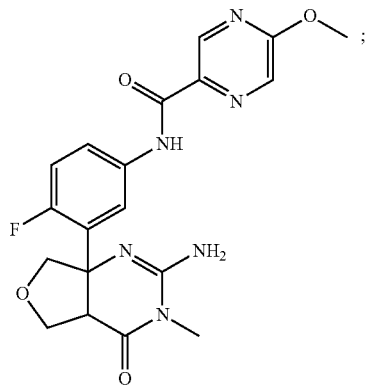 [SMILES: COc1cnc(C(=O)Nc2ccc(F)c(C34COCC3C(=O)N(C)C(N)=N4)c2)cn1]

N-(3-(2-amino-3-methyl-4-oxo-3,4,4a,5,7,7a-hexahydro-furo[3,4-d]pyrimidin-7a-yl)-4-fluorophenyl)-5-(difluoromethoxy)pyrazine-2-carboxamide:

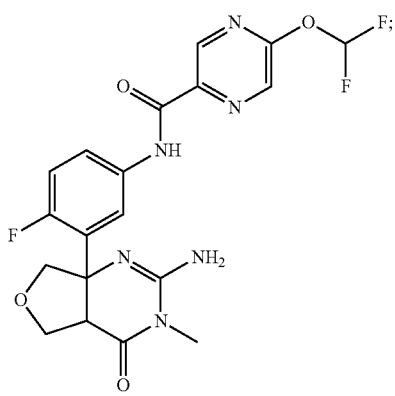

N-(3-(2-amino-3-methyl-4-oxo-3,4,4a,5,7,7a-hexahydro-furo[3,4-d]pyrimidin-7a-yl)-4-fluorophenyl)-5-(fluoromethoxy)pyrazine-2-carboxamide:

6

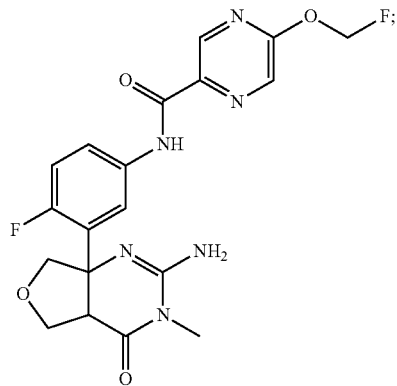

N-(3-(2-amino-3-methyl-4-oxo-3,4,4a,5,7,7a-hexahydro-furo[3,4-d]pyrimidin-7a-yl)-4-fluorophenyl)-5-ethoxy-pyrazine-2-carboxamide:

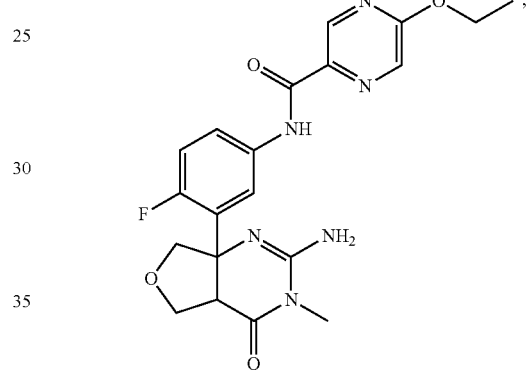

N-(3-(2-amino-3-methyl-4-oxo-3,4,4a,5,7,7a-hexahydro-furo[3,4-d]pyrimidin-7a-yl)-4-fluorophenyl)-5-fluoropicolinamide:

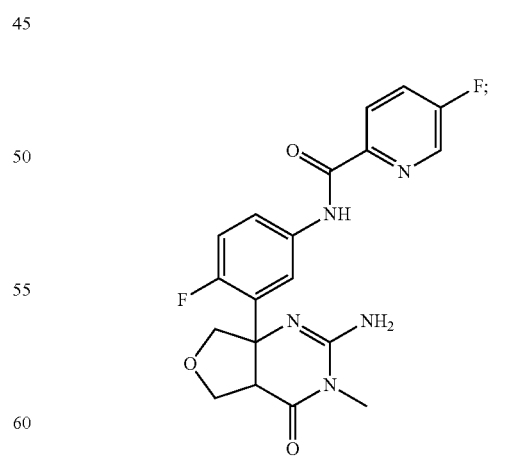

N-(3-(2-amino-3-methyl-4-oxo-3,4,4a,5,7,7a-hexahydro-furo[3,4-d]pyrimidin-7a-yl)-4-fluorophenyl)-5-cyanopicolinamide:

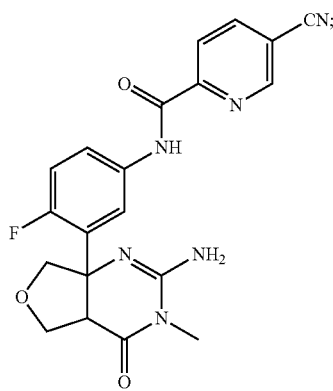

N-(3-(2-amino-3-methyl-4-oxo-3,4,4a,5,7,7a-hexahydro-furo[3,4-d]pyrimidin-7a-yl)-4-fluorophenyl)-5-chloropicolinamide:

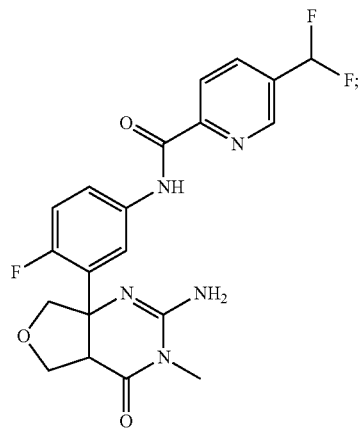

N-(3-(2-amino-3-methyl-4-oxo-3,4,4a,5,7,7a-hexahydro-furo[3,4-d]pyrimidin-7a-yl)-4-fluorophenyl)-5-(fluoromethyl)picolinamide:

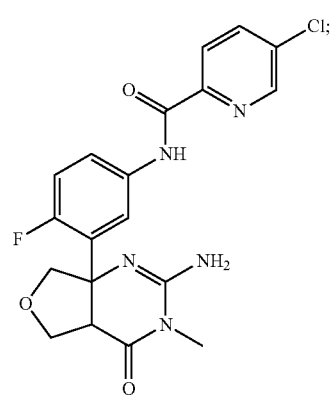 [SMILES: CN1C(=O)C2COCC2(c2cc(NC(=O)c3ccc(Cl)cn3)ccc2F)N=C1N]

N-(3-(2-amino-3-methyl-4-oxo-3,4,4a,5,7,7a-hexahydro-furo[3,4-d]pyrimidin-7a-yl)-4-fluorophenyl)-5-(trifluoromethyl)picolinamide:

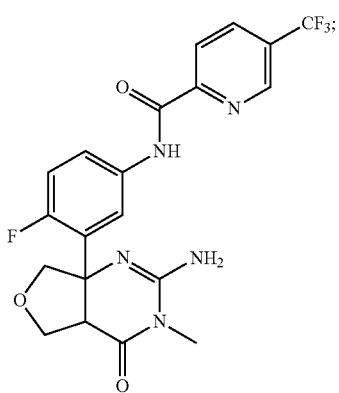

N-(3-(2-amino-3-methyl-4-oxo-3,4,4a,5,7,7a-hexahydro-furo[3,4-d]pyrimidin-7a-yl)-4-fluorophenyl)-5-methoxypicolinamide:

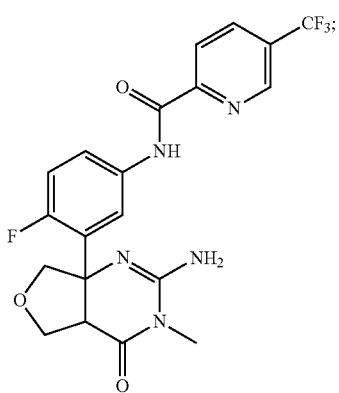

N-(3-(2-amino-3-methyl-4-oxo-3,4,4a,5,7,7a-hexahydro-furo[3,4-d]pyrimidin-7a-yl)-4-fluorophenyl)-5-(difluoromethyl)picolinamide:

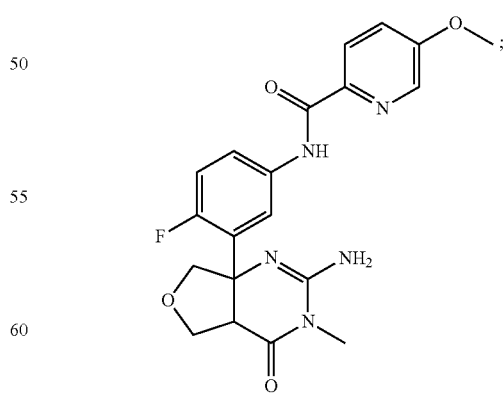

N-(3-(2-amino-3-methyl-4-oxo-3,4,4a,5,7,7a-hexahydro-furo[3,4-d]pyrimidin-7a-yl)-4-fluorophenyl)-5-(difluoromethoxy)picolinamide:

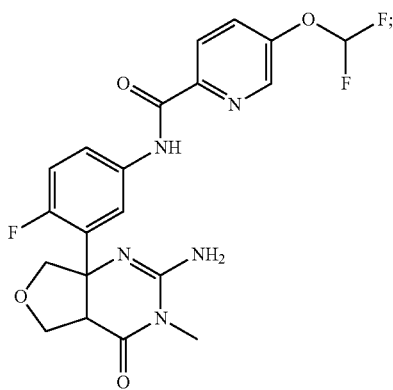 [SMILES: CN1C(=O)C2COCC2(c2cc(NC(=O)c3ccc(OC(F)F)cn3)ccc2F)N=C1N]

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-(difluoromethyl)pyrazine-2-carboxamide:

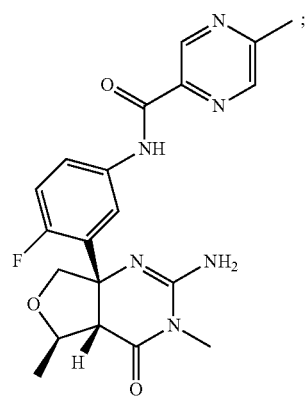

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methylpicolinamide:

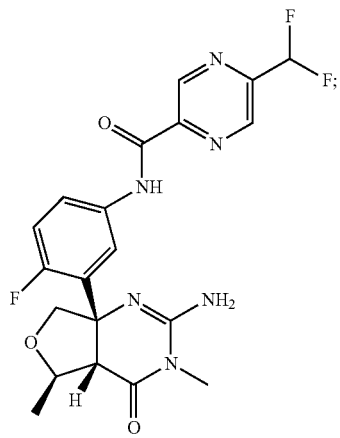 [SMILES: C[C@H]1OC[C@]2(c3cc(NC(=O)c4cnc(C(F)F)cn4)ccc3F)N=C(N)N(C)C(=O)[C@H]12]

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methoxypyrazine-2-carboxamide:

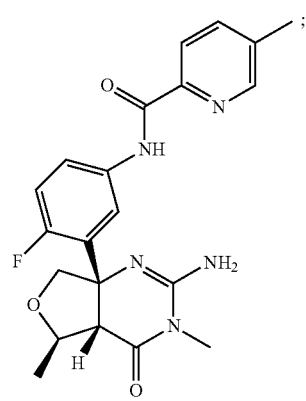

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-(trifluoromethyl)picolinamide:

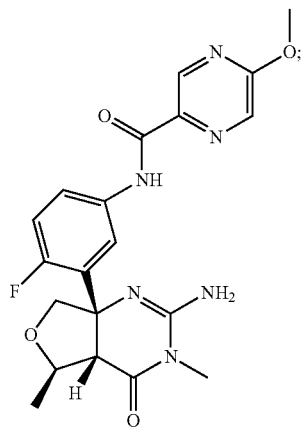 [SMILES: COc1cnc(C(=O)Nc2ccc(F)c([C@]34CO[C@H](C)[C@H]3C(=O)N(C)C(N)=N4)c2)cn1]

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-methylpyrazine-2-carboxamide:

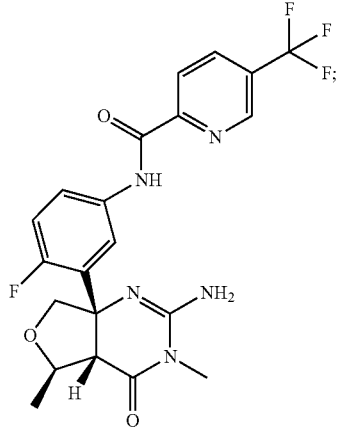

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-cyanopicolinamide:

11

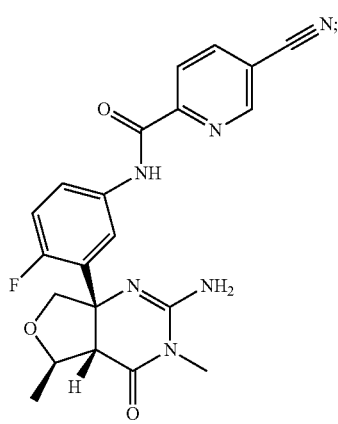 [SMILES: C[C@H]1OC[C@]2(c3cc(NC(=O)c4ccc(C#N)cn4)ccc3F)N=C(N)N(C)C(=O)[C@H]12]

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide:

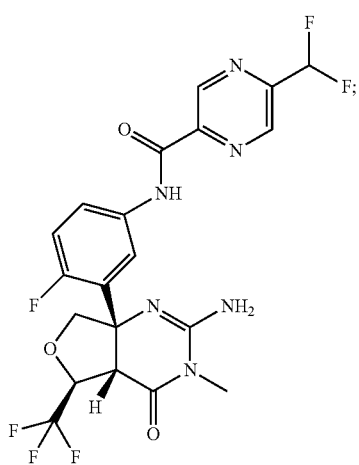 [SMILES: CN1C(=O)[C@@H]2[C@@H](C(F)(F)F)OC[C@]2(c2cc(NC(=O)c3cnc(C(F)F)cn3)ccc2F)N=C1N]

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methoxypyrazine-2-carboxamide:

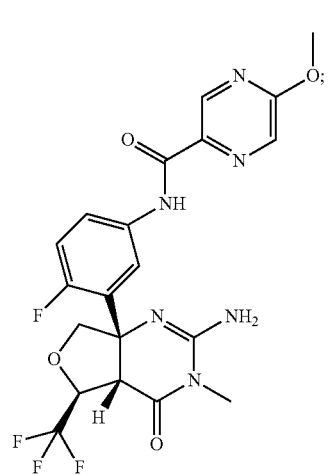 [SMILES: COc1cnc(C(=O)Nc2ccc(F)c([C@]34CO[C@H](C(F)(F)F)[C@H]3C(=O)N(C)C(N)=N4)c2)cn1]

12

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methylpicolinamide:

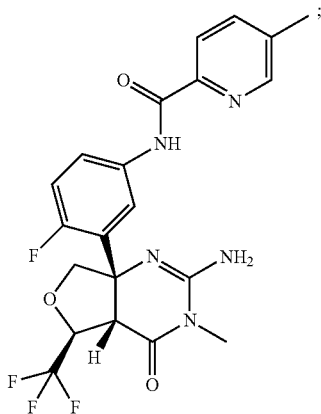 [SMILES: Cc1ccc(C(=O)Nc2ccc(F)c([C@]34CO[C@H](C(F)(F)F)[C@H]3C(=O)N(C)C(N)=N4)c2)nc1]

N-(3-((4aS,5S,7aS)-2-Amino-3-methyl-4-oxo-5-(trifluoromethyl)-3,4,4a,5,7,7a-hexahydrofuro[3,4-d]pyrimidin-7a-yl)-4-fluorophenyl)-5-cyanopicolinamide:

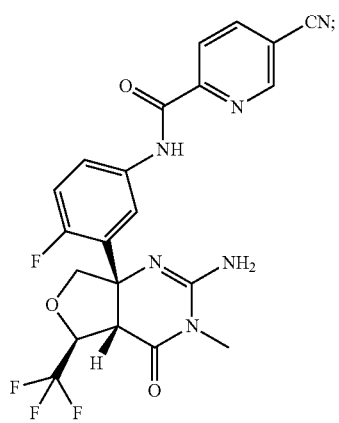 [SMILES: CN1C(=O)[C@@H]2[C@@H](C(F)(F)F)OC[C@]2(c2cc(NC(=O)c3ccc(C#N)cn3)ccc2F)N=C1N]

N-(3-((4aS,5S,7aS)-2-Amino-3-ethyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide:

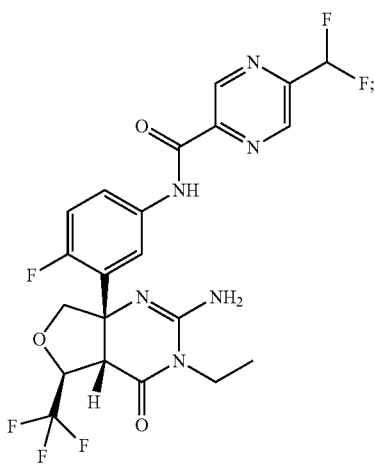 [SMILES: CCN1C(=O)[C@@H]2[C@@H](C(F)(F)F)OC[C@]2(c2cc(NC(=O)c3cnc(C(F)F)cn3)ccc2F)N=C1N]

and

N-(3-((4aS,5R,7aS)-2-Amino-3-ethyl-5-methyl-4-oxo-3,4,4a,5,7,7a-hexahydrofuro[3,4-d]pyrimidin-7a-yl)-4-fluorophenyl)-5-(difluoromethyl)pyrazine-2-carboxamide:

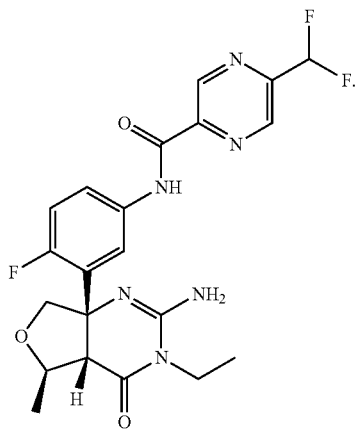 [SMILES: CCN1C(=O)[C@@H]2[C@@H](C)OC[C@]2(c2cc(NC(=O)c3cnc(C(F)F)cn3)ccc2F)N=C1N]

[10] The compound or pharmaceutically acceptable salt thereof or solvate thereof according to any one of [1] to [9] above, wherein the compound has the following stereochemistry:

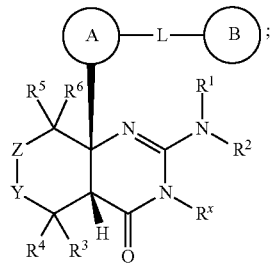

[11] A pharmaceutical composition comprising the compound or pharmaceutically acceptable salt thereof or solvate thereof according to any one of [1] to [10] above as an active ingredient;

[12] The compound or pharmaceutically acceptable salt thereof or solvate thereof according to any one of [1] to [10] above or the pharmaceutical composition according to [11] above for inhibiting production of amyloid-βprotein;

[13] The compound or pharmaceutically acceptable salt thereof or solvate thereof according to any one of [1] to [10] above or the pharmaceutical composition according to [11] above for inhibiting beta-site amyloid-βprecursor protein cleaving enzyme 1 (BACE1);

[14] The compound or pharmaceutically acceptable salt thereof or solvate thereof according to any one of [1] to [10] above or the pharmaceutical composition according to any one of [11] to [13] above for treating a neurodegenerative disease;

[15] The compound or pharmaceutically acceptable salt thereof or solvate thereof or the pharmaceutical composition according to [14] above, wherein the neurodegenerative disease is Alzheimer-type dementia or Down's syndrome;

[16] A method of inhibiting production of amyloid-b protein and/or of treating or preventing a neurodegenerative disease, such as Alzheimer-type dementia and Down's syndrome, the method involving administering to a human subject suffering from the condition a therapeutically or prophylactically effective amount of a compound or pharmaceutically acceptable salt thereof according to any one of [1] to [10] above or the pharmaceutical composition according to [11] above; and

[17] Use of a compound or a pharmaceutically acceptable salt thereof according to any one of [1] to [10] above, for the manufacture of a medicament for the treatment or prevention of a neurodegenerative disease.

DETAILED DESCRIPTION OF THE INVENTION

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{2}H$, $^{3}H$, $^{11}C$, $^{14}C$, $^{18}F$, $^{35}S$, $^{123}I$ and $^{125}I$.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^{3}H$ and/or $^{14}C$ are incorporated, are useful in drug and/or substrate tissue distribution assays. $^{3}H$ and $^{14}C$ are considered useful due to their ease of preparation and detectability. $^{11}C$ and $^{18}F$ isotopes are considered useful in PET (positron emission tomography), and $^{125}I$ isotopes are considered useful in SPECT (single photon emission computerized tomography), all useful in brain imaging. Substitution with heavier isotopes such as $^{2}H$ can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The "halogen atom" herein refers to fluorine, chlorine, bromine, iodine or the like and is preferably fluorine or chlorine.

The "$C_{1-6}$ alkyl group" refers to an alkyl group having 1 to 6 carbon atoms. Preferable examples of the group include linear or branched alkyl groups such as methyl, ethyl, n-propyl, isopropyl, n-butyl, isobutyl, t-butyl, n-pentyl, isopentyl, neopentyl, n-hexyl, 1-methylpropyl, 1,2-dimethylpropyl, 1-ethylpropyl, 1-methyl-2-ethylpropyl, 1-ethyl-2-methylpropyl, 1,1,2-trimethylpropyl, 1-methylbutyl, 2-methylbutyl, 1,1-dimethylbutyl, 2,2-dimethylbutyl, 2-ethylbutyl, 1,3-dimethylbutyl, 2-methylpentyl and 3-methylpentyl. The group is more preferably methyl, ethyl or n-propyl.

The "$C_{2-6}$ alkenyl group" refers to an alkenyl group having 2 to 6 carbon atoms. Preferable examples of the group include linear or branched alkenyl groups such as vinyl, allyl, 1-propenyl, isopropenyl, 1-buten-1-yl, 1-buten-2-yl, 1-buten-3-yl, 2-buten-1-yl and 2-buten-2-yl.

The "$C_{2-6}$ alkynyl group" refers to an alkynyl group having 2 to 6 carbon atoms. Preferable examples of the group include linear or branched alkynyl groups such as ethynyl, 1-propynyl, 2-propynyl, butynyl, pentynyl and hexynyl.

The "$C_{1-6}$ alkoxy group" refers to an alkyl group having 1 to 6 carbon atoms in which one methylene group is replaced by an oxygen atom. Examples of the group include methoxy, ethoxy, n-propoxy, isopropoxy, n-butoxy, isobutoxy, sec-butoxy, t-butoxy, n-pentoxy, isopentoxy, sec-pentoxy, t-pentoxy, n-hexyloxy, isohexyloxy, 1,2-dimethylpropoxy, 2-ethylpropoxy, 1-methyl-2-ethylpropoxy, 1-ethyl-2-methylpropoxy, 1,1,2-trimethylpropoxy, 1,1-dimethylbutoxy, 2,2-dimethylbutoxy, 2-ethylbutoxy, 1,3-dimethylbutoxy, 2-methylpentoxy, 3-methylpentoxy and hexyloxy.

The "$C_{1-6}$ alkylthio group" refers to an alkyl group having 1 to 6 carbon atoms in which one methylene group is replaced by a sulfur atom. Examples of the group include methylthio, ethylthio, n-propylthio, isopropylthio, n-butylthio, isobutylthio, t-butylthio, n-pentylthio, isopentylthio, neopentylthio, n-hexylthio and 1-methylpropylthio.

The "$C_{1-6}$ alkylsulfonyl group" refers to an alkyl group having 1 to 6 carbon atoms in which one methylene group is replaced by a sulfonyl group. Examples of the group include methylsulfonyl, ethylsulfonyl, n-propylsulfonyl, isopropylsulfonyl, n-butylsulfonyl, isobutylsulfonyl, t-butylsulfonyl, n-pentylsulfonyl, isopentylsulfonyl, neopentylsulfonyl, n-hexylsulfonyl and 1-methylpropylsulfonyl.

The "$C_{1-6}$ alkylcarbonyl group" refers to an alkyl group having 1 to 6 carbon atoms in which one methylene group is replaced by a carbonyl group. Preferable examples of the group include acetyl, propionyl and butyryl.

The "$C_{6-14}$ aryl group" refers to an aromatic hydrocarbon ring group having 6 to 14 carbon atoms. Examples of the group include phenyl, naphthyl and anthryl. Phenyl is particularly preferred.

The "$C_{7-12}$ aralkyl group" refers to a group having 7 to 12 carbon atoms in which an aromatic hydrocarbon ring such as a phenyl group or a naphthyl group is substituted with a $C_{1-6}$ alkyl group. Examples of the group include benzyl, phenethyl, phenylpropyl and naphthylmethyl. Benzyl is particularly preferred.

The "$C_{6-14}$ aryloxycarbonyl group" refers to a group in which oxycarbonyl is bonded to an aromatic hydrocarbon ring group having 6 to 14 carbon atoms. Preferable examples of the group include phenyloxycarbonyl, naphthyloxycarbonyl and anthryloxycarbonyl. Phenyloxycarbonyl is preferred.

The "$C_{6-14}$ arylcarbonyl group" refers to a group in which a carbonyl group is bonded to an aromatic hydrocarbon ring group having 6 to 14 carbon atoms. Preferable examples of the group include benzoyl and naphthoyl. Benzoyl is more preferred.

The "$C_{6-14}$ arylsulfonyl group" refers to a group in which a sulfonyl group is bonded to an aromatic hydrocarbon ring group having 6 to 14 carbon atoms. Preferable examples of the group include benzenesulfonyl and naphthylsulfonyl. Benzenesulfonyl is more preferred.

The "$C_{3-8}$ cycloalkyl group" refers to a cyclic alkyl group having 3 to 8 carbon atoms. Preferable examples of the group include cyclopropyl, cyclobutyl, cyclopentyl, cyclohexyl, cycloheptyl and cyclooctyl.

The "$C_{3-8}$ cycloalkoxy group" refers to a cyclic alkyl group having 3 to 8 carbon atoms in which one hydrogen atom is replaced by an oxygen atom. Examples of the group include cyclopropoxy, cyclobutoxy, cyclopentoxy, a cyclohexyloxy, cycloheptyloxy and cyclooctyloxy.

The "$C_{3-8}$ cycloalkylthio group" refers to a cyclic alkyl group having 3 to 8 carbon atoms in which one hydrogen atom is replaced by a sulfur atom. Examples of the group include cyclopropylthio, cyclobutylthio, cyclopentylthio, cyclohexylthio, cycloheptylthio and cyclooctylthio.

The "5- to 10-membered heterocyclic group" refers to a heteroatom-containing cyclic group having 5 to 10 members in total. Preferable examples of the group include piperidinyl, pyrrolidinyl, azepinyl, azocanyl, piperazinyl, 1,4-diazepanyl, morpholinyl, thiomorpholinyl, pyrrolyl, imidazolyl, pyrazolyl, pyridinyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, quinolinyl, isoquinolinyl, benzofuryl, benzopyranyl, benzimidazolyl, benzotriazolyl, benzisothiazolyl, indolinyl, isoindolinyl, chromanyl, isochromanyl, 1,3-dioxaindanyl and 1,4-dioxatetralinyl.

The "5- to 6-membered heteroaryl group" refers to the "5- to 10-membered heterocyclic group" which is a heteroatom-containing aromatic cyclic group having 5 to 6 members in total. Examples of the group include pyrrolyl, imidazolyl, pyrazolyl, pyridinyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl.

The "9- to 10-membered benzo-fused heterocyclic group" refers to the "5- to 10-membered heterocyclic group" which is a heteroatom-containing cyclic group having 9 to 10 members in total fused with a benzene ring. Preferable examples of the group include indolinyl, isoindolinyl, chromanyl, isochromanyl, 1,3-dioxaindanyl and 1,4-dioxatetralinyl.

The "3- to 10-membered carbocyclic group" refers to a carbocyclic group having 3 to 10 members in total. Preferable examples of the group include cyclopropyl, cyclobutyl, cyclopentyl, cyclohexyl, cycloheptyl, cyclooctyl, spiro[3.4] octanyl, decanyl, indanyl, 1-acenaphthenyl, cyclopentacyclooctenyl, benzocyclooctenyl, indenyl, tetrahydronaphthyl, 6,7,8,9-tetrahydro-5H-benzocycloheptenyl and 1,4-dihydronaphthalenyl.

The "$C_{1-6}$ alkylene group" refers to a divalent group derived by excluding any one hydrogen atom from the "$C_{1-6}$ alkyl group" as defined above. Examples of the group include methylene, 1,2-ethylene, 1,1-ethylene, 1,3-propylene, tetramethylene, pentamethylene and hexamethylene.

The "$C_{2-6}$ alkenylene group" refers to a divalent group derived by excluding any one hydrogen atom from the "$C_{2-6}$ alkenyl group" as defined above. Examples of the group include 1,2-vinylene (ethenylene), propenylene, butenylene, pentenylene and hexenylene.

The "$C_{2-6}$ alkynylene group" refers to a divalent group derived by excluding any one hydrogen atom from the "$C_{2-6}$ alkynyl group" as defined above. Examples of the group include ethynylene, propynylene, butynylene, pentynylene and hexynylene.

Examples of the "$C_{1-3}$ alkylene group" include methylene, ethylene and propylene.

Examples of the "$C_{2-3}$ alkenylene group" include 1,2-vinylene (ethenylene) and propenylene.

Examples of the "$C_{2-3}$ alkynylene group" include ethynylene and propynylene.

Examples of the sulfonylamino group which may be substituted with a $C_{1-6}$ alkyl group in the "sulfonylamino group (wherein the sulfonylamino group may be substituted with a $C_{1-6}$ alkyl group)" include methylsulfonylmethylamino, ethylsulfonylmethylamino and ethylsulfonylethylamino.

"Substituent Group α" refers to a hydrogen atom, a halogen atom, a hydroxy group, a nitro group, a $C_{1-6}$ alkylthio group, a $C_{6-14}$ aryl group, aryloxycarbonyl, a $C_{6-14}$ group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group may be substituted with a $C_{1-6}$ alkyl group), a $C_{2-6}$ alkenyl group which may have 1 to 3 substituents selected from Substituent Group β, a $C_{2-6}$ alkynyl group which may have 1 to 3 substituents selected from Substituent Group β, a carbamoyl group which may be substituted with one or two $C_{1-6}$ alkyl groups, a $C_{1-6}$ alkoxy group which may have 1 to 3 substituents selected from Substituent Group β, a $C_{1-6}$ alkyl group which may have 1 to 3 substituents selected from Substituent Group β and a 5- to 10-membered heterocyclic group which may have 1 to 3 substituents selected from Substituent Group β.

"Substituent Group β" refers to a halogen atom, a cyano group, a hydroxy group, a $C_{1-6}$ alkoxy group, a $C_{1-6}$ alkyl group, a $C_{3-8}$ cycloalkyl group and an oxo group.

The fused aminodihydropyrimidone derivative of the formula (I) according to the present invention may be a pharmaceutically acceptable salt. Pharmaceutically acceptable salts include those described by Berge, Bighley and Monkhouse, J. Pharm. Sci., 1977, 766, 1-19. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The fused aminodihydropyrimidone derivative of the formula (I) or pharmaceutically acceptable salt according to the present invention may be a solvate thereof. Examples of the solvate include a hydrate.

The compound (I) is not limited to a specific isomer and includes all possible isomers (such as a keto-enol isomer, an imine-enamine isomer, a diastereoisomer, an optical isomer and a rotamer) and racemates. For example, the compound (I) wherein $R^1$ is hydrogen includes the following tautomers:

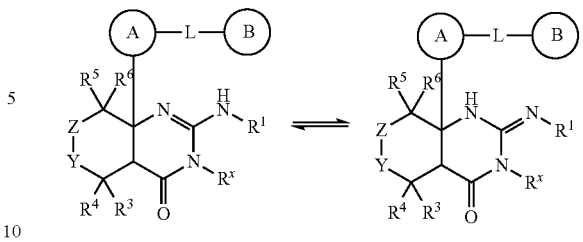

The fused aminodihydropyrimidone derivative of the formula (I) according to the present invention is preferably a compound of the formula (I), wherein Y is —$NR^Y$— (wherein $R^Y$ is a hydrogen atom, a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α), an oxygen atom or a sulfur atom. More preferably, Y is an oxygen atom or a sulfur atom. Most preferably, Y is an oxygen atom.

The fused aminodihydropyrimidone derivative of the formula (I) according to the present invention is preferably a compound of the formula (I), wherein Z is a single bond.

The fused aminodihydropyrimidone derivative of the formula (I) according to the present invention is preferably a compound of the formula (I), wherein L is a single bond, a formula —$NR^eCO$— (wherein $R^e$ is a hydrogen atom or a $C_{1-6}$ alkyl group which optionally has 1 to 3 substituents selected from Substituent Group α) or a formula —$NR^eSO_2$— (wherein $R^e$ is a hydrogen atom or a $C_{1-6}$ alkyl group which optionally has 1 to 3 substituents selected from Substituent Group α); or wherein L is a single bond, an oxygen atom, a $C_{1-6}$ alkylene group which optionally has 1 to 3 substituents selected from Substituent Group α, a $C_{2-6}$ alkenylene group which optionally has 1 to 3 substituents selected from Substituent Group α or a $C_{2-6}$ alkynylene group which optionally has 1 to 3 substituents selected from Substituent Group α. More preferably, L is a formula —$NR^eCO$— (wherein $R^e$ is a hydrogen atom or a $C_{1-6}$ alkyl group which optionally has 1 to 3 substituents selected from Substituent Group α). Most preferably, L is NH—CO—. Especially, L is NH—CO where the nitrogen atom is attached to Ring A and the carbon atom is attached to Ring B.

The fused aminodihydropyrimidone derivative of the formula (I) according to the present invention is preferably a compound of the formula (I), wherein Ring A is a $C_{6-14}$ aryl group which optionally has 1 to 3 substituents selected from Substituent Group α. More preferably, Ring A is a $C_{6-10}$ aryl group which optionally has 1 to 2 substituents selected from Substituent Group α. Most preferably, Ring A is a phenyl group which optionally has 1 or 2 substituents selected from a halogen atom, a hydroxy group, a nitro group or a cyano group. Especially, Ring A is a phenyl group which is optionally substituted by a halogen atom. More especially, Ring A is a phenyl group which is optionally substituted by fluorine or chlorine. Most especially, Ring A is a phenyl group substituted by fluorine.

The fused aminodihydropyrimidone derivative of the formula (I) according to the present invention is preferably a compound of the formula (I), wherein Ring B is a 5 to 10-membered heterocyclic group which optionally has 1 to 3 substituents selected from Substituent Group α. More preferably, Ring B is a 5 to 8-membered heterocyclic group which optionally has 1 to 2 substituents selected from Substituent Group α. Most preferably, Ring B is a 5- or 6-membered heterocyclic group which optionally has 1 or 2 substituents selected from a halogen atom, a hydroxy atom, a nitro group, $C_{1-6}$ alkylthio group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group is optionally substituted with a $C_{1-6}$ alkyl group), a $C_{2-6}$ alkenyl group which optionally has 1 to 3 substituents selected from Substituent Group β, a $C_{2-6}$ alkynyl group which optionally has 1 to 3 substituents selected from Substituent Group β, a $C_{1-6}$ alkoxy group which optionally has 1 to 3 substituents selected from Substituent Group β and a $C_{1-6}$ alkyl group which optionally has 1 to 3 substituents selected from Substituent Group β. Especially, Ring B is a 6-membered heterocyclic group which is optionally substituted by a halogen atom, a cyano group, a $C_{1-6}$ alkyl group which optionally has 1 to 3 substituents selected from Substituent Group β or a $C_{1-6}$ alkoxy group which optionally has 1 to 3 substituents selected from Substituent Group β. More especially, Ring B is pyridine or pyrazine, optionally substituted by a $C_{1-6}$ alkyl group which optionally has 1 to 3 substituents selected from a halogen atom, a cyano group, a hydroxy group and a $C_{1-6}$ alkoxy group. Most especially, Ring B is pyrazine optionally substituted by a $C_{1-3}$ alkyl group which optionally has 1 to 2 halogen atom substituents. Particularly, Ring B is pyrazine optionally substituted by a methyl group which optionally has 1 or 2 fluorine or chlorine atom substituents. More particularly, Ring B is pyrazine substituted by a difluoromethyl group. Examples of suitable substituted Ring B groups are 5-fluoropyridin-2-yl, 5-cyanopyridin-2-yl, 5-chloropyridin-2-yl, 5-trifluoromethylpyridin-2-yl, 5-difluoromethylpyridin-2-yl, 5-fluoromethylpyridin-2-yl, 5-methoxypyridin-2-yl, 5-difluoromethoxypyridin-2-yl, 5-methoxypyrazin-2-yl, 5-difluoromethylpyrazin-2-yl, 5-difluoromethoxypyrazin-2-yl, 5-fluoromethoxypyrazin-2-yl and 5-ethoxypyrazin-2-yl. Further examples of suitable substituted Ring B groups are 5-methylpyridin-2-yl and 5-methylpyrazin-2-yl.

The fused aminodihydropyrimidone derivative of the formula (I) according to the present invention is preferably a compound of the formula (I), wherein $R^1$ and $R^2$ are each independently a hydrogen atom or a $C_{1-6}$ alkyl group which optionally has 1 to 3 substituents selected from Substituent Group α. More preferably, $R^1$ and $R^2$ are each independently a hydrogen atom or a $C_{1-3}$ alkyl group which optionally has 1 to 2 substituents selected from a halogen atom, a hydroxyl group, a nitro group and a cyano group. Most preferably, $R^1$ and $R^2$ are each independently a hydrogen atom or a $C_{1-2}$ alkyl group which optionally has 1 or 2 substituents selected from fluorine, chlorine, bromine, a hydroxyl group, a nitro group and a cyano group. Especially, $R^1$ and $R^2$ are both hydrogen.

The fused aminodihydropyrimidone derivative of the formula (I) according to the present invention is preferably a compound of the formula (I), wherein $R^3$ and $R^4$ are each independently a hydrogen atom, a halogen atom, a hydroxy group, a $C_{1-6}$ alkyl group which optionally has 1 to 3 substituents selected from Substituent Group α or a $C_{1-6}$ alkoxy group which optionally has 1 to 3 substituents selected from Substituent Group α. More preferably, $R^3$ and $R^4$ are independently a hydrogen atom or a $C_{1-6}$ alkyl group which optionally has 1 to 3 substituents selected from Substituent Group α. Most preferably, $R^3$ and $R^4$ are independently a hydrogen atom or a $C_{1-3}$ alkyl group which optionally has 1 to 3 substituents selected from a halogen atom, a hydroxy atom, a nitro group and a cyano group. Especially, $R^3$ and $R^4$ are independently a hydrogen atom or a $C_{1-2}$ alkyl group which is optionally substituted by a halogen atom, a hydroxy atom, a methoxy group, a nitro group or a cyano group. More especially, $R^3$ and $R^4$ are independently a hydrogen atom or a methyl group which is optionally substituted by a halogen atom. Most especially, especially, $R^3$ and $R^4$ are independently a hydrogen atom or a methyl group optionally substituted by a fluorine atom. Particularly, $R^3$ and $R^4$ are independently a hydrogen atom or a methyl group. Particularly, $R^3$ and $R^4$ are both hydrogen. Examples of suitable $R^3$ groups are a hydrogen atom, a methyl group, a monofluoromethyl group, a difluoromethyl group, a trifluoromethyl group and a methoxymethyl group.

The fused aminodihydropyrimidone derivative of the formula (I) according to the present invention is preferably a compound of the formula (I), wherein $R^5$ and $R^6$ are each independently a hydrogen atom, a halogen atom, a hydroxy group, a $C_{1-6}$ alkyl group which optionally has 1 to 3 substituents selected from Substituent Group α or a $C_{1-6}$ alkoxy group which optionally has 1 to 3 substituents selected from Substituent Group α. More preferably, $R^5$ and $R^6$ are independently a hydrogen atom or a $C_{1-6}$ alkyl group which optionally has 1 to 3 substituents selected from Substituent Group α. Most preferably, $R^5$ and $R^6$ are independently a hydrogen atom or a $C_{1-3}$ alkyl group which optionally has 1 to 2 substituents selected from a halogen atom, a hydroxy atom, a nitro group and a cyano group. Especially, $R^5$ and $R^6$ are independently a hydrogen atom or a $C_{1-2}$ alkyl group which is optionally substituted by a halogen atom, a hydroxy atom, a nitro group or a cyano group. More especially, $R^5$ and $R^6$ are independently a hydrogen atom or a methyl group which is optionally substituted by a halogen atom. Most especially, especially, $R^5$ and $R^6$ are independently a hydrogen atom or a methyl group especially, $R^5$ and $R^6$ are independently a hydrogen atom or a methyl group. Particularly, $R^5$ and $R^6$ are both hydrogen.

The fused aminodihydropyrimidone derivative of the formula (I) according to the present invention is preferably a compound of the formula (I), wherein $R^x$ is a hydrogen atom, a $C_{1-6}$ alkyl group which optionally has 1 to 3 substituents selected from Substituent Group α or a $C_{3-8}$ cycloalkyl group which optionally has 1 to 3 substituents selected from Substituent Group α. More preferably, $R^x$ is a hydrogen atom or a $C_{1-6}$ alkyl group which optionally has 1 to 3 substituents selected from Substituent Group α. Most preferably, $R^x$ is a hydrogen atom or a $C_{1-3}$ alkyl group which optionally has 1 to 3 substituents selected from a halogen atom, a hydroxy atom, a nitro group and a cyano group. Especially, $R^x$ is a hydrogen atom or a $C_{1-2}$ alkyl group which is optionally substituted by a halogen atom, a hydroxy atom, a methoxy group, a nitro group or a cyano group. More especially, $R^x$ is a hydrogen atom or a methyl group which is optionally substituted by a halogen atom. Most especially, $R^x$ is a hydrogen atom, or a methyl group optionally substituted by a fluorine atom. Particularly, $R^x$ is a hydrogen atom or a methyl group. More particularly, $R^x$ is methyl. Examples of suitable $R^x$ groups are methyl and ethyl.

One favoured group of compounds of the present invention is the compound of formula (Ia) and pharmaceutically acceptable salts thereof:

(Ia)

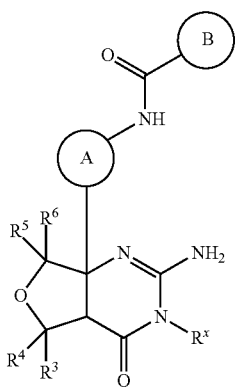

wherein Ring A, Ring B, $R^3$, $R^4$, $R^5$ and $R^6$ are as hereinbefore defined and $R^x$ is methyl or ethyl.

A further favoured group of compounds of the present invention is the compound of formula (Ii) and pharmaceutically acceptable salts thereof:

(Ii)

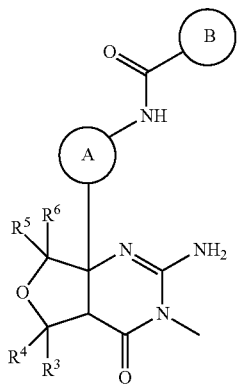

wherein Ring A, Ring B, $R^3$, $R^4$, $R^5$ and $R^6$ are as hereinbefore defined.

Preferred compounds of the present invention are:

N-(3-(2-amino-3-methyl-4-oxo-3,4,4a,5,7,7a-hexahydrofuro[3,4-d]pyrimidin-7a-yl)-4-fluorophenyl)-5-(difluoromethyl)pyrazine-2-carboxamide:

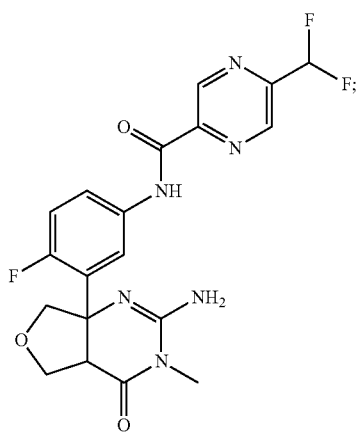 [SMILES: CN1C(=O)C2COCC2(c2cc(NC(=O)c3cnc(C(F)F)cn3)ccc2F)N=C1N]

N-(3-(2-amino-3-methyl-4-oxo-3,4,4a,5,7,7a-hexahydrofuro[3,4-d]pyrimidin-7a-yl)-4-fluorophenyl)-5-methoxypyrazine-2-carboxamide:

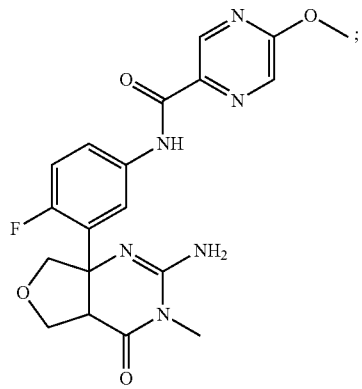 [SMILES: COc1cnc(C(=O)Nc2ccc(F)c(C34COCC3C(=O)N(C)C(N)=N4)c2)cn1]

N-(3-(2-amino-3-methyl-4-oxo-3,4,4a,5,7,7a-hexahydrofuro[3,4-d]pyrimidin-7a-yl)-4-fluorophenyl)-5-(difluoromethoxy)pyrazine-2-carboxamide:

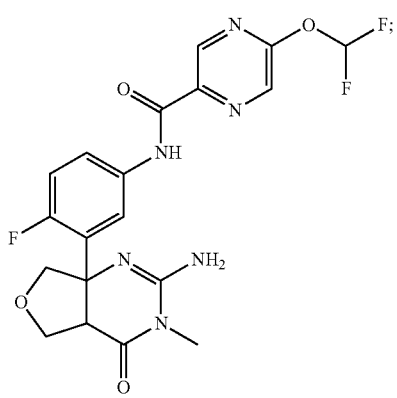

N-(3-(2-amino-3-methyl-4-oxo-3,4,4a,5,7,7a-hexahydrofuro[3,4-d]pyrimidin-7a-yl)-4-fluorophenyl)-5-(fluoromethoxy)pyrazine-2-carboxamide:

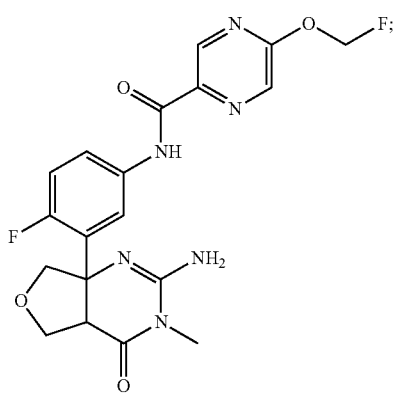

N-(3-(2-amino-3-methyl-4-oxo-3,4,4a,5,7,7a-hexahydrofuro[3,4-d]pyrimidin-7a-yl)-4-fluorophenyl)-5-ethoxypyrazine-2-carboxamide:

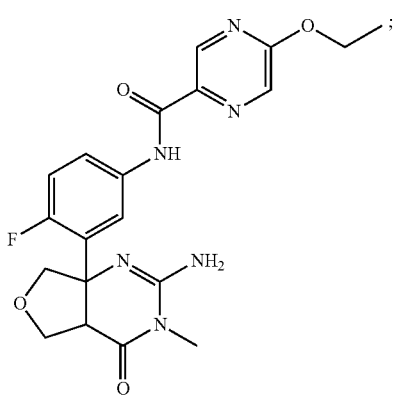 [SMILES: CCOc1cnc(C(=O)Nc2ccc(F)c(C34COCC3C(=O)N(C)C(N)=N4)c2)cn1]

N-(3-(2-amino-3-methyl-4-oxo-3,4,4a,5,7,7a-hexahydro-furo[3,4-d]pyrimidin-7a-yl)-4-fluorophenyl)-5-fluoropicolinamide:

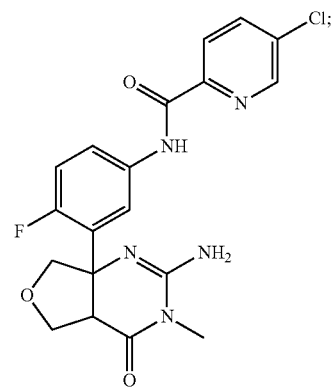

N-(3-(2-amino-3-methyl-4-oxo-3,4,4a,5,7,7a-hexahydro-furo[3,4-d]pyrimidin-7a-yl)-4-fluorophenyl)-5-(trifluoromethyl)picolinamide:

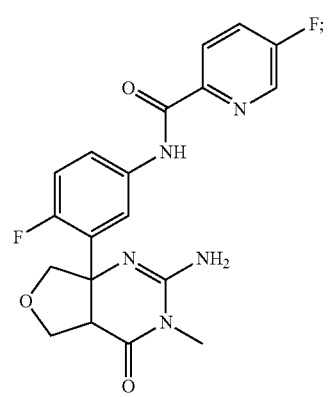

N-(3-(2-amino-3-methyl-4-oxo-3,4,4a,5,7,7a-hexahydro-furo[3,4-d]pyrimidin-7a-yl)-4-fluorophenyl)-5-cyanopicolinamide:

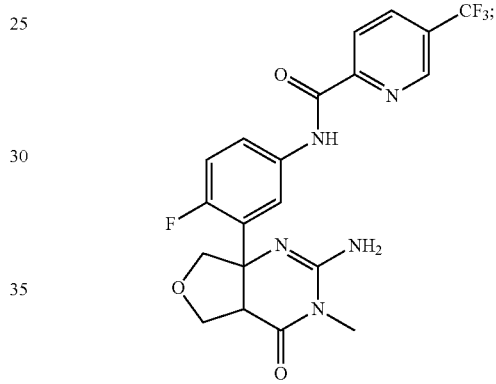

N-(3-(2-amino-3-methyl-4-oxo-3,4,4a,5,7,7a-hexahydro-furo[3,4-d]pyrimidin-7a-yl)-4-fluorophenyl)-5-(difluoromethyl)picolinamide:

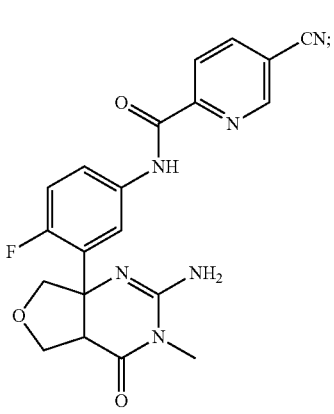 [SMILES: CN1C(=O)C2COCC2(c2cc(NC(=O)c3ccc(C#N)cn3)ccc2F)N=C1N]

N-(3-(2-amino-3-methyl-4-oxo-3,4,4a,5,7,7a-hexahydro-furo[3,4-d]pyrimidin-7a-yl)-4-fluorophenyl)-5-chloropicolinamide:

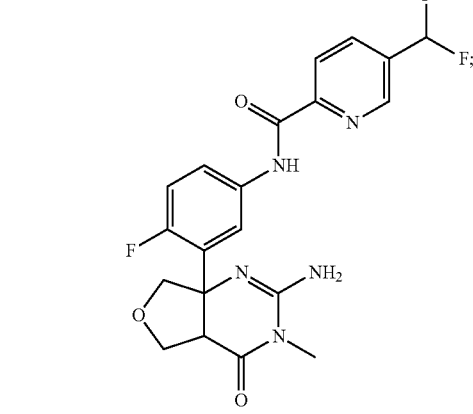

N-(3-(2-amino-3-methyl-4-oxo-3,4,4a,5,7,7a-hexahydro-furo[3,4-d]pyrimidin-7a-yl)-4-fluorophenyl)-5-(fluoromethyl)picolinamide:

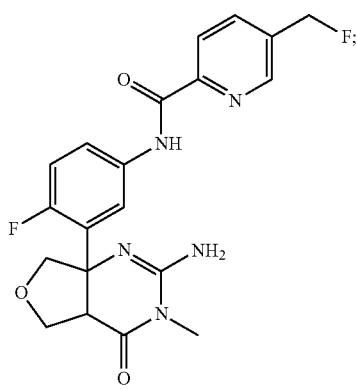 [SMILES: CN1C(=O)C2COCC2(c2cc(NC(=O)c3ccc(CF)cn3)ccc2F)N=C1N]

N-(3-(2-amino-3-methyl-4-oxo-3,4,4a,5,7,7a-hexahydro-furo[3,4-d]pyrimidin-7a-yl)-4-fluorophenyl)-5-methoxypicolinamide:

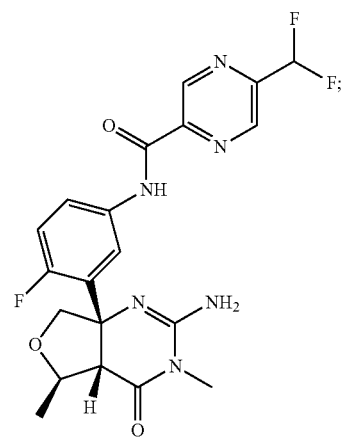

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methoxypyrazine-2-carboxamide:

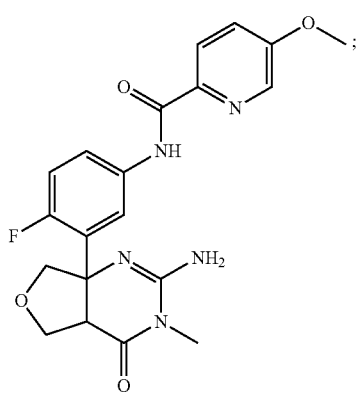 [SMILES: COc1ccc(C(=O)Nc2ccc(F)c(C34COCC3C(=O)N(C)C(N)=N4)c2)nc1]

and
N-(3-(2-amino-3-methyl-4-oxo-3,4,4a,5,7,7a-hexahydro-furo[3,4-d]pyrimidin-7a-yl)-4-fluorophenyl)-5-(difluoromethoxy)picolinamide:

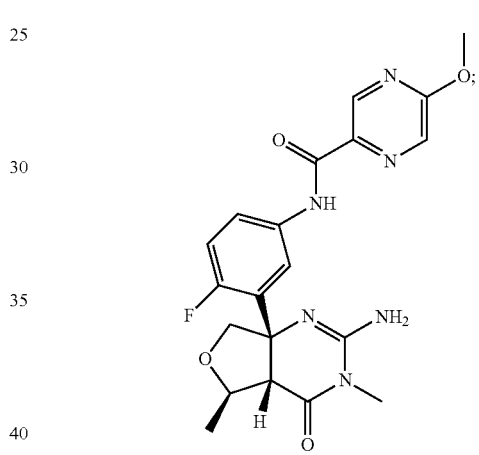

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-methylpyrazine-2-carboxamide:

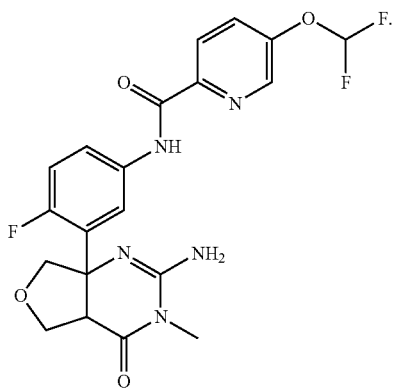 [SMILES: CN1C(=O)C2COCC2(c2cc(NC(=O)c3ccc(OC(F)F)cn3)ccc2F)N=C1N]

Further preferred compounds of the present invention are:
N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-(difluoromethyl)pyrazine-2-carboxamide:

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methylpicolinamide:

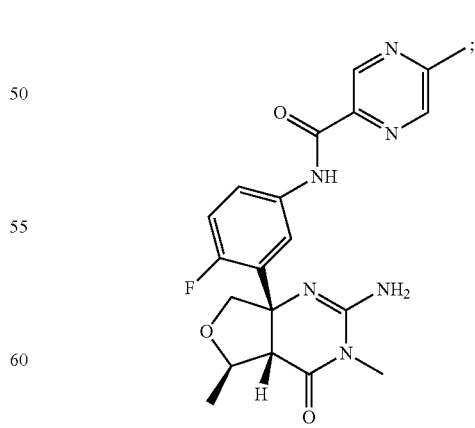

27 28

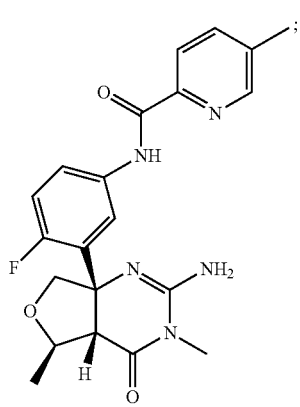 [SMILES: Cc1ccc(C(=O)Nc2ccc(F)c([C@]34CO[C@H](C)[C@H]3C(=O)N(C)C(N)=N4)c2)nc1]

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-(trifluoromethyl)picolinamide:

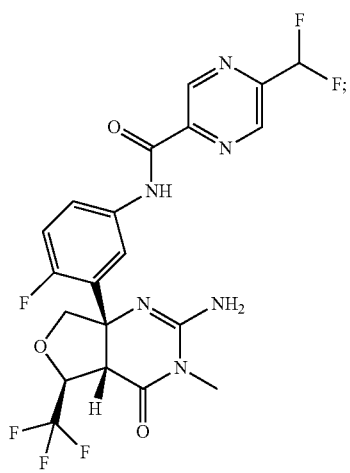

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methoxypyrazine-2-carboxamide:

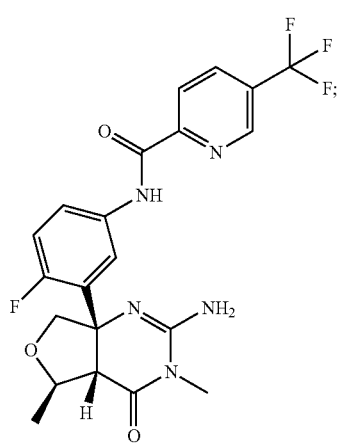 [SMILES: C[C@H]1OC[C@]2(c3cc(NC(=O)c4ccc(C(F)(F)F)cn4)ccc3F)N=C(N)N(C)C(=O)[C@H]12]

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-cyanopicolinamide:

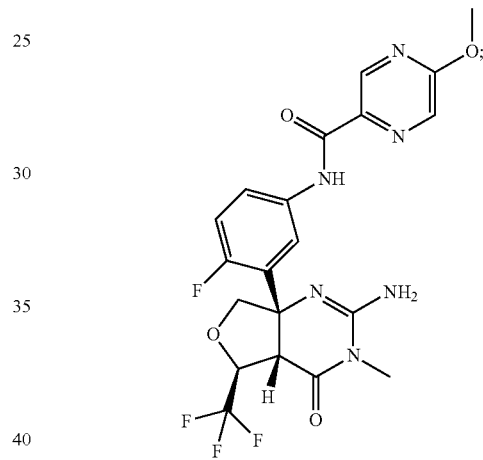

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methylpicolinamide:

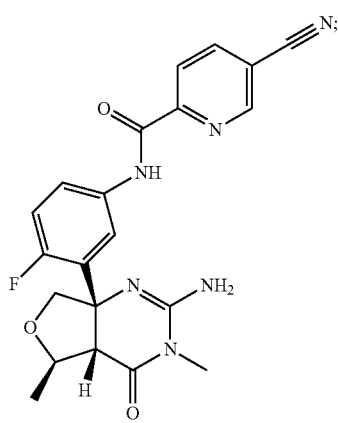 [SMILES: C[C@H]1OC[C@]2(c3cc(NC(=O)c4ccc(C#N)cn4)ccc3F)N=C(N)N(C)C(=O)[C@H]12]

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2

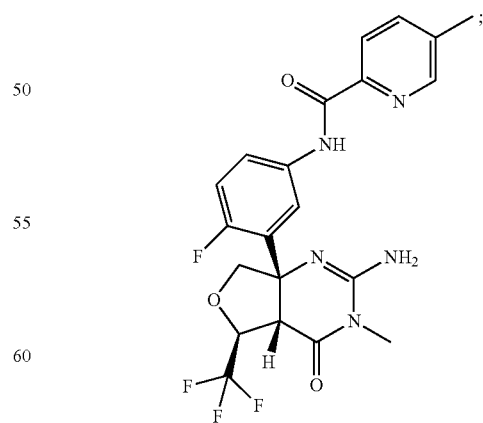

N-(3-((4aS,5S,7aS)-2-Amino-3-methyl-4-oxo-5-(trifluoromethyl)-3,4,4a,5,7,7a-hexahydrofuro[3,4-d]pyrimidin-7a-yl)-4-fluorophenyl)-5-cyanopicolinamide:

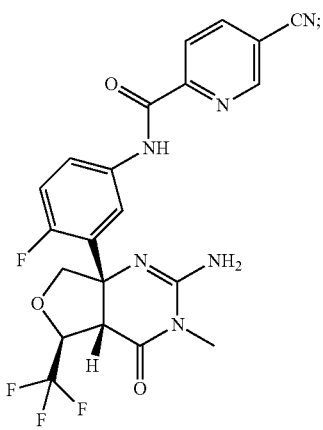 [SMILES: CN1C(=O)[C@@H]2[C@@H](C(F)(F)F)OC[C@]2(c2cc(NC(=O)c3ccc(C#N)cn3)ccc2F)N=C1N]

N-(3-((4aS,5S,7aS)-2-Amino-3-ethyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide:

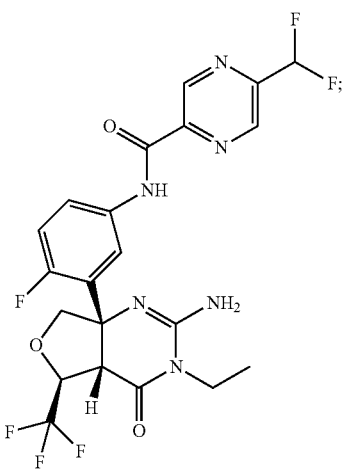 [SMILES: CCN1C(=O)[C@@H]2[C@@H](C(F)(F)F)OC[C@]2(c2cc(NC(=O)c3cnc(C(F)F)cn3)ccc2F)N=C1N]

and
N-(3-((4aS,5R,7aS)-2-Amino-3-ethyl-5-methyl-4-oxo-3,4,4a,5,7,7a-hexahydrofuro[3,4-d]pyrimidin-7a-yl)-4-fluorophenyl)-5-(difluoromethyl)pyrazine-2-carboxamide:

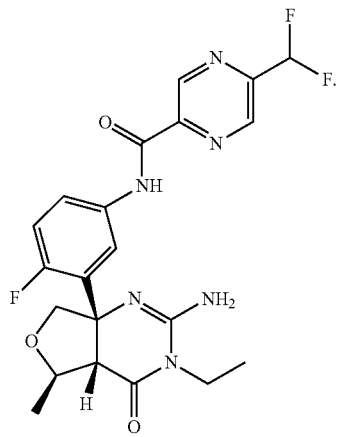

A preferred enantiomer of the compound of formula (I) is:

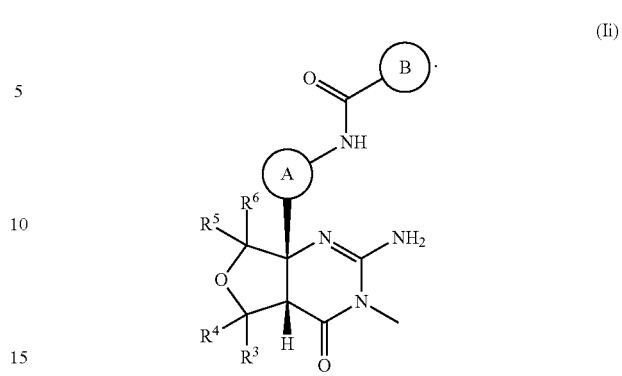

(Ii)

Next, methods for preparing the compound of the formula (I) [hereinafter referred to as compound (I); a compound represented by another formula is similarly described] or pharmaceutically acceptable salt thereof according to the present invention will be described.

The compound represented by the formula (I):

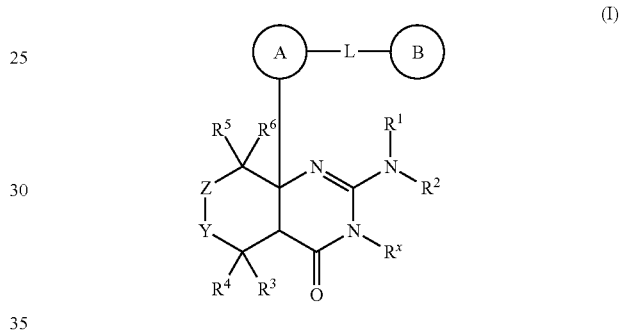

(I)

(wherein Ring A, Ring B, $R^1$, $R^2$, $R^3$, $R^4$, $R^5$, $R^6$, $R^x$, L, Y and Z are as defined above) or the intermediate thereof are synthesized by, for example, General Preparation Methods 1 to 15 as described below.

The "leaving group" in the raw material compound used in preparation of the compound (I) according to the present invention may be any leaving group used for nucleophilic substitution reaction. Preferable examples of the leaving group include a halogen atom, a $C_{1-6}$ alkylsulfonyloxy group which may be substituted with the above Substituent Group α and an arylsulfonyloxy group which may be substituted with the above Substituent Group α. Specific examples of the leaving group include a chlorine atom, a bromine atom, an iodine atom, a methanesulfonyloxy group, a trifluoromethanesulfonyloxy group and a p-toluenesulfonyloxy group.

[No General Preparation Methods 1 or 2]

3. General Preparation Method 3:

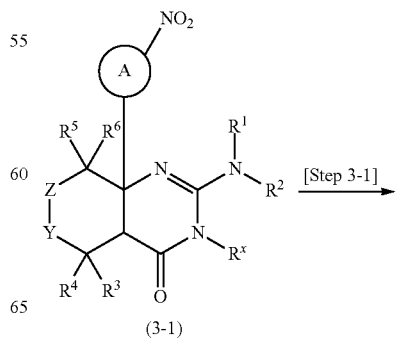

(3-1)

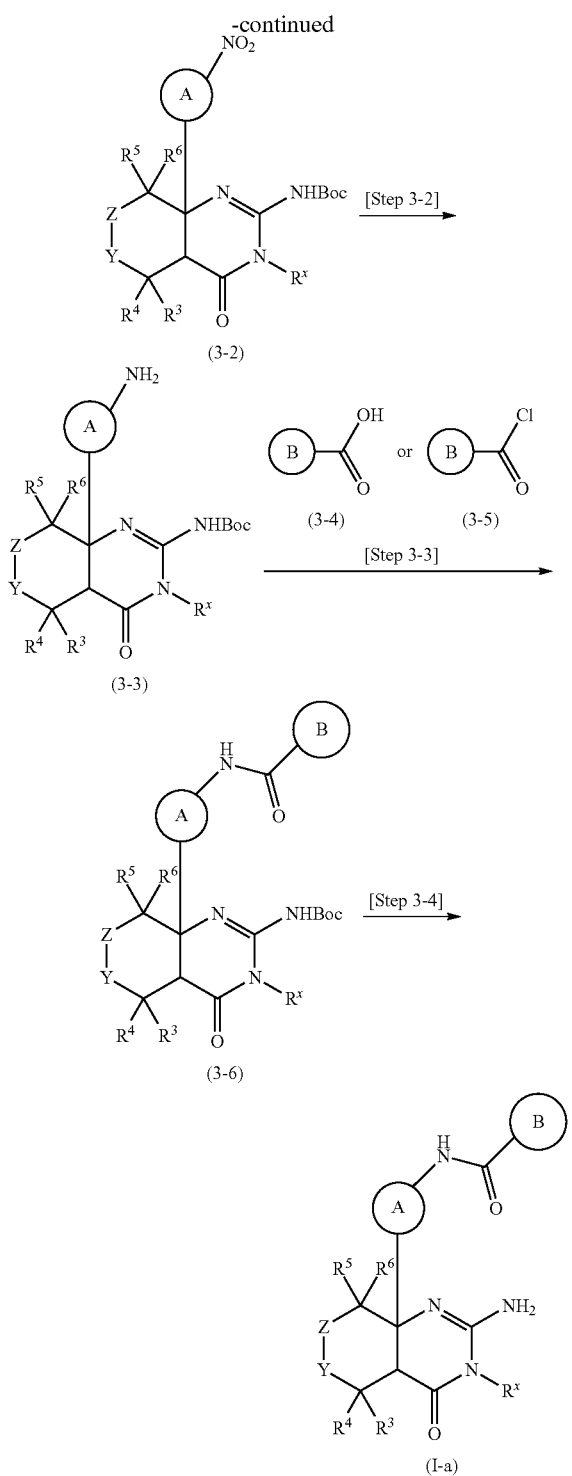

In the formula, Ring A, $R^1$, $R^2$, $R^3$, $R^4$, $R^5$, $R^6$, $R^x$, Y, Z and Ring B are as defined above.

General Preparation Method 3 is a method for preparing the compound of the general formula (I) according to the present invention, wherein L is —NHCO— and $R^1$ and $R^2$ are hydrogen atoms, from a compound (3-1) as a raw material through multiple steps of Step 3-1 to Step 3-4.

The compound (3-1) can be prepared from a commercially available product by the General Preparation Method 4 below, and can also be prepared by a method described in Preparation Examples among Examples. Compounds (3-4) and (3-5) each can be a commercially available product used as is, can also be prepared from a commercially available product by a method known to a person skilled in the art, and can further be prepared by a method described in Preparation Examples among Examples.

Step 3-1:

This step is a step of obtaining a compound (3-2) by t-butoxycarbonylation of the amino group of the compound (3-1) when $R^1$ and $R^2$ are both hydrogen.

The reaction can be performed under the same conditions as those generally used in t-butoxycarbonylation of an amino compound such as the conditions described in a document such as T. W. Green and P. G. M. Wuts, "Protective Groups in Organic Chemistry, Second Edition", John Wiley & Sons (1991), P. 327-330. The compound (3-2) can be obtained by reacting the compound (3-1) with di-tert-butyl dicarbonate using triethylamine as a base in a solvent such as tetrahydrofuran, for example.

Step 3-2:

This step is a step of obtaining a compound (3-3) from the compound (3-2).

The compound (3-3) is synthesized by reducing the nitro compound (3-2) by a synthesis method known to a person skilled in the art. Examples of the method include reduction by catalytic hydrogenation using a noble metal catalyst such as Raney nickel, palladium, ruthenium, rhodium or platinum or zinc powder in acetic acid. Or the reduction reaction may be conducted with iron under neutral conditions using ammonium chloride, for example. Preferable conditions include powdered zinc in acetic acid or catalytic hydrogenation with palladium on carbon.

Step 3-3:

This step is a step of obtaining a compound (3-6) by condensing the compound (3-3) with the compound (3-4) using a condensing agent. Alternatively, this step is a step of obtaining a compound (3-6) by condensing the compound (3-3) with the compound (3-5) by acylation reaction.

The condensation reaction of the compound (3-3) with the compound (3-4) using a condensing agent can be performed under the same conditions as those usually used and described in the following documents. Examples of the known method include those in Rosowsky, A.; Forsch, R. A.; Moran, R. G.; Freisheim, J. H.; J. Med. Chem., 34 (1), 227-234 (1991), Brzostwska, M.; Brossi, A.; Flippen-Anderson, J. L.; Heterocycles, 32 (10), 1968-1972 (1991), and Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; So, A. G.; Resnick, L.; Tarpley, W. G., Aristoff, P. A.; J. Med. Chem., 37 (7), 998-1014 (1994).

The compound (3-3) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene and xylene. Examples of the condensing agent include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC(N,N-dicyclohexylcarbodiimide), diethylphosphoryl cyanide, PyBOP (benzotriazol-1-yloxytris(pyrrolidino)phosphonium hexafluorophosphate) and EDC.HCl (1-ethyl-3-(3-dimethylaminopropyl)carbodiimide hydrochloride). One equivalent to a large excess of the compound (3-4) is used with respect to the compound (3-3). One equivalent to a large excess of an organic base such as triethylamine may be added where necessary.

The reaction time is not particularly limited and is usually 0.5 to 48 hours, and preferably 0.5 to 24 hours. The reaction temperature varies according to the raw material used, the solvent and the like and is not particularly limited. Ice-cold temperature to solvent reflux temperature is preferable.

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-a) obtained in General Preparation Method 3 with a corresponding halide compound such as a $C_{1-6}$ alkyl halide. Alternatively, —NHCO— of L in the compound (I-a) of the present invention can be converted to —NR$^e$CO— (wherein $R^e$ is a $C_{1-6}$ alkyl group which optionally has 1 to 3 substituents selected from Substituent Group α) by further reacting the compound (I-a) obtained in General Preparation Method 3 with a corresponding halide compound such as a $C_{1-6}$ alkyl halide.

The compound of the formula (I) according to the present invention, wherein L is —NR$^e$SO$_2$—, can be obtained using a corresponding sulfonyl halide compound in place of the compound (3-4) or (3-5) used in General Preparation Method 3.

In General Preparation Method 3, the compound (3-6) can also be prepared from the compound (3-3) and the compound (3-4) by a method described in the following alternative method (1) or (2).

Alternative Method (1):

The compound (3-6) can be obtained by converting the compound (3-4) to a mixed acid anhydride or a carbonic anhydride and then reacting the mixed acid anhydride or carbonic anhydride with the compound (3-3). The mixed acid anhydride or carbonic anhydride can be synthesized by a means known to a person skilled in the art. The synthesis is performed by reacting the compound (3-4) with a chloroformate such as ethyl chloroformate in the presence of a base such as triethylamine, for example. One to two equivalents of the chloroformate and the base are used with respect to the compound (3-4). The reaction temperature is −30° C. to room temperature, and preferably −20° C. to room temperature.

The step of condensing the mixed acid anhydride or carbonic anhydride with the compound (3-3) is performed by reacting the mixed acid anhydride or carbonic anhydride with the compound (3-3) in a solvent such as dichloromethane, tetrahydrofuran or N,N-dimethylformamide, for example. One equivalent to a large excess of the compound (3-3) is used with respect to the mixed acid anhydride or carbonic anhydride.

The reaction time is not particularly limited and is usually 0.5 to 48 hours, and preferably 0.5 to 12 hours. The reaction temperature is −20° C. to 50° C., and preferably −20° C. to room temperature.

Alternative Method (2):

The compound (3-6) can be obtained by converting the compound (3-4) to an active ester and then reacting the active ester with the compound (3-3). The step of obtaining the active ester is performed by reacting the compound (3-4) with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound (3-4). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound (3-3) is performed by reacting the active ester with the compound (3-3) in a solvent such as dichloromethane, tetrahydrofuran or N,N-dimethylformamide, for example. One equivalent to a large excess of the compound (3-3) is used with respect to the active ester. The reaction time is not particularly limited and is usually 0.5 to 48 hours, and preferably 0.5 to 24 hours. The reaction temperature is −20° C. to 50° C., and preferably −20° C. to room temperature.

In this acylation reaction, the compound (3-6) can be obtained from the compounds (3-3) and (3-5) by a method known to a person skilled in the art.

Examples of the base used in the reaction include triethylamine, pyridine, potassium carbonate and diisopropylethylamine. The reaction temperature is not particularly limited and is usually −78° C. to solvent reflux temperature, and preferably −20° C. to room temperature. The solvent used in the reaction is not particularly limited insofar as it does not inhibit the reaction and allows the starting material to be dissolved therein to a certain extent. Preferable examples of the solvent include tetrahydrofuran, ether, toluene and dichloromethane.

Step 3-4:

This step is a step of obtaining the compound (I-a) by deprotection reaction of the t-butoxycarbonyl group of the compound (3-6).

The reaction can be performed under the same conditions as those generally used in deprotection reaction of a t-butoxycarbonyl group such as the conditions described in a document such as T. W. Green and P. G. M. Wuts, "Protective Groups in Organic Chemistry, Second Edition", John Wiley & Sons (1991), P. 327-330. The compound (I-a) can be obtained by reacting trifluoroacetic acid with the compound (3-6) in a solvent such as dichloromethane, for example.

4. General Preparation Method 4:

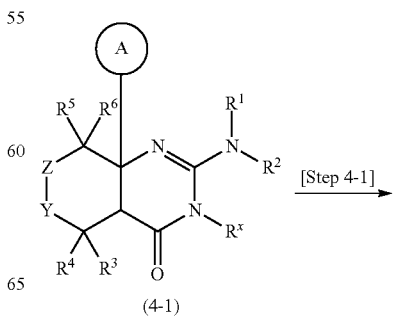

(4-1) [Step 4-1]

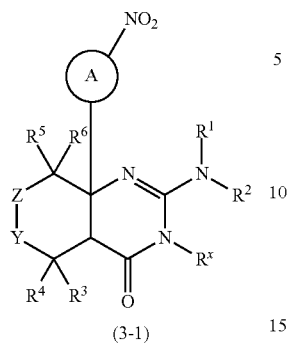

(3-1)

In the formula, Ring A, $R^1$, $R^2$, $R^3$, $R^4$, $R^5$, $R^6$, $R^x$, Y and Z are as defined above.

General Preparation Method 4 is a method for preparing a compound of the general formula (3-1) which is a synthetic intermediate of the compound according to the present invention and is used in General Preparation Method 3 from a compound (4-1) as a raw material through Step 4-1.

The compound (4-1) can be prepared from a commercially available product by General Preparation Method 5, and can also be prepared by a method described in Preparation Examples among Examples.

Step 4-1:

This step is a step of obtaining the compound (3-1) by nitration reaction of the compound (4-1). In this nitration reaction, the compound (3-1) can be obtained from the compound (4-1) by a method known to a person skilled in the art. Examples of the nitrating agent used in the reaction include concentrated nitric acid, potassium nitrate/concentrated sulfuric acid and fuming nitric acid/acetic anhydride. The reaction temperature is not particularly limited and is usually −20° C. to 50° C. Typically the reaction may be conducted at room temperature or 50° C.

It will be appreciated by those skilled in the art that the transformation of a compound of formula (4-1) to a compound of formula (3-1) may also be conducted on a compound of formula (4-1) where $R^1$ and/or $R^2$ are a protecting group, for example tert-butoxycarbonyl. It will also be appreciated by those skilled in the art that if $R^1$ and/or $R^2$ are a protecting group, for example, tert-butoxycarbonyl, that certain conditions employed in Step 4-1 may or may not also result in the aforementioned chemical transformation in addition to the concomitant deprotection of the protecting group.

5. General Preparation Method 5:

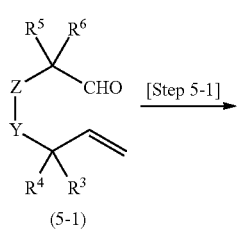

(5-1)

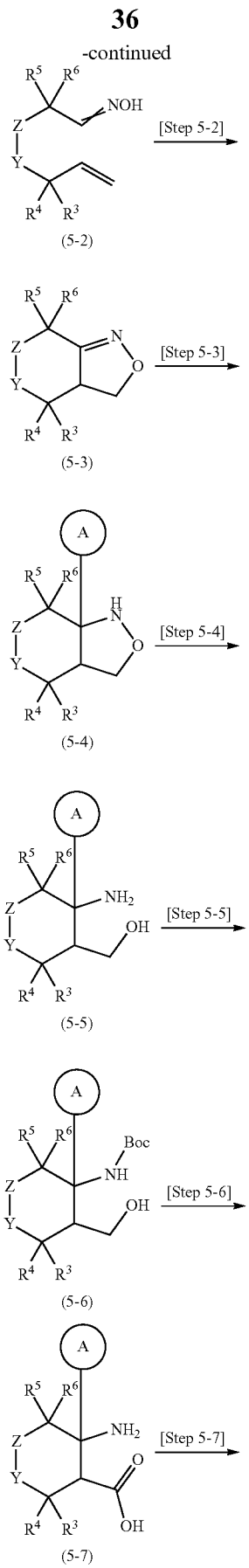

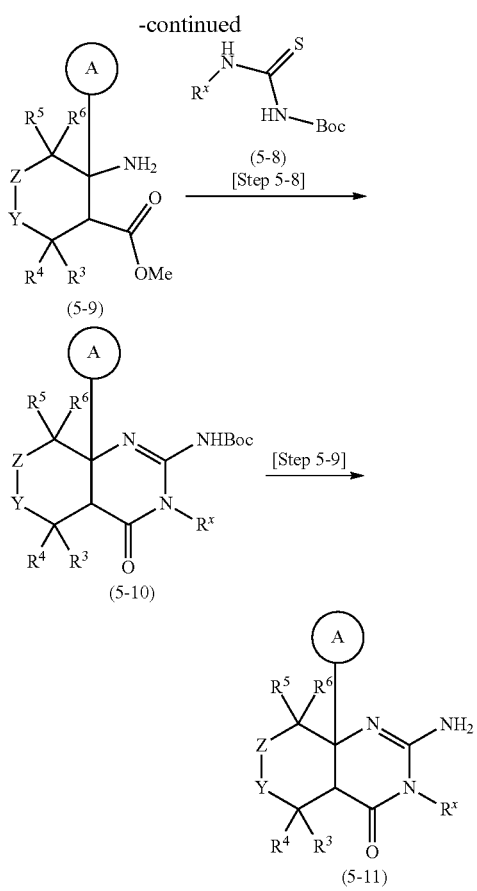

In the formula, Prt represents a protecting group such as a benzoyl group, an acetyl group or a 8-fluorenemethyloxycarbonyl group (Fmoc group), and Ring A, $R^3$, $R^4$, $R^5$, $R^6$, $R^x$, Y and Z are as defined above.

General Preparation Method 5 is a method for preparing a compound (5-10) which is a synthetic intermediate of the compound (I) according to the present invention from a compound (5-1) as a raw material through multiple steps of Step 5-1 to Step 5-8.

The compound (5-1) can be prepared from a commercially available product by the later-described General Preparation Method 6 or 7, can also be prepared from a commercially available product by a method known to a person skilled in the art, and can further be prepared by a method described in Preparation Examples among Examples.

Step 5-1:

This step is a step of obtaining a compound (5-2) by oximation of the compound (5-1).

The reaction in this step can be performed under the same conditions as those usually used in oximation reaction of a carbonyl compound such as the conditions described in Org. Lett. 9 (2007) 5, 753-756, Tetrahedron: Asymmetry 5 (1994) 6, 1018-1028 and Tetrahedron 54 (1998) 22, 5868-5882.

Specifically, the compound (5-2) can be obtained by reacting the compound (5-1) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 5-2:

This step is a step of obtaining a compound (5-3) by converting the compound (5-2) to a nitrile oxide derivative and performing 1,3-dipolar cycloaddition reaction with the olefin moiety in the same molecule.

The reaction in this step can be performed under the same conditions as those usually used in 1,3-dipolar cycloaddition reaction such as the conditions described in a document such as Org. Lett. 9 (2007) 5, 753-756, Tetrahedron: Asymmetry 5 (1994) 6, 1018-1028 and Tetrahedron 54 (1998) 22, 5868-5882. Examples of the reagent for converting the oxime compound to the nitrile oxide include N-chlorosuccinimide and sodium hypochlorite. The solvent used in this reaction is not particularly limited insofar as it does not inhibit the reaction. Preferable examples of the solvent include dichloromethane, chloroform, benzene, toluene, xylene, N,N-dimethylformamide, tetrahydrofuran and 1,4-dioxane. The reaction temperature is not particularly limited and is usually ice-cold temperature to solvent reflux temperature. The reaction time is not particularly limited and is usually 0.5 to 48 hours, and preferably 0.5 to 24 hours.

A more preferable result such as an improved yield may be achieved by carrying out this reaction in the presence of a base. Such a base is not particularly limited. Examples of the base include bases such as sodium carbonate, potassium carbonate, cesium carbonate, potassium phosphate and solutions thereof, and triethylamine and pyridine.

Step 5-3:

This step is a step of obtaining a compound (5-4) by addition reaction of an aryllithium reagent (including heterocyclic) or a Grignard reagent (including heterocyclic) with the compound (5-3).

The reaction in this step can be performed under the same conditions as those described in J. Am. Chem. Soc. 2005, 127, 5376-5383, Bull. Chem. Soc. Jpn., 66, 2730-2737 (1993) and SYNLETT. 2004, No. 8, pp 1408-1413, for example.

The aryllithium reagent (including heterocyclic) or the Grignard reagent (including heterocyclic) can be prepared by a method known to a person skilled in the art. Specifically, a corresponding aryl (including heterocyclic) lithium reagent or aryl (including heterocyclic) magnesium reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to minimize formation of a by-product.

Favorable results such as an improved yield and a reduced reaction time may be achieved by addition of TMEDA (tetramethylethylenediamine), HMPA (hexamethylphosphoramide) or a Lewis acid such as a boron trifluoride-diethyl ether complex ($BF_3.OEt_2$) as an additive, for example.

Step 5-4:

This step is a step of obtaining a compound (5-5) by subjecting the compound (5-4) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 7 (2005) 25, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry 5 (1994) 6, 1018-1028 and Tetrahedron, Vol. 53, No. 16, pp 5752-5746, 1997, for example. The compound (5-5) can be obtained by hydrogenating the compound (5-4) using platinum oxide as a catalyst in a solvent such as methanol, for example.

The reaction using lithium aluminum hydride can be performed under the same conditions as those described in Bull. Chem. Soc. Jpn., 66, 2730-2737 (1993), for example. The compound (5-5) can be obtained by reducing the compound (5-4) using lithium aluminum hydride in a solvent such as ether, for example.

Step 5-5:

Same as step 3-1

Step 5-6:

This step is a method of obtaining a compound (5-7) by oxidizing the compound (5-6).

The carboxylic acid compound can be obtained from the alcohol by a method known to a person skilled in the art.

Examples of the known oxidation method used in the reaction include PDC oxidation, Jones reagent, potassium permanganate or sodium chlorite.

The solvent used in the reaction is not particularly limited insofar as it does not inhibit the reaction and allows the starting material to be dissolved therein to a certain extent. Examples of the solvent include DMF, water, acetonitrile, acetone and THF. It will be appreciated by those skilled in the art that certain oxidation conditions may result in concomitant deprotection, for example deprotection of the Boc group may occur when Jones reagent is used due to the presence of a strong acid, for example sulfuric acid. It will be appreciated by those skilled in the art that simultaneous deprotection may or may not be desirable and that the conditions for this transformation may be selected to avoid this if required.

Step 5-7:

This step is a method of converting a carboxylic acid to an ester. This transformation is known to those skilled in the art. Examples of the conditions include heating in an alcohol in the presence of an acid catalyst, for example, methanol with concentrated sulfuric acid.

Step 5-8

This step is a method of obtaining compound (5-10) by condensing the compound (5-8) with compound (5-9) and then cyclizing the resultant compound.

The condensation and cyclisation can be performed by treating with a coupling reagent such as EDCI. The solvent used in the reaction is not particularly limited insofar as it does not inhibit the reaction and allows the starting material to be dissolved therein to a certain extent. Examples of the solvent include DMF, dichloromethane, acetonitrile, and THF.

Step 5-9

This step is a step of obtaining compound (5-11) deprotection reaction of the t-butoxycarbonyl group of the compound (5-10). This reaction can be performed using a method described in the above preparation method ((Step 3-4).

6. General Preparation Method 6:

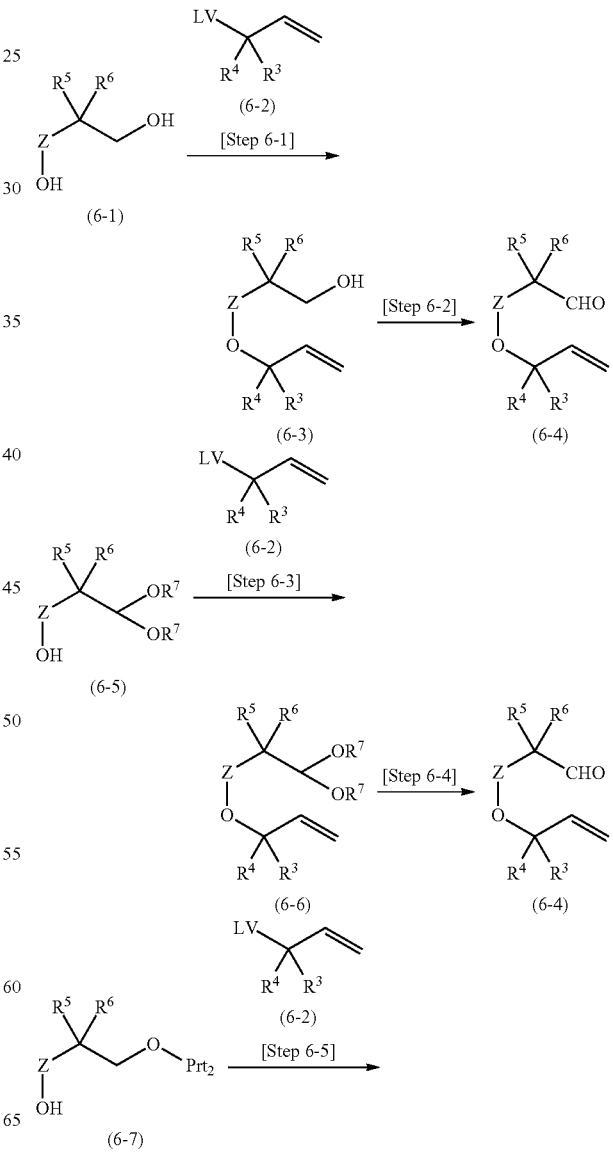

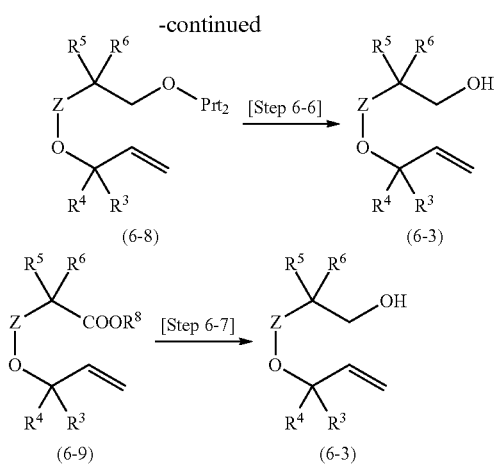

In the formula, $Prt_2$ represents a primary hydroxyl protecting group, $R^8$ represents a $C_{1-6}$ alkyl group, and $Z$, $R^3$, $R^4$, $R^5$, $R^6$, $R^7$ and LV are as defined above.

General Preparation Method 6 is a method for preparing a compound (6-4) which is a compound (5-1) as a starting material for General Preparation Method 5, wherein Y is an oxygen atom.

Compounds (6-1), (6-2), (6-5), (6-7) and (6-9) each can be a commercially available product used as is, can also be prepared from a commercially available product by a method known to a person skilled in the art, and can further be prepared by a method described in Preparation Examples among Examples.

Step 6-1:

This step is a step of obtaining a compound (6-3) by reaction of the compound (6-1) with the compound (6-2).

This reaction can be performed under the same conditions as those usually used in O-alkylation reaction of an alcohol compound (such as the conditions described in Tetrahedron Lett. 46 (2005) 45, 7751-7755). In this reaction, the compound (6-3) can be obtained by adding a base such as sodium hydride to a solution of the compound (6-1) in THF to prepare an alkoxide, and then reacting the alkoxide with the compound (6-2), for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Step 6-2:

This step is a step of obtaining an aldehyde compound (6-4) by subjecting the alcohol compound (6-3) to oxidation reaction. The aldehyde compound can be obtained from the alcohol compound by a method known to a person skilled in the art.

Examples of the known oxidation method used in the reaction include Swern oxidation, Corey-Kim oxidation, Moffatt oxidation, PCC oxidation, PDC oxidation, Dess-Martin oxidation, $SO_3$-pyridine oxidation and TEMPO oxidation.

The solvent used in the reaction is not particularly limited insofar as it does not inhibit the reaction and allows the starting material to be dissolved therein to a certain extent. Examples of the solvent include dimethyl sulfoxide, tetrahydrofuran, toluene, dichloromethane and chloroform.

The reaction temperature is not particularly limited and is usually −78° C. to solvent reflux temperature, and preferably −78° C. to room temperature. The reaction time is not particularly limited and is usually 0.5 to 48 hours, and preferably 0.5 to 24 hours.

Step 6-3:

This step is a step of synthesizing a compound (6-6) from the compound (6-5) as a raw material using a method described in the above preparation method (Step 6-1).

Step 6-4:

This step is a step of obtaining the compound (6-4) by deprotecting the acetal group of the compound (6-6).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

Step 6-5:

This step is a step of synthesizing a compound (6-8) from the compound (6-7) as a raw material using a method described in the above preparation method (Step 6-1).

Step 6-6:

This step is a step of obtaining the compound (6-3) by deprotecting the hydroxyl protecting group of the compound (6-8). The hydroxyl protecting group used in this step is not particularly limited.

This reaction can be performed under the same conditions as those generally used in deprotection of an alcohol protecting group such as the conditions described in a document such as T. W. Green and P. G. M. Wuts, "Protective Groups in Organic Chemistry, Third Edition", John Wiley & Sons, P. 17-245.

Step 6-7:

This step is a step of synthesizing the compound (6-3) from the compound (6-9) as a raw material This transformation can be conducted by several methods by those skilled in the art, for example, by reduction with a reagent such as $NaBH_4$, $LiEt_3BH$, $LiAlH_4$ and the like. The choice of solvent is not particularly limited and includes DMF, THF, $Et_2O$ and the like. Selection of reaction conditions will be appreciated by those skilled in the art.

7. General Preparation Method 7:

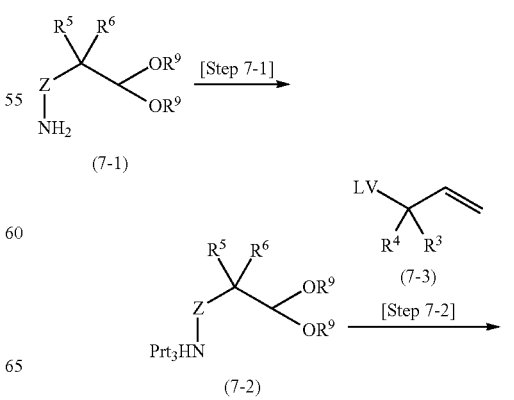

43

-continued

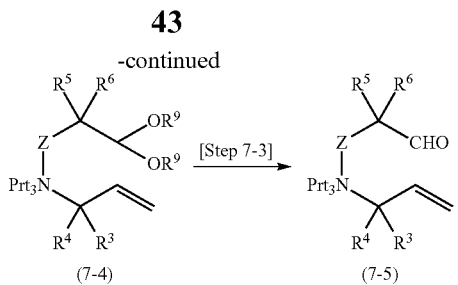

In the formula, $R^9$ represents a $C_{1-6}$ alkyl group, or two $R^9$ together may form a ring, $Prt_3$ represents a protecting group such as a 2,4-dimethoxybenzyl group, and Z, $R^3$, $R^4$, $R^5$, $R^6$, Z and LV are as defined above.

General Preparation Method 7 is a method for preparing a compound (7-5) which is a compound (5-1) as a starting material for General Preparation Method 5, wherein Y is a nitrogen atom.

Compounds (7-1) and (7-3) each can be a commercially available product used as is, can also be prepared from a commercially available product by a method known to a person skilled in the art, and can further be prepared by a method described in Preparation Examples among Examples.

Step 7-1:

This step is a step of obtaining a compound (7-2) by protecting the amino group of the compound (7-1).

This reaction can be performed under the same conditions as those generally used in protection of an amino group such as the conditions described in a document such as T. W. Green and P. G. M. Wuts, "Protective Groups in Organic Chemistry, Third Edition", John Wiley & Sons, P. 494-572 and J. Med. Chem. 2007, 50, 5493-5508.

Step 7-2:

This step is a step of obtaining a compound (7-4) by N-alkylation reaction of the compound (7-2) with the compound (7-3).

This reaction can be performed under the same conditions as those usually used in N-alkylation reaction of a compound (7-2) (such as the conditions described in J. Med. Chem. 2007, 50, 5493-5508). In this reaction, the compound (7-4) can be obtained by adding a base such as powdery sodium hydroxide to a solution of the compound (7-2) in toluene, and then reacting the mixture with the compound (7-3), for example. The solvent used in the reaction is not particularly limited insofar as it does not inhibit the reaction and allows the starting material to be dissolved therein to a certain extent. Examples of the solvent include solvents such as toluene, THF, DMF and dimethyl sulfoxide. The reaction can be performed by causing 1 to 5 equivalents of an appropriate base to act in the presence of such a solvent. Examples of the base used include sodium hydroxide, potassium hydroxide, sodium hydride, potassium hydride and t-butoxypotassium. The reaction time is not particularly limited and is usually 0.5 to 72 hours, and preferably 0.5 to 24 hours. The reaction temperature is usually −20° C. to 100° C.

A more preferable result such as an improved yield may be achieved by adding a salt such as tetrabutylammonium iodide in this reaction.

Step 7-3:

This step is a step of obtaining the compound (7-5) by deprotecting the acetal group of the compound (7-4).

This reaction can be performed under the same conditions as those generally used in deprotection of an aldehyde group such as the conditions described in a document such as T. W. Green and P. G. M. Wuts, "Protective Groups in Organic Chemistry, Third Edition", John Wiley & Sons, P. 293-329.

44

8. General Preparation Method 8:

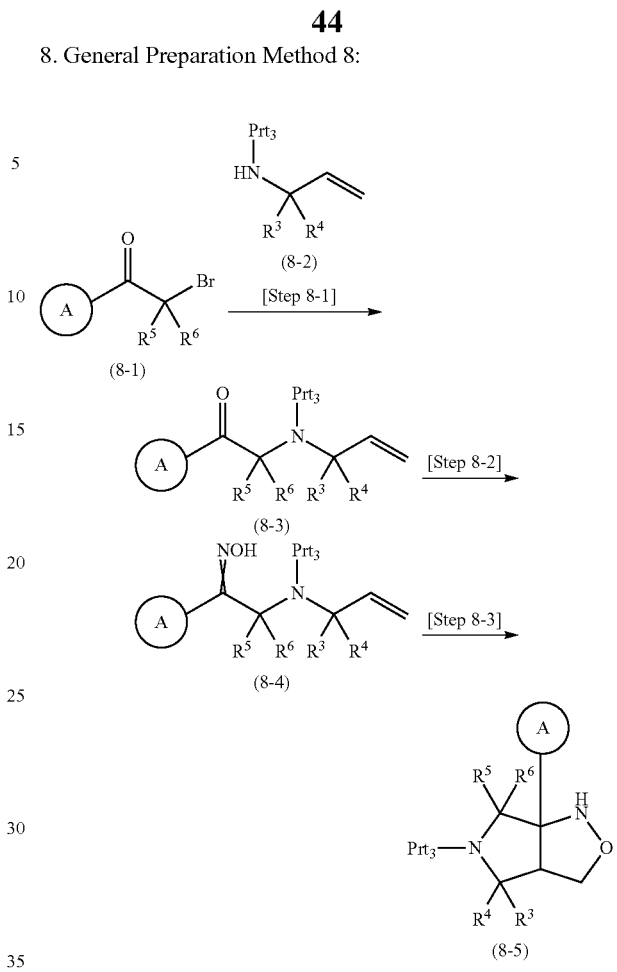

In the formula, Prt represents a protecting group such as a benzoyl group, an acetyl group or a 8-fluorenemethyloxycarbonyl group (Fmoc group), $Prt_3$ represents a protecting group such as a 2,4-dimethoxybenzyl group, and Ring A, $R^3$, $R^4$, $R^5$ and $R^6$ are as defined above.

General Preparation Method 8 is steps of the method for preparing compounds of the general formula (8-5) which are synthetic intermediates of the compound (I) according to the present invention in General Preparation Method 5, wherein Y is a nitrogen atom and Z is a single bond. These compounds can be prepared from a compound (8-1) as a raw material by the steps shown above.

The compound (8-1) can be a commercially available product used as is, can also be prepared from a commercially available product by a method known to a person skilled in the art, and can further be prepared by a method described in Preparation Examples among Examples. A compound (8-2) can be prepared from a commercially available product by a method known to a person skilled in the art, and can further be prepared by a method described in Preparation Examples among Examples.

Step 8-1:

This step is a step of obtaining a compound (8-3) by reaction of the compound (8-1) with the compound (8-2). This reaction can be performed under the same conditions as those usually used in N-alkylation reaction of an amino compound (such as the conditions described in J. Med. Chem. 2002, 45, 3794-3804 and J. Med. Chem. 2000, 43, 3808-3812). In this reaction, the compound (8-3) can be obtained by reacting the compound (8-1) with the compound (8-2) in a solvent such as dichloromethane in the presence of a base such as N,N-diisopropylethylamine, for example. The solvent used in the reaction is not particularly limited insofar as it does not inhibit the reaction and allows the starting material to be dissolved therein to a certain extent. Examples of the solvent include dichloromethane, THF, acetonitrile and DMF. The reaction can be performed by causing 1 to 10 equivalents of an appropriate base to act in such a solvent. Examples of the base used include N,N-diisopropylethylamine, triethylamine, sodium carbonate and potassium carbonate. The reaction time is not particularly limited and is usually 0.5 to 72 hours, and preferably 0.5 to 12 hours. The reaction temperature is usually ice-cold temperature to 50° C.

Step 8-2:

This step is a step of obtaining a compound (8-4) by oximation of the compound (8-3).

The reaction in this step can be performed under the same conditions as those usually used in oximation reaction of a carbonyl compound such as the conditions described in J. Med. Chem. 2002, 45, 3794-3804 and J. Med. Chem. 2000, 43, 3808-3812.

Specifically, the compound (8-4) can be obtained by reacting the compound (8-3) with hydroxylamine or a hydroxylamine salt (such as hydroxylamine hydrochloride or hydroxylamine sulfate) in the presence of a base or in the absence of a base, for example. The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium carbonate, potassium carbonate, sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Step 8-3:

This step is a step of obtaining a compound (8-5) which is the equivalent to compound (5-4) by subjecting the oxime compound (8-4) to 1,3-dipolar cycloaddition reaction.

The reaction in this step can be performed under the same conditions as those usually used in 1,3-dipolar cycloaddition reaction such as the conditions described in J. Org. Chem. 1993, 58, 4538-4546 and Tetrahedron Letters, Vol. 29, No. 41, pp 5312-5316.

Specifically, the compound (8-5) can be obtained by heating the compound (8-4) under reflux in a toluene solvent, for example. The solvent used in this reaction is not particularly limited insofar as it does not inhibit the reaction. Preferable examples of the solvent include organic solvents such as toluene, xylene and chlorobenzene. The reaction time is not particularly limited and is usually 5 minutes to 24 hours, and preferably 5 minutes to 12 hours. The reaction temperature is usually 0° C. to solvent reflux temperature, and more preferably room temperature to solvent reflux temperature.

Favorable results such as an improved yield and a reduced reaction time may be achieved by addition of a Lewis acid such as zinc chloride as an additive, for example.

Favorable results such as a reduced reaction time and an improved yield may be obtained by performing this reaction using a microwave reactor.

9. General Preparation Method 9:

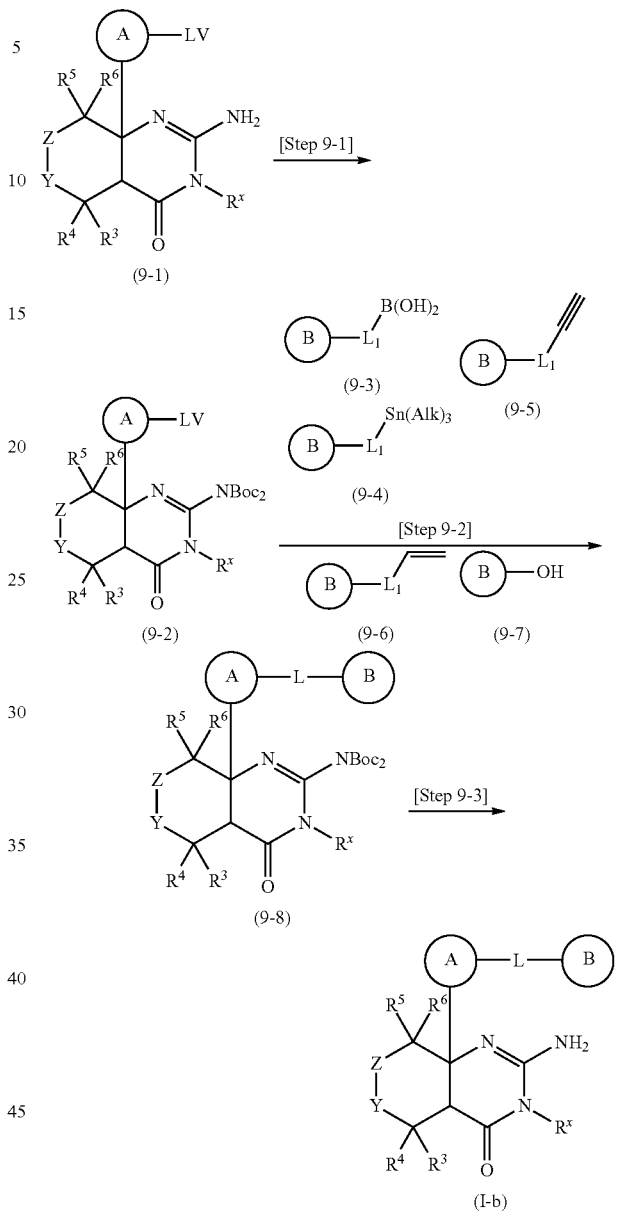

In the formula, $L_1$ represents a single bond or a $C_{1-6}$ alkylene group in compounds (9-3) and (9-4) and represents a single bond or a $C_{1-4}$ alkylene group in compounds (9-5) and (9-6), L represents a single bond, an oxygen atom, a $C_{1-6}$ alkylene group, a $C_{2-6}$ alkenylene group or a $C_{2-6}$ alkynylene group, Alk represents a $C_{1-6}$ alkyl group, and Ring A, Ring B, $R^3$, $R^4$, $R^5$, $R^6$, $R^x$, Y, Z and LV are as defined above.

General Preparation Method 9 is a method for preparing the compound (I-b) of the general formula (I) according to the present invention, wherein L is a single bond, an oxygen atom, a $C_{1-6}$ alkylene group, a $C_{2-6}$ alkenylene group or a $C_{2-6}$ alkynylene group and $R^1$ and $R^2$ are hydrogen atoms, from a compound (9-1) as a raw material by the above steps.

The compound (9-1) can be prepared from a commercially available product by General Preparation Method 5, and can also be prepared by a method described in Preparation Examples among Examples. The compounds (9-3), (9-4), (9-5), (9-6) and (9-7) each can be a commercially available product used as is, can also be prepared from a commercially available product by a method known to a person skilled in the art, and can further be prepared by a method described in Preparation Examples among Examples.

Step 9-1:

This step is a step of obtaining a compound (9-2) by di-t-butoxycarbonylating the compound (9-1). This reaction can be performed under the same conditions as those generally used in t-butoxycarbonylation of an amide compound such as the conditions described in T. W. Green and P. G. M. Wuts, "Protective Groups in Organic Chemistry, Third Edition", John Wiley & Sons, P. 642-643 and J. Org. Chem. 2005, 70, 2445-2454. The compound (9-2) can be obtained by reacting the compound (9-1) with di-tert-butyl dicarbonate using 4-dimethylaminopyridine as a base in a solvent such as THF, for example.

The solvent used in this reaction is not particularly limited insofar as it does not inhibit the reaction. Preferable examples of the solvent include organic solvents such as tetrahydrofuran, 1,4-dioxane, 1,2-dimethoxyethane, dichloromethane, DMF and acetonitrile, and mixed solvents thereof. Examples of the base used include triethylamine, 4-dimethylaminopyridine, DBU and mixtures thereof. A catalytic amount to an excess of, and more preferably 0.1 to 5 equivalents of the base is used with respect to the compound (9-1). Two equivalents to an excess of, and more preferably 2 to 10 equivalents of di-tert-butyl dicarbonate is used with respect to the compound (9-1). The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step 9-2:

This step is a step of obtaining a compound (9-8) by coupling reaction of the compound (9-2) with the compound (9-3), (9-4), (9-5), (9-6) or (9-7) using a transition metal. This reaction can be performed under the conditions usually used in coupling reaction using a transition metal (such as Suzuki-Miyaura reaction, Stille reaction, Sonogashira reaction, Heck reaction or aryl ether synthesis reaction of Buchwald et al.).

Examples of the Suzuki-Miyaura reaction include reactions in documents such as J. Org. Chem. 2007, 72, 7207-7213, J. Am. Chem. Soc. 2000, 122, 4020-4028 and J. Org. Chem. 2007, 72, 5960-5967. Examples of the Stille coupling reaction include reaction in a document such as J. Am. Chem. Soc. 1990, 112, 3093-3100. Examples of the Sonogashira reaction include reactions in documents such as J. Org. Chem. 2007, 72, 8547-8550 and J. Org. Chem. 2008, 73, 234-240. Examples of the Heck reaction include reaction in a document such as J. Am. Chem. Soc. 2005, 127, 16900-16911. Examples of the aryl ether synthesis reaction of Buchwald et al. include reaction in a document such as Buchwald, S. L. et al., J Am Chem Soc (1999) 121 (18), 4369-4378. The organometallic catalyst used in this reaction is not particularly limited. Preferable examples of the organometallic catalyst include metal catalysts such as tetrakis(triphenylphosphine)palladium (0), dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II), and mixtures of these metal catalysts. The amount of the organometallic catalyst used is about 0.001 to 0.5 equivalent with respect to the raw material. The amount of the compound (9-3), (9-4), (9-5), (9-6) or (9-7) used is not particularly limited and is usually 1 to 5 equivalents with respect to the compound (9-2). The solvent used in this reaction is not particularly limited insofar as it does not inhibit the reaction. Preferable examples of the solvent include benzene, toluene, xylene, N,N-dimethylformamide, 1-methyl-2-pyrrolidone, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 48 hours, and preferably 0.5 to 24 hours.

A more preferable result such as an improved yield may be achieved by carrying out this reaction in the presence of a base or a salt. Such a base or salt is not particularly limited. Preferable examples of the base or salt include bases or salts such as sodium carbonate, potassium carbonate, barium hydroxide, cesium carbonate, potassium phosphate, potassium fluoride and solutions thereof, and triethylamine, N,N-diisopropylethylamine, lithium chloride and copper (I) iodide.

Step 9-3:

This step is a step of synthesizing the compound (I-b) from the compound (9-8) as a raw material using a method described in the above preparation method (Step 3-4).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 9 with a corresponding halide compound such as a $C_{1-6}$ alkyl halide.

10. General Preparation Method 10:

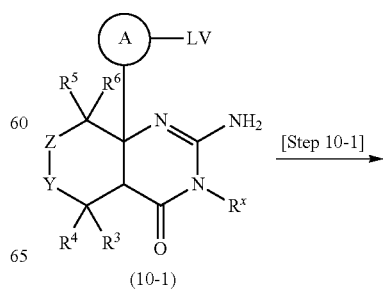

(10-1)

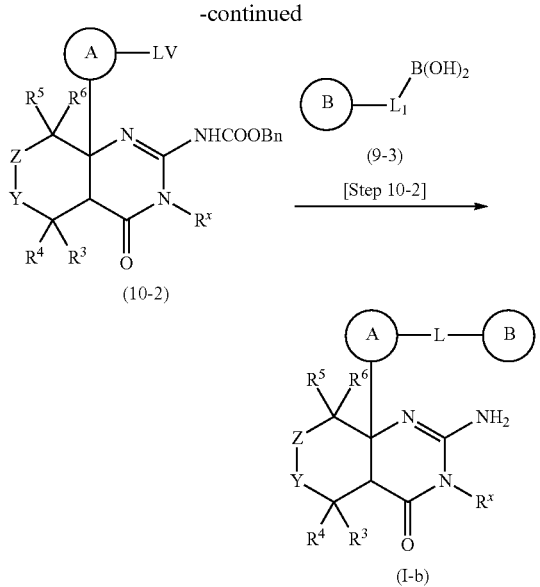

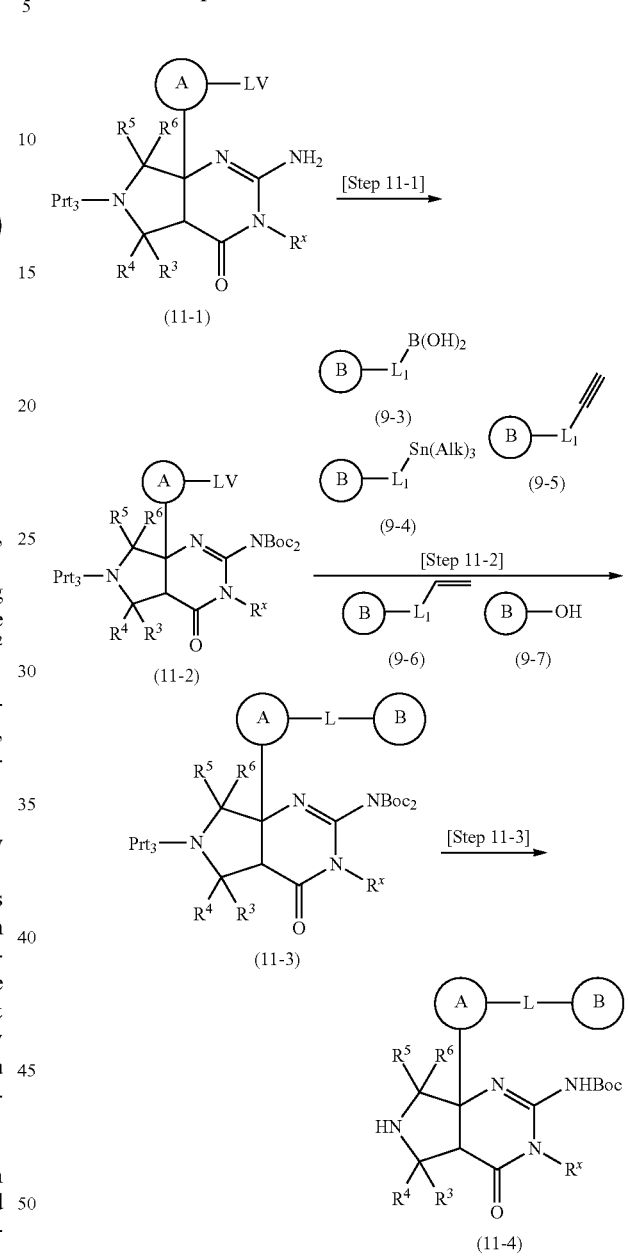

In the formula, Ring A, Ring B, $R^3$, $R^4$, $R^5$, $R^6$, $R^x$, Z, Y, $L_1$, L and LV are as defined above.

General Preparation Method 10 is a method for preparing the compound (I-b) of the general formula (I) according to the present invention, wherein L is a single bond and $R^1$ and $R^2$ are hydrogen atoms, from a compound (10-1).

The compound (10-1) can be prepared from a commercially available product by General Preparation Method 5, and can also be prepared by a method described in Preparation Examples among Examples.

Step 10-1:

This step is a step of obtaining a compound (10-2) by benzyloxycarbonylation of the compound (10-1).

The reaction can be performed under the same conditions as those generally used in benzyloxycarbonylation of an amino compound such as the conditions described in a document such as T. W. Green and P. G. M. Wuts, "Protective Groups in Organic Chemistry, Third Edition", John Wiley & Sons, P. 531-537. The compound (10-2) can be obtained by reacting the compound (10-1) with benzyl chloroformate in a mixed solvent of 1,4-dioxane and a saturated sodium bicarbonate solution, for example.

Step 10-2:

This step is a step of synthesizing the compound (I-b) from the compound (10-2) as a raw material using the same method as Suzuki-Miyaura reaction described in the above preparation method (Step 9-2).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 10 with a corresponding halide compound such as a $C_{1-6}$ alkyl halide.

11. General Preparation Method 11:

In the formula, Ring A, Ring B, $R^3$, $R^4$, $R^5$, $R^6$, $R^x$, $L_1$, L, LV, Alk and $Prt_3$ are as defined above.

General Preparation Method 11 shows General Preparation Method 9 in the case where Y is a nitrogen atom and Z is a single bond in the general formula. The method is a method for preparing a compound (11-4) which is a synthetic intermediate of the compound (I) according to the present invention from a compound (11-1).

The compound (11-1) can be prepared from a commercially available product by General Preparation Method 5 or a combination of General Preparation Methods 5 and 7 or 5 and 8, and can also be prepared by a method described in Preparation Examples among Examples.

Step 11-1:

This step is a step of synthesizing a compound (11-2) from the compound (11-1) as a raw material using a method described in the above preparation method (Step 9-1).

Step 11-2:

This step is a step of synthesizing a compound (11-3) from the compound (11-2) as a raw material using a method described in the above preparation method (Step 9-2).

Step 11-3:

This step is a step of obtaining the compound (11-4) by deprotecting the amino group of the compound (11-3). The amino protecting group used in this step is not particularly limited. When $Prt_3$ is a 2,4-dimethoxybenzyl group, for example, this step can be performed under the same conditions as those generally used (such as the conditions described in a document such as Tetrahedron Vol. 47, No. 26, pp 4591-4602, 1991). In this step, when $Prt_3$ is a 2,4-dimethoxybenzyl group, one Boc group can be deprotected simultaneously with deprotection of the 2,4-dimethoxybenzyl group. When $Prt_3$ is a 2,4-dimethoxybenzyl group in this step, the solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

12. General Preparation Method 12:

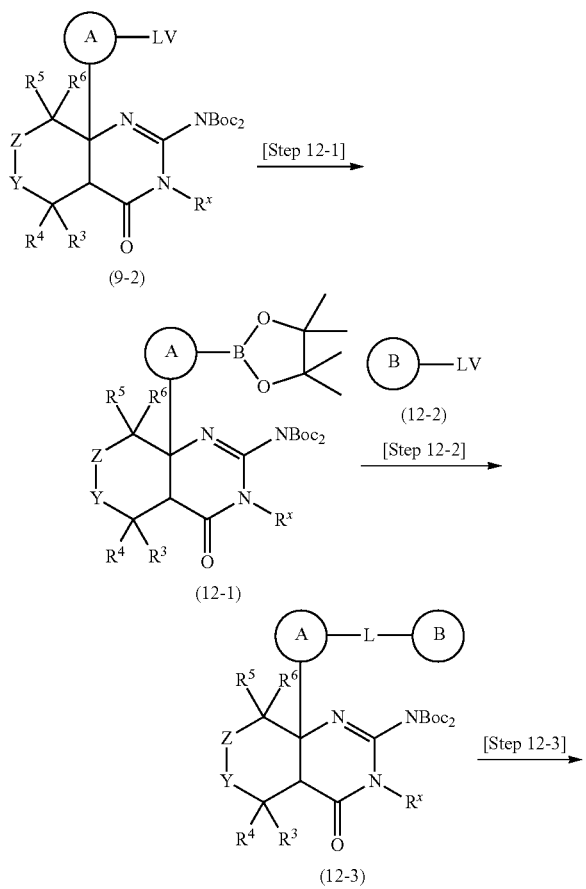

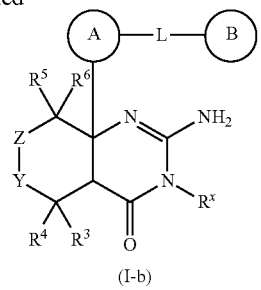

In the formula, Ring A, Ring B, $R^3$, $R^4$, $R^5$, $R^6$, $R^x$, Y, Z, L and LV are as defined above.

General Preparation Method 12 is a method for preparing the compound (I-b) of the general formula (I) according to the present invention, wherein L is a single bond and $R^1$ and $R^2$ are hydrogen atoms, from a compound (9-2).

The compound (9-2) can be prepared from a commercially available product by General Preparation Method 9, and can also be prepared by a method described in Preparation Examples among Examples. A compound (12-2) can be a commercially available product used as is, can also be prepared from a commercially available product by a method known to a person skilled in the art, and can further be prepared by a method described in Preparation Examples among Examples.

Step 12-1:

This step is a step of obtaining a compound (12-1) by coupling reaction of the compound (9-2) using a transition metal.

The reaction in this step can be performed under the same conditions as those usually used in coupling reaction using a transition metal such as the conditions described in Org. Lett. 2007, Vol. 9, No. 4, 558-562 and Bioorg. Med. Chem, 14 (2006) 4944-4957. Specifically, the compound (12-1) can be obtained by reacting the compound (9-2) with bis(pinacolato)diborane under heating conditions in a solvent such as DMF in the presence of a catalyst such as potassium acetate or [1,1'-bis(diphenylphosphino)ferrocene]palladium (II) dichloride, for example.

The organometallic catalyst used in this reaction is not particularly limited. Preferable examples of the organometallic catalyst include metal catalysts such as dichlorobis(triphenylphosphine)palladium (II), [1,1'-bis(diphenylphosphino)ferrocene]palladium (II) dichloride, bis(tert-butylphosphine)palladium (0), palladium (II) acetate and [1,3-bis(diphenylphosphino)propane]nickel (II). The amount of the organometallic catalyst used is about 0.001 to 0.5 equivalent with respect to the raw material. The solvent used in this reaction is not particularly limited insofar as it does not inhibit the reaction. Preferable examples of the solvent include benzene, toluene, xylene, N,N-dimethylformamide, 1-methyl-2-pyrrolidone, dimethyl sulfoxide, tetrahydrofuran, 1,2-dimethoxyethane, 1,4-dioxane, acetonitrile and propionitrile. The reaction temperature is not particularly limited and is usually ice-cold temperature to solvent reflux temperature, and preferably room temperature to solvent reflux temperature, for example. The reaction time is not particularly limited and is usually 0.5 to 72 hours, and preferably 0.5 to 24 hours.

A more preferable result such as an improved yield may be achieved by carrying out this reaction in the presence of a base. Such a base is not particularly limited. Preferable examples of the base include bases such as potassium acetate, sodium acetate, sodium carbonate, potassium carbonate, cesium carbonate, potassium phosphate, potassium fluoride, triethylamine and N,N-diisopropylethylamine.

Step 12-2:

This step is a step of synthesizing a compound (12-3) from the compound (12-1) as a raw material using a method described in the above preparation method (Step 9-2).

Step 12-3:

This step is a step of synthesizing the compound (I-b) from the compound (12-3) as a raw material using a method described in the above preparation method (Step 3-4).

The compound of the formula (I) according to the present invention, wherein at least one of $R^1$ and $R^2$ is a $C_{1-6}$ alkyl group which may have 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-b) obtained in General Preparation Method 12 with a corresponding halide compound such as a $C_{1-6}$ alkyl halide.

13. General Preparation Method 13:

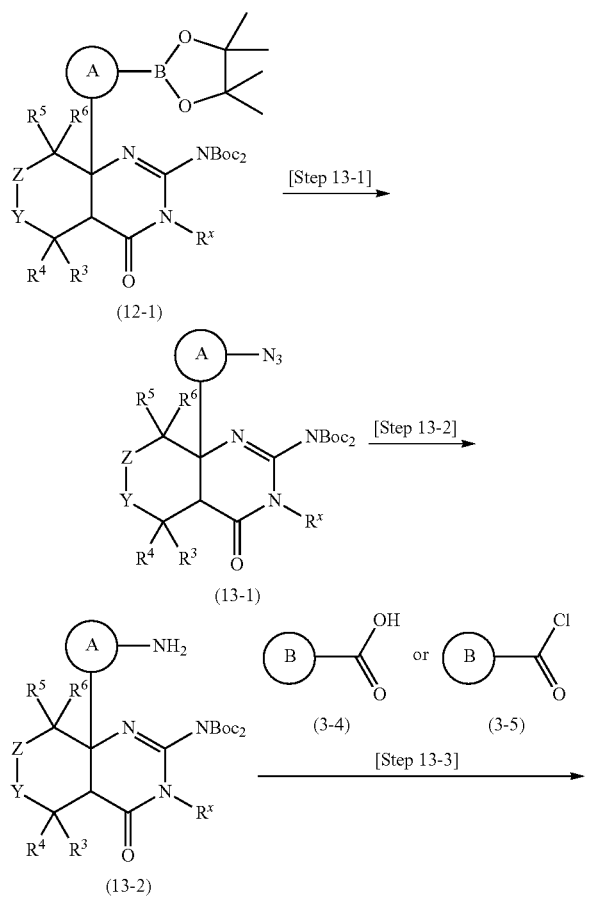

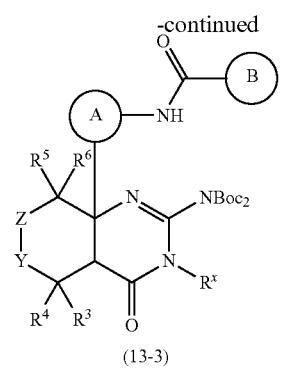

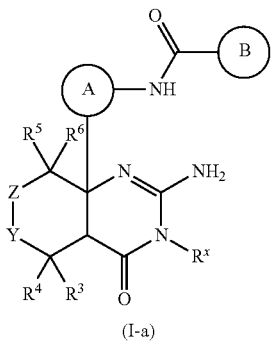

In the formula, Ring A, Ring B, $R^3$, $R^4$, $R^5$, $R^6$, $R^x$, Y and Z are as defined above.

General Preparation Method 13 is a method for preparing the compound (I-a) of the general formula (I) according to the present invention, wherein L is —NHCO— and $R^1$ and $R^2$ are hydrogen atoms, from a compound (12-1).

The compound (12-1) can be prepared from a commercially available product by General Preparation Method 12, and can also be prepared by a method described in Preparation Examples among Examples.

Step 13-1:

This step is a step of obtaining a compound (13-1) by reaction of the compound (12-1) with sodium azide in the presence of a copper catalyst.

The reaction in this step can be performed under the same conditions as those described in Org. Lett. 2007, Vol. 9, No. 5, 761-764 and Tetrahedron Lett. 2007, 48, 3525-3529, for example. Specifically, the compound (13-1) can be obtained by reacting the compound (12-1) with sodium azide at room temperature using a solvent such as methanol in the presence of a catalyst such as copper (II) acetate, for example.

The catalyst used in this reaction is not particularly limited. Preferable examples of the catalyst include metal catalysts such as copper (II) acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include methanol, N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

Step 13-2:

This step is a step of obtaining a compound (13-2) by reduction reaction the azide of the compound (13-1). The reaction in this step can be performed under the same conditions as those described in J. Org. Chem. 2003, 68, 4693-4699, for example. Specifically, the compound (13-2) can be obtained by dissolving the compound (13-1) in a solvent such as methanol, and reacting the solution with sodium borohydride, for example.

Step 13-3:

This step is a step of synthesizing a compound (13-3) from the compound (13-2) as a raw material using a method described in the above preparation method (Step 3-3).

Step 13-4:

This step is a step of synthesizing the compound (I-a) from the compound (13-3) as a raw material using a method described in the above preparation method (Step 3-4).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting the compound (I-a) obtained in General Preparation Method 13 with a corresponding halide compound such as a $C_{1-6}$ alkyl halide.

Alternatively, —NHCO— of L in the compound (I-a) of the present invention can be converted to —$NR^eCO$— (wherein $R^e$ is a $C_{1-6}$ alkyl group which optionally has 1 to 3 substituents selected from Substituent Group α) by further reacting the compound (I-a) obtained in General Preparation Method 13 with a corresponding halide compound such as a $C_{1-6}$ alkyl halide.

The compound of the formula (I) according to the present invention, wherein L is —$NR^eSO_2$—, can be obtained using a corresponding sulfonyl halide compound in place of the compound (3-4) or (3-5) used in General Preparation Method 13.

14. General Preparation Method 14:

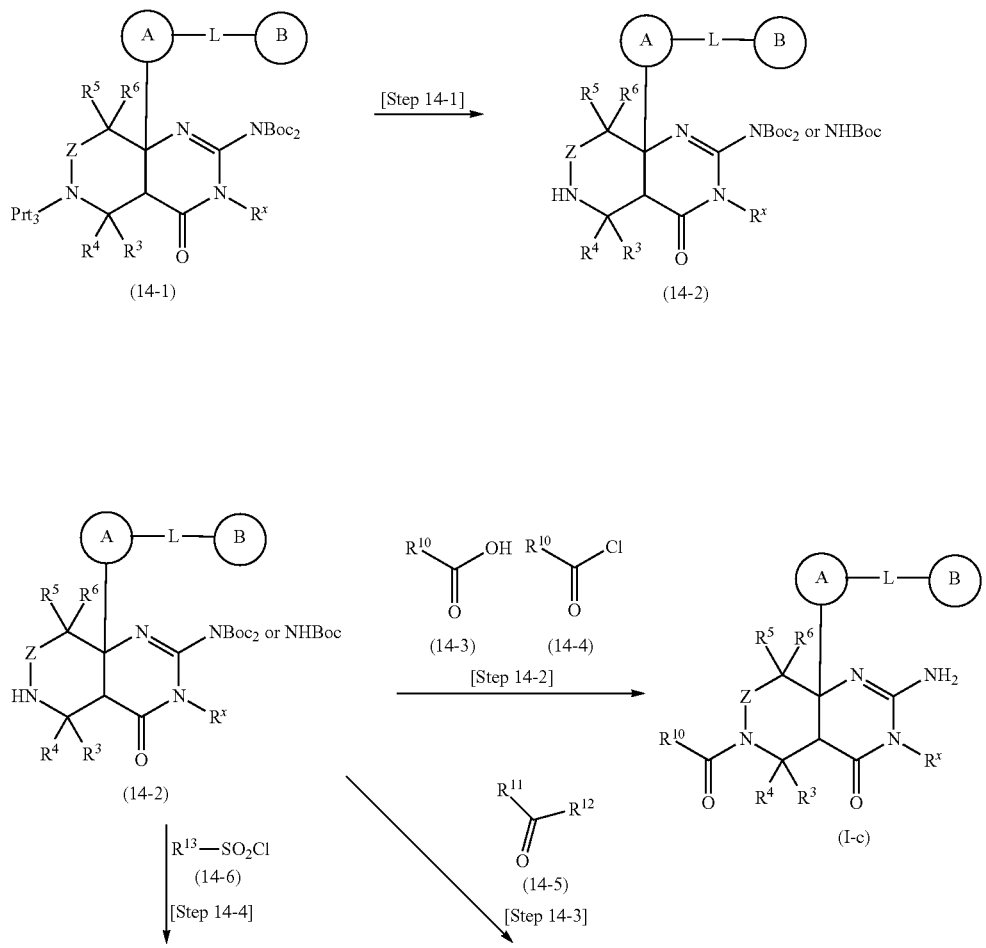

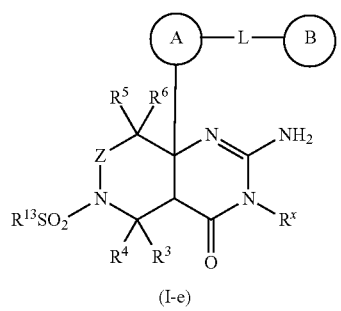
(I-e)
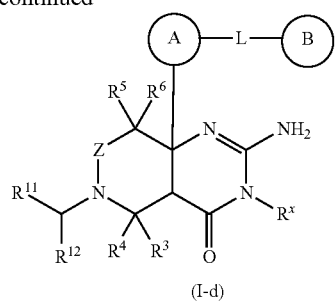
(I-d)
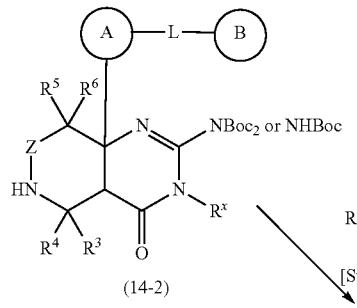
(14-2)
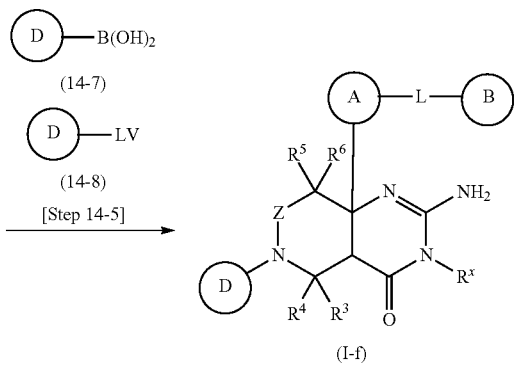
(I-f)
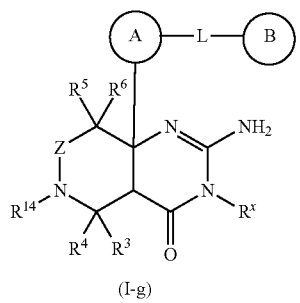
(I-g)
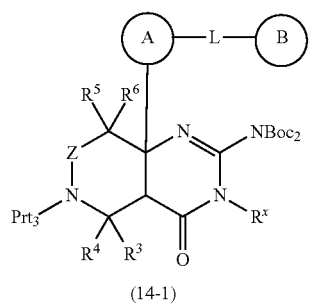
(14-1)
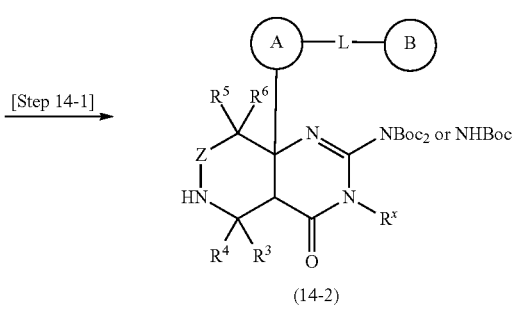
(14-2)
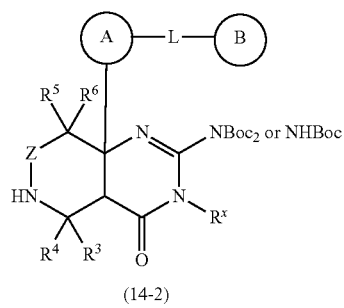
(14-2)
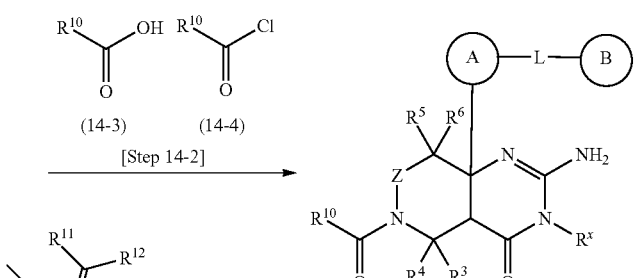
(I-c)
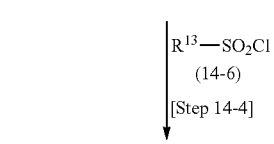
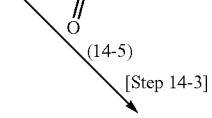

-continued

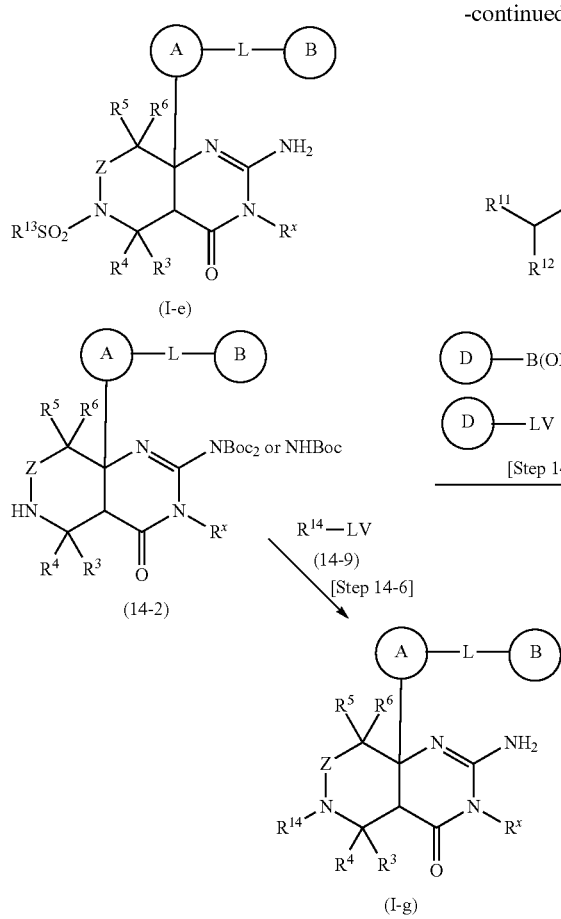

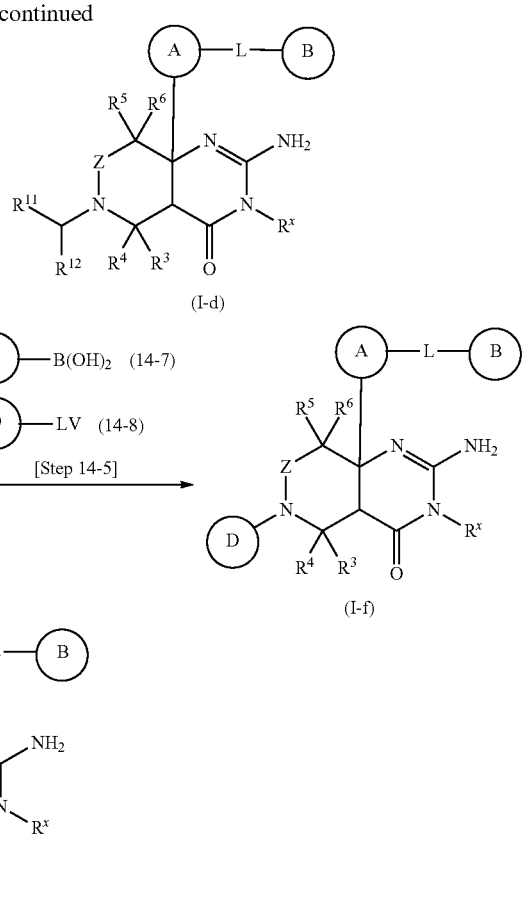

In the formula, Ring A, Ring B, $R^3$, $R^4$, $R^5$, $R^6$, $R^x$, L, Z, $Prt_3$ and LV are as defined above; Ring D represents a $C_{6-14}$ aryl group which optionally has 1 to 3 substituents selected from Substituent Group α or a 5- to 6-membered heteroaryl group which optionally has 1 to 3 substituents selected from Substituent Group α; $R^{10}$ represents a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α; $R^{11}$ and $R^{12}$ are each independently a hydrogen atom, a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α, or $R^{11}$ and $R^{12}$ together may form a ring; $R^{13}$ represents a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl group which optionally has 1 to 3 substituents selected from Substituent Group α, a $C_{1-6}$ alkyl group which optionally has 1 to 3 substituents selected from Substituent Group α or a 3- to 10-membered carbocyclic group which optionally has 1 to 3 substituents selected from Substituent Group α; and $R^{14}$ represents a $C_{7-12}$ aralkyl group which optionally has 1 to 3 substituents selected from Substituent Group α.

General Preparation Method 14 is a method for preparing the compounds (I-c) to (I-g) of the general formula (I) according to the present invention, wherein Y is a nitrogen atom and $R^1$ and $R^2$ are hydrogen atoms, from a compound (14-1).

The compound (14-1) can be prepared from a commercially available product by General Preparation Method 5, General Preparation Method 8, General Preparation Method 9, General Preparation Method 10, General Preparation Method 11, General Preparation Method 12 or a combination thereof, and can also be prepared by a method described in Preparation Examples among Examples.

Compounds (14-3), (14-4), (14-5), (14-6), (14-7), (14-8) and (14-9) each can be a commercially available product used as is, can also be prepared from a commercially available product by a method known to a person skilled in the art, and can further be prepared by a method described in Preparation Examples among Examples.

Step 14-1:

This step is a step of obtaining a compound (14-2) by deprotecting the amino group of the compound (14-1).

The reaction can be performed under the same conditions as those generally used in deprotection of a protecting group of an amino compound such as the conditions described in a document such as T. W. Green and P. G. M. Wuts, "Protective Groups in Organic Chemistry, Third Edition", John Wiley & Sons, P. 494-572.

The amino protecting group used in this step is not particularly limited. When Prt₃ is a 2,4-dimethoxybenzyl group, for example, this step can be performed under the same conditions as those generally used (such as the conditions described in a document such as Tetrahedron Vol. 47, No. 26, pp 4591-4602, 1991). One Boc group can be deprotected simultaneously with deprotection of the 2,4-dimethoxybenzyl group. The solvent used in this step is not particularly limited insofar as it does not inhibit the reaction and allows the starting material to be dissolved therein to a certain extent. For example, the first-step reaction solvent may be methylene chloride or chloroform, and the second-step reaction solvent may be methanol. The reaction temperature in this step is usually 0° C. to room temperature. The reaction time in this step is not particularly limited and is usually 0.5 to 24 hours, and preferably 0.5 to 12 hours.

When Prt₃ is a benzyloxycarbonyl group, the compound (14-2) can be obtained by deprotecting the compound (14-1) by hydrogenation using palladium-carbon as a catalyst in a solvent such as an alcohol, for example.

Step 14-2:
This step is a step of synthesizing the compound (I-c) from the compound (14-2) as a raw material using a method described in the above preparation method ((Step 3-3) and (Step 3-4)).

Step 14-3:
This step is a step of synthesizing the compound (I-d) using a method described in the above preparation method (Step 3-4) after reductive amination reaction of the compound (14-2) with the compound (14-5).

The reductive amination reaction can be performed under the same conditions as those usually used in reductive amination reaction of a carbonyl compound with an amine compound. The reduction reaction in this step is not particularly limited. Examples of the reduction reaction include reductive amination reaction using a reducing agent such as borane or a boron hydride complex compound. Examples of the reductive amination reaction using a boron hydride complex compound include a method described in a document such as J. Org. Chem. 1996, 61, 3849. Examples of the boron hydride complex compound that can be used include sodium borohydride, sodium cyanoborohydride and sodium triacetoxyborohydride.

When the boron hydride complex compound is used as a reducing agent, the solvent is not particularly limited insofar as it does not inhibit the reaction and allows the starting material to be dissolved therein to a certain extent. Specific examples of the solvent that can be used include methanol, ethanol, tetrahydrofuran, N,N-dimethylformamide, dichloromethane and 1,2-dichloroethane. A more preferable result such as an improved yield can be achieved by carrying out this reaction in the presence of an acid. Such an acid is not particularly limited. Preferable examples of the acid include mineral acids such as hydrochloric acid, organic acids such as acetic acid, and Lewis acids such as zinc chloride, a boron trifluoride-diethyl ether complex and titanium (IV) tetraisopropoxide.

Step 14-4:
This step is a step of synthesizing the compound (I-e) using a method described in the above preparation method (Step 3-4) after sulfonylation of the amino group of the compound (14-2). For the sulfonylation, reaction using a sulfonyl chloride derivative is known to a person skilled in the art.

Step 14-5:
This step is a step of synthesizing the compound (I-f) using a method described in the above preparation method (Step 3-4) after coupling reaction of the compound (14-2) with the compound (14-7) or (14-8). Reaction such as coupling using a transition metal complex or the like or nucleophilic aromatic substitution (SNAr reaction) is used in this step.

The coupling reaction in this step can be performed under the same conditions as those described in Org. Lett. 2007, Vol. 9, No. 5, 761-764 and Org. Lett. 2003, Vol. 5, No. 23, 4397-4400, for example. Specifically, the coupling reaction can be performed by reacting the compound (14-2) with the compound (14-7) at room temperature to 50° C. using a solvent such as dichloromethane in the presence of molecular sieve 4A and a catalyst such as copper (II) acetate, for example.

The catalyst used in this reaction is not particularly limited. Preferable examples of the catalyst include metal catalysts such as copper (II) acetate, copper (II) sulfate, copper (I) iodide and copper (I) chloride. The amount of the catalyst used is not particularly limited and is usually about 0.1 to 0.5 equivalent with respect to the raw material. The solvent used in this reaction is not particularly limited insofar as it does not inhibit the reaction and allows the starting material to be dissolved therein to a certain extent. Preferable examples of the solvent include N,N-dimethylformamide, 1-methyl-2-pyrrolidone, tetrahydrofuran, 1,2-dimethoxyethane, 1,4-dioxane, acetonitrile, propionitrile and dichloromethane. The reaction temperature is not particularly limited and is usually ice-cold temperature to solvent reflux temperature, and preferably room temperature to solvent reflux temperature, for example. The reaction time is not particularly limited and is usually 0.5 to 100 hours, and preferably 1 to 72 hours.

A more preferable result such as an improved yield may be achieved by carrying out this reaction in an oxygen atmosphere.

When this step is coupling using a transition metal complex or the like as a catalyst, the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative under the same conditions as those usually used (such as the conditions described in a document such as Org. Lett. 2002, Vol. 4, No. 4, 581). The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. Examples of the transition metal complex used in this step include dichlorobis(triphenylphosphine)palladium (II), tetrakis(triphenylphosphine)palladium (0), tris(dibenzylideneacetone) palladium (0) and a copper-diol ligand complex. In this reaction, a phosphorus ligand (such as preferably triphenylphosphine, tri-o-tolylphosphine, tri-tert-butylphosphine, 2,2'-bis(diphenylphosphino)-1,1'-binaphthyl or 1,1'-bis(diphenylphosphino)ferrocene) may be further added in order to obtain favorable results (such as a reduced reaction temperature, a reduced reaction time and an improved yield). When the transition metal complex used is a palladium complex, the reaction in this step is preferably performed under a nitrogen or argon atmosphere. The solvent used in this step is not particularly limited insofar as it does not inhibit the reaction and allows the starting material to be dissolved therein to a certain extent. For example, when the transition metal complex used is a palladium complex, N,N-dimethylformamide, N-methyl-2-pyrrolidone, 1,4-dioxane, toluene, xylene or the like can be used. When the transition metal complex used is a copper-diol complex, 2-propanol or the like can be used. The reaction temperature in this step is usually room temperature to solvent reflux temperature. The reaction time in this step is not particularly limited and is usually 0.5 to 72 hours, and preferably 0.5 to 24 hours.

When this step is nucleophilic aromatic substitution (SNAr reaction), the reaction can be performed using the compound (14-2) and the compound (14-8) which is an aryl halide derivative, a heteroaryl halide derivative, an aryloxy trifluoromethanesulfonate derivative or a heteroaryloxy trifluoromethanesulfonate derivative in the presence of a base under the same conditions as those usually used. The aryl halide derivative, the heteroaryl halide derivative, the aryloxy trifluoromethanesulfonate derivative or the heteroaryloxy trifluoromethanesulfonate derivative used in this step can be a commercially available product used as is, and can also be prepared from a commercially available product by a method known to a person skilled in the art. The nucleophilic aromatic substitution (SNAr reaction) used in this step can be performed under the same conditions as those generally used (such as the conditions according to methods described in documents such as Org. Prep. Proced. int. 39 (2007) 4, 399-402, Bioorg. Med. Chem. Lett. 15 (2005) 9, 2409-2413 and Bioorg. Med. Chem. Lett. 15 (2005) 3, 719-723). The solvent used in this step is not particularly limited insofar as it does not inhibit the reaction and allows the starting material to be dissolved therein to a certain extent. Examples of the solvent that can be used include N,N-dimethylformamide, N-methyl-2-pyrrolidone, dimethyl sulfoxide and acetonitrile. The base used in this step is not particularly limited. Examples of the base include potassium carbonate, sodium carbonate, sodium hydride and tetrabutylammonium fluoride. Potassium carbonate, sodium carbonate and tetrabutylammonium fluoride are preferably used. The reaction temperature in this step is usually room temperature to solvent reflux temperature. The reaction time in this step is not particularly limited and is usually 0.5 to 24 hours, and preferably 0.5 to 12 hours.

Step 14-6:

This step is a step of synthesizing the compound (I-g) from the compound (14-2) as a raw material using a method described in the above preparation method ((Step 8-1) and (Step 3-4)).

The compound of the formula (I) according to the present invention, wherein at least one of $R^1$ and $R^2$ is a $C_{1-6}$ alkyl group which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α, can be obtained by further reacting any of the compounds (I-c) to (I-g) obtained in General Preparation Method 14 with a corresponding halide compound such as a $C_{1-6}$ alkyl halide.

The compound of the formula (I) according to the present invention obtained in this manner can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution. The compound of the formula (I) according to the present invention can be converted to a solvate by subjecting the compound to solvate forming reaction known per se where necessary.

The fused aminodihydropyrimidone derivative or pharmaceutically acceptable salt thereof or solvate thereof according to the present invention has an extremely excellent Aβ production inhibitory effect or BACE1 inhibitory effect and is extremely useful as a prophylactic or therapeutic agent for a neurodegenerative disease caused by Aβ and typified by Alzheimer-type dementia.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for the treatment or prevention of a neurodegenerative disease. Examples of neurodegenerative diseases include Alzheimer-type dementia and Down's syndrome.

The fused aminodihydropyrimidone derivative or pharmaceutically acceptable salt thereof or solvate thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydropyrimidone derivative or pharmaceutically acceptable salt thereof or solvate thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydropyrimidone derivative or pharmaceutically acceptable salt thereof or solvate thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydropyrimidone derivative or pharmaceutically acceptable salt thereof or solvate thereof according to the present invention varies according to the degree of symptoms, age, sex, body weight, mode of administration, type of salt and specific type of disease, for example. Typically, the active ingredient is orally administered to an adult at about 30 µg to 10 g, preferably 100 µg to 5 g, and more preferably 100 µg to 1 g per day, or is administered to an adult by injection at about 30 µg to 1 g, preferably 100 µg to 500 mg, and more preferably 100 µg to 300 mg per day, in one or several doses, respectively.

Compounds of the formula (I) may be used in combination with other therapeutic agents, for example medicaments claimed to be useful as either disease modifying or symptomatic treatments of Alzheimer's disease. Suitable examples of such other therapeutic agents may be symptomatic agents, for examples those known to modify cholinergic transmission such as M1 and M3 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-HT$_4$ receptor agonists or partial agonists, histamine H3 antagonists, 5-HT$_6$ receptor antagonists or 5HT1A receptor ligands and NMDA receptor antagonists or modulators, or disease modifying agents such as β-secretase inhibitors.

Thus, in a further aspect, the present invention provides a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

In a further aspect, the invention provides a method of inhibiting production of amyloid-β protein and/or of treating or preventing a neurodegenerative disease, such as Alzheimer-type dementia and Down's syndrome, the method involving administering to a human subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below.

PyBOP: benzotriazol-1-yloxytris(pyrrolidino)phosphonium hexafluorophosphate;
Pd$_2$DBA$_3$: tris(dibenzylideneacetone)dipalladium; Pd(t-Bu$_3$P)$_2$: bis(tri-t-butylphosphine)palladium; pTLC: preparative thin-layer chromatography; LCMS, LC/MS & LC-MS (liquid chromatography/mass spectrometry); MS (mass spectrometry); MDAP (mass directed auto purification); NMR (nuclear magnetic resonance); s, d, t, dd, m, br (singlet, doublet, triplet, doublet of doublets, multiplet, broad); Ph, Me, Et, Pr, Bu, Bn (phenyl, methyl, ethyl, propyl, butyl, benzyl); THF (tetrahydrofuran); DCM (dichloromethane); DMF (N,N-dimethylformamide); h, hr, hrs (hours); EDC & EDAC (N-3(-dimethylaminopropyl)N'ethylcarbodiimide hydrochloride); DMAP (4-N,N-dimethylaminopyridine); DMSO (dimethylsulfoxide); UV (ultraviolet); RT & rt (room temperature); Rt (retention time); min & mins (minutes); EtOAc (ethyl acetate); Et₂O (diethyl ether); MeCN (acetonitrile); EtOH (ethanol); MeOH (methanol); PhCH₃ & PhMe (toluene); tlc (thin layer chromatography); TFA (Trifluoroacetic acid); NaOH (sodium hydroxide); HCl (hydrochloric acid); NMP (N-methylpyrrolidinone or 1-methyl-2-pyrrolidinone); HPLC (high performance liquid chromatography); TBAF (tetrabutylammonium fluoride); BuLi (n-butyl lithium); SCX (strong cation exchange:—Isolute Flash SCX-2, Biotage); TEA (triethylamine); BOC & Boc (tert-butoxycarbonyl).

¹H NMR spectra were recorded on a Bruker AM series spectrometer operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.
HPLC Conditions:
Analytical:
Method A: Agilent ZORBAX Eclipse XDB-C18, 4.6×150 mm, 5.0 µm, 1.5 mL per min, gradient 5-95% MeCN in water (0.1% formic acid) over 5.00 min—held for 3.00 min.
Purification:
Method B: Reverse phase HPLC (Phenomenex Luna C18, 250×50 mm, 10 um, 80 mL per min, gradient 35% to 100% (over 20 min) then 100% (5 min) MeCN in H₂O [0.1% acetic acid]).

PREPARATION OF INTERMEDIATE 1

Synthesis of 5-cyanopyridine-2-carboxylic acid

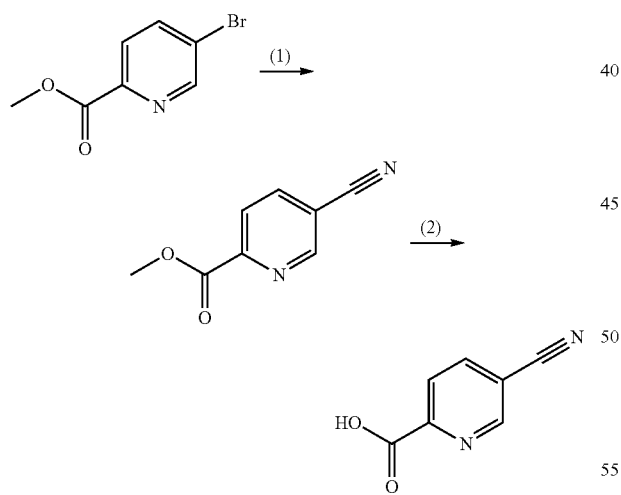

Synthesis of methyl 5-cyanopyridine-2-carboxylate

A mixture of methyl 5-bromopyridine-2-carboxylate (2.8 g) and copper cyanide (3.6 g) in NMP (30 mL) was heated with stirring at 170° C. for 1.5 h. Water was added to the reaction solution at RT, and the insoluble matter was removed by filtration. The filtrate was extracted with EtOAc. The extract was washed with a saturated NaCl solution and then dried over anhydrous MgSO₄. The drying agent was removed by filtration and the filtrate was concentrated under reduced pressure. The resulting crude product was purified by silica gel column chromatography (EtOAc-heptane system) to obtain the title compound (920 mg). ¹H-NMR (400 MHz, CDCl₃) δ (ppm): 4.06 (s, 3H), 8.16 (dd, J=2.0, 8.0 Hz, 1H), 8.27 (d, J=8.0 Hz, 1H), 9.01 (d, J=2.0 Hz, 1H).

Synthesis of 5-cyanopyridine-2-carboxylic acid

A solution of methyl-5-cyanopyridine-2-carboxylate (920 mg) and a 5 N NaOH solution (2.26 mL) in ethanol (30 mL) was stirred at RT for 10 min. 5 N hydrochloric acid (5.2 mL) was added to the reaction solution at RT, followed by extraction with EtOAc. The extract was dried over anhydrous MgSO₄. The drying agent was removed by filtration and the filtrate was concentrated under reduced pressure to obtain the title compound (800 mg). ¹H-NMR (400 MHz, DMSOd₆) δ (ppm): 8.18 (d, J=8.0 Hz, 1H), 8.51 (dd, J=2.0, 8.0 Hz, 1H), 9.12-9.18 (m, 1H).

PREPARATION OF INTERMEDIATE 2

Synthesis of 5-difluoromethylpyrazine-2-carboxylic acid

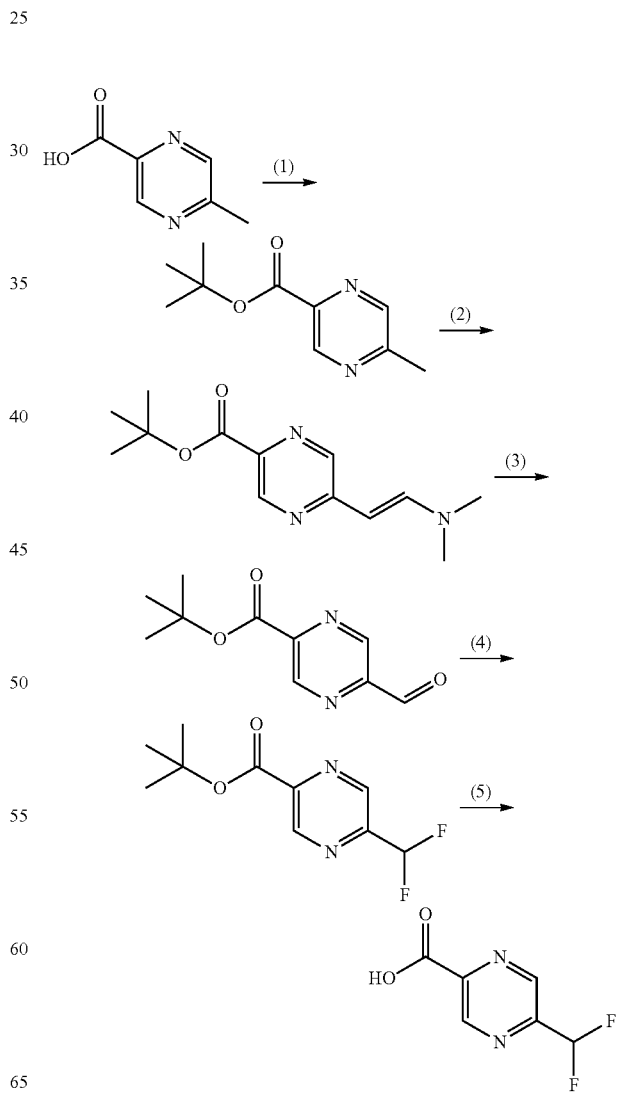

(1) Synthesis of t-butyl 5-methylpyrazine-2-carboxylate

A boron trifluoride-diethyl ether complex (91.7 µL) was added dropwise to a suspension of 2-methylpyrazine-5-carboxylic acid (1 g) and tert-butyl 2,2,2-trichloroacetimidate (4.75 g) in THF (20 mL) under ice-cooling. The reaction solution was warmed to RT, followed by stirring for 2 h. A saturated NaCl solution and EtOAc were added to the reaction solution, and the organic layer was separated. The organic layer was dried over anhydrous $MgSO_4$, and the insoluble matter was separated by filtration. The filtrate was concentrated and purified by silica gel column chromatography to obtain the title compound (1.4 g). $^1$H-NMR ($CDCl_3$) δ (ppm): 1.65 (s, 9H), 2.65 (s, 3H), 8.57 (d, J=1.2 Hz, 1H), 9.10 (d, J=1.6 Hz, 1H).

(2) Synthesis of t-butyl 5-((E)-2-dimethylamino-vinyl)-pyrazine-2-carboxylate A mixture of t-butyl 5-methylpyrazine-2-carboxylate (1.35 g), DMF (25 mL) and N,N-dimethylformamide dimethylacetal (25 mL) was stirred at 130° C. for 5 h. The reaction solution was cooled to RT and diluted with EtOAc. The mixture was washed with a saturated NaCl solution three times. The organic layer was dried over anhydrous $MgSO_4$, and the insoluble matter was separated by filtration. The filtrate was concentrated and the residue was purified by silica gel column chromatography to obtain the title compound (648 mg). $^1$H-NMR ($CDCl_3$) δ (ppm): 1.63 (s, 9H), 3.00 (s, 6H), 5.16 (d, J=12.8 Hz, 1H), 7.72 (d, J=12.8 Hz, 1H), 8.16 (d, J=1.2 Hz, 1H), 8.81 (d, J=1.6 Hz, 1H).

(3) Synthesis of t-butyl 5-formylpyrazine-2-carboxylate

Sodium periodate (1.67 g) was added to a solution of t-butyl 5-((E)-2-dimethylamino-vinyl)-pyrazine-2-carboxylate (645 mg) in 50% THF-water (26 mL), and the mixture was stirred at RT for 4 h. A saturated $NaHCO_3$ solution and EtOAc were added to the reaction solution, and the organic layer was separated. The organic layer was washed with a saturated NaCl solution and dried over anhydrous $MgSO_4$. The insoluble matter was separated by filtration and the filtrate was concentrated. The residue was purified by silica gel column chromatography to obtain the title compound (249 mg). $^1$H-NMR ($CDCl_3$) δ (ppm): 1.68 (s, 9H), 9.25 (d, J=1.2 Hz, 1H), 9.36 (d, J=1.6 Hz, 1H), 10.2 (s, 1H).

(4) Synthesis of t-butyl 5-difluoromethylpyrazine-2-carboxylate

[Bis(2-methoxyethyl)amino]sulfur trifluoride (662 µL) was added dropwise to a solution of t-butyl 5-formylpyrazine-2-carboxylate (249 mg) in $CH_2Cl_2$ (12 mL) under a $N_2$ atmosphere under ice-cooling. The reaction solution was stirred for 2 h while gradually returning to RT. A saturated $NaHCO_3$ solution and EtOAc were added to the reaction solution, and the organic layer was separated. The organic layer was washed with a saturated NaCl solution and dried over anhydrous $MgSO_4$. The insoluble matter was separated by filtration and the filtrate was concentrated. The residue was purified by silica gel column chromatography to obtain the title compound (175 mg). $^1$H-NMR ($CDCl_3$) δ (ppm): 1.67 (s, 9H), 6.75 (t, J=54.4 Hz, 1H), 9.02 (d, J=0.8 Hz, 1H), 9.25 (d, J=0.8 Hz, 1H).

(5) Synthesis of 5-difluoromethylpyrazine-2-carboxylic acid

Trifluoroacetic acid (1 mL) was added to a solution of t-butyl 5-difluoromethylpyrazine-2-carboxylate (175 mg) in dichloromethane (1 mL), and the mixture was stirred at RT for 5 h. Ether and 5 N NaOH were added to the reaction solution. The aqueous layer was separated and made acidic with 5 N hydrochloric acid. EtOAc was added to the aqueous layer, and the organic layer was separated. The organic layer was dried over anhydrous $MgSO_4$, and the insoluble matter was separated by filtration. The filtrate was concentrated to obtain the title compound (100 mg). $^1$H-NMR ($CDCl_3$) δ (ppm): 6.80 (t, J=54.4 Hz, 1H), 9.02 (s, 1H), 9.47 (s, 1H).

EXAMPLE 1

(±)-N-(3-((4aS*,7aS*)-2-amino-3-methyl-4-oxo-3,4,4a,5,7,7a-hexahydrofuro[3,4-d]pyrimidin-7a-yl)-4-fluorophenyl)-5-(difluoromethyl)picolinamide

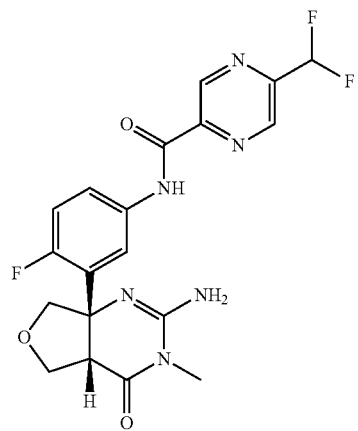 [SMILES: CN1C(=O)[C@@H]2COC[C@]2(c2cc(NC(=O)c3cnc(C(F)F)cn3)ccc2F)N=C1N]

Step 1: Allyloxy-acetaldehyde oxime

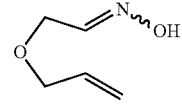

A solution containing oxalyl chloride (27.3 mL) in $CH_2Cl_2$ (600 mL) was cooled to −78° C. under a $N_2$ atmosphere. A solution containing DMSO (24.3 mL) in $CH_2Cl_2$ (50 mL) was added dropwise to the reaction solution at the same temperature. After stirring at the same temperature for 10 min, a solution containing 2-allyloxyethanol (25 g) in $CH_2Cl_2$ (50 mL) was added dropwise to the reaction solution at the same temperature. After stirring at the same temperature for 1 h, triethylamine (102 mL) was added to the reaction solution. The cooling bath was removed. The reaction solution was warmed to RT and stirred at RT for 1 h. Saturated aqueous ammonium chloride was added to the reaction solution. The organic layer was separated and washed with saturated aqueous sodium chloride. The organic layer was dried over anhydrous $MgSO_4$, and the insoluble matter was separated by filtration. The filtrate was concentrated under reduced pressure. The residue was dissolved in ethanol (500 mL) and water (50 mL). Sodium acetate (60.2 g) and hydroxylamine sulfate (40.2 g) were added to the reaction solution at RT. The reaction solution was stirred at RT for 15 h. Then, water and EtOAc were added and the organic layer was separated. The organic layer was washed with saturated aqueous sodium chloride and dried over anhydrous MgSO₄. The insoluble matter was separated by filtration and the filtrate was concentrated under reduced pressure. The residue was purified by silica gel column chromatography to obtain the title compound (13.2 g). ¹H NMR (400 MHz, CDCl₃) δ ppm 4.00-4.04 (m, 2H), 4.09-4.11 (m, 1H), 4.35 (d, J=3.6 Hz, 1H), 5.21-5.25 (m, 1H), 5.27-5.35 (m, 1H), 5.85-5.95 (m, 1H), 6.92 (t, J=4.0 Hz, 0.5H), 7.51 (t, J=5.6 Hz, 0.5H).

Step 2:
(±)-3a,4-Dihydro-3H,6H-furo[3,4-c]isoxazole

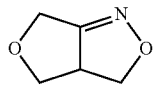

A 5% sodium hypochlorite solution (170 mL) was added to a solution containing allyloxy-acetaldehyde oxime (13.2 g) in CH₂Cl₂ (400 mL) at RT, and the mixture was stirred at RT for 6 h. Water and sodium bisulfite (7.95 g) were added to the reaction solution, followed by stirring at RT for 10 min. Then, the organic layer was separated. The organic layer was dried over anhydrous MgSO₄. The insoluble matter was separated by filtration and the filtrate was concentrated under reduced pressure. The residue was purified by silica gel column chromatography to obtain the title compound (4.8 g). ¹H NMR (400 MHz, CDCl₃) δ ppm 3.65 (dd, J=9.2, 8.0 Hz, 1H), 4.00 (dd, J=12.0, 8.0 Hz, 1H), 4.17-4.29 (m, 2H), 4.40-4.49 (m, 2H), 4.59 (dd, J=9.2, 8.0 Hz, 1H).

Step 3: (±)-(3aS*,6aS*)-6a-(2-Fluorophenyl)tetrahydrofuro[3,4-c]isoxazole

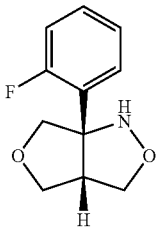

A 2.77 M solution of n-butyllithium in hexane (30.7 mL) was added dropwise to a solution containing 2-bromofluorobenzene (15.6 g) in THF/toluene (50 mL/150 mL) under a nitrogen atmosphere at −78° C. The reaction solution was stirred at the same temperature for 1 h. A boron trifluoride-diethyl ether complex (10.7 mL) was added dropwise to a solution containing (±)-3a,4-dihydro-3H,6H-furo[3,4-c]isoxazole (4.8 g) in toluene (350 mL) under a nitrogen atmosphere at −78° C. Previously prepared 2-fluorophenyllithium was added dropwise to the reaction solution at the same temperature. After stirring at the same temperature for 1 h, aqueous ammonium chloride was added to the reaction solution, and the reaction solution was warmed to RT. Water and EtOAc were added to the reaction solution, and the organic layer was separated. The organic layer was washed with a saturated sodium chloride solution. The organic layer was dried over anhydrous MgSO₄, and the insoluble matter was separated by filtration. The filtrate was concentrated under reduced pressure. The residue was purified by silica gel column chromatography to obtain the title compound (5.6 g). ¹H NMR (400 MHz, CDCl₃) δ ppm 3.39-3.45 (m, 1H), 3.52-3.62 (brm, 1H), 3.84-3.92 (brm, 2H), 3.98 (brd, J=9.2 Hz, 1H), 4.16 (ddd, J=2.4, 6.4, 11.2 Hz, 1H), 4.50-4.58 (brm, 1H), 5.11 (brs, 1H), 7.06 (ddd, J=1.2, 8.4, 11.6 Hz, 1H), 7.16 (ddd, J=1.2, 7.6, 7.6 Hz, 1H), 7.25-7.31 (m, 1H), 7.84-7.95 (m, 1H).

Step 4: (±)-[(3R*,4S*)-4-Amino-4-(2-fluorophenyl)tetrahydrofuran-3-yl]methanol

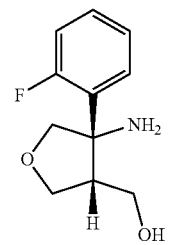

Zinc (powder, 21 g) was added to a solution containing (±)-(3aS*,6aS*)-6a-(2-fluorophenyl)tetrahydrofuro[3,4-c]isoxazole (5.6 g) in acetic acid (140 mL) at RT. The reaction solution was stirred at RT for 16 h. The insoluble matter was separated by filtration through celite and the filtrate was concentrated under reduced pressure. EtOAc and a sodium bicarbonate solution were added to the residue, and the organic layer was separated. The organic layer was washed with saturated aqueous sodium chloride. The aqueous layer was further extracted with EtOAc three times. The organic layers were combined and dried over anhydrous MgSO₄. The insoluble matter was separated by filtration and the filtrate was concentrated under reduced pressure to obtain the title compound (5.46 g). ESI-MS; m/z 212 [M+H]⁺. ¹H NMR (CDCl₃) δ ppm 2.81-2.88 (m, 1H), 3.83 (dd, J=6.8, 12.0 Hz, 1H), 3.92 (dd, J=3.2, 8.8 Hz, 1H), 3.94-4.00 (m, 2H), 4.07 (dd, J=8.4, 9.2 Hz, 1H), 4.14 (dd, J=1.2, 8.8 Hz, 1H), 7.09 (ddd, J=1.2, 8.0, 12.4 Hz, 1H), 7.16 (ddd, J=1.2, 7.6, 8.0 Hz, 1H), 7.26-7.32 (m, 1H), 7.53 (dt, J=2.0, 8.0 Hz, 1H).

Step 5: (±)-tert-Butyl-[(3S*,4R*)-3-(2-fluorophenyl)-4-(hydroxymethyl)tetrahydrofuran-3-yl]carbamate

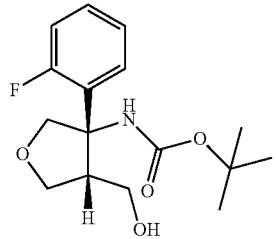 [SMILES: CC(C)(C)OC(=O)N[C@@]1(c2ccccc2F)COC[C@H]1CO]

[(±)-(3R*,4S*)-4-amino-4-(2-fluorophenyl)tetrahydrofuran-3-yl]methanol (1.05 g) was transferred into the reaction vessel. THF was transferred into the reaction vessel. N,N-diethylethanamine (0.83 mL) was transferred into the reaction vessel. Di-tert-butyl dicarbonate (1.19 g) was transferred into the reaction vessel. The reaction mixture was stirred at RT for 18 h. Saturated sodium bicarbonate solution (100 mL)

was added, followed by extraction with EtOAc (2×100 mL). The combined organic extracts were dried over MgSO₄, filtered and concentrated under reduced pressure. The crude product was purified by column chromatography in EtOAc: Hexane (1:2) to give the title compound (1.24 g). $^1$H NMR (400 MHz, CDCl₃) δ ppm 1.31-1.44 (m, 9H) 3.25 (br. s., 1H) 3.61 (br. s., 1H) 3.68-3.82 (m, 3H) 4.08 (t, J=8.21 Hz, 2H) 4.14 (q, J=7.07 Hz, 1H) 5.91 (br. s., 1H) 7.04 (dd, J=12.38, 8.08 Hz, 1H) 7.11-7.20 (m, 1H) 7.22-7.33 (m, 1H) 7.80 (br. s., 1H).

Step 6: (±)-(3S*,4S*)-4-amino-4-(2-fluorophenyl)tetrahydrofuran-3-carboxylic acid

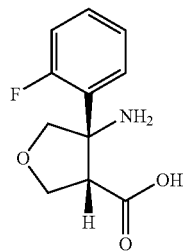

Tert-butyl [(±)-(3S*,4R*)-3-(2-fluorophenyl)-4-(hydroxymethyl)tetrahydrofuran-3-yl]carbamate (0.3 g) was transferred into the reaction vessel. Water (2 mL) was transferred into the reaction vessel. Acetone (6 mL) was transferred into the reaction vessel. Chromium trioxide (96 mg) was transferred into the reaction vessel. Sulphuric acid (1 mL) was transferred into the reaction vessel. The reaction mixture was stirred at RT for 18 h. The oxidation was completed concomitant with the BOC group removal, leaving the amino acid product. The crude reaction mixture was concentrated and then taken to the next chemical step.

Step 7: Methyl (±)-(3S*,4S*)-4-amino-4-(2-fluorophenyl)tetrahydrofuran-3-carboxylate

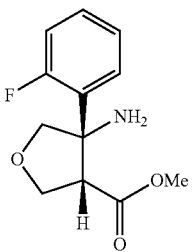

(±)-(3S*,4S*)-4-Amino-4-(2-fluorophenyl)tetrahydrofuran-3-carboxylic acid (0.22 g) was transferred into the reaction vessel. Methanol (15 mL) was transferred into the reaction vessel. Sulphuric acid (1 mL) was transferred into the reaction vessel. The reaction was stirred at 70° C. for 8 h. The reaction mixture was concentrated under reduced pressure. Saturated sodium bicarbonate (40 mL) was then added followed by an extraction with DCM (3×40 mL). The combined organic phases were dried over MgSO₄, filtered and concentrated. The crude product was purified by preparative HPLC (Method B) to give the title compound (120 mg). $^1$H NMR (400 MHz, CDCl₃) δ ppm 3.73 (s, 3H) 3.78 (t, J=8.21 Hz, 1H) 4.02 (dd, J=8.91, 2.97 Hz, 1H) 4.15 (d, J=8.97 Hz, 1H) 4.22 (t, J=8.72 Hz, 1H) 4.36-4.44 (m, 1H) 7.09 (ddd, J=12.41, 8.12, 1.20 Hz, 1H) 7.18 (td, J=7.64, 1.14 Hz, 1H) 7.29-7.35 (m, 1H) 7.63 (td, J=8.05, 1.45 Hz, 1H).

Step 8: tert-Butyl (±)-((4aS*,7aS*)-7a-(2-fluorophenyl)-3-methyl-4-oxo-3,4,4a,5,7,7a-hexahydrofuro[3,4-d]pyrimidin-2-yl)carbamate

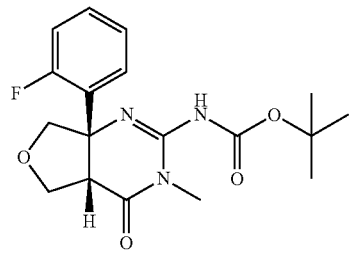 [SMILES: CN1C(=O)[C@@H]2COC[C@]2(c2ccccc2F)N=C1NC(=O)OC(C)(C)C]

Methyl (±)-(3S*,4S*)-4-amino-4-(2-fluorophenyl)tetrahydrofuran-3-carboxylate (120 mg) was transferred into the reaction vessel. Tert-butyl (methylcarbamothioyl) carbamate (95 mg) was transferred into the reaction vessel. DMF (2 mL) was transferred into the reaction vessel. N-Ethyl-N-(propan-2-yl)propan-2-amine (0.174 mL) was transferred into the reaction vessel. N-[3-(dimethylamino)propyl]-N'-ethylcarbodiimide hydrochloride (0.078 g) was transferred into the reaction vessel. The reaction was stirred for 12 h at RT. The mixture was concentrated under reduced pressure. Saturated sodium bicarbonate solution (20 mL) was then added followed by extraction with DCM (3×20 mL). The combined organic phases were dried over MgSO₄, filtered and concentrated under reduced pressure. The crude product was purified by preparative HPLC (method B) to give the title compound (100 mg). $^1$H NMR (400 MHz, CDCl₃) δ ppm 1.40-1.47 (m, 9H) 3.22 (s, 3H) 3.79-3.87 (m, 1H) 4.07 (t, J=8.59 Hz, 1H) 4.13 (dd, J=9.60, 0.88 Hz, 1H) 4.32 (dd, J=9.60, 3.66 Hz, 1H) 4.42 (t, J=9.03 Hz, 1H) 7.03-7.13 (m, 1H) 7.15-7.22 (m, 2H) 7.26-7.34 (m, 1H).

Step 9: (±)-(4aS*,7aS*)-2-Amino-7a-(2-fluoro-5-nitrophenyl)-3-methyl-4-a,5,7,7a-tetrahydrofuro[3,4-d]pyrimidin-4(3H)-one

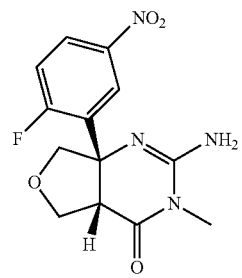 [SMILES: CN1C(=O)[C@@H]2COC[C@]2(c2cc([N+](=O)[O-])ccc2F)N=C1N]

tert-Butyl (±)-((4aS*,7aS*)-7a-(2-fluorophenyl)-3-methyl-4-oxo-3,4,4a,5,7,7a-hexahydrofuro[3,4-d]pyrimidin-2-yl)carbamate (120 mg, 0.3302 mmol) was transferred into the reaction vessel. Nitric acid (12 mL, 287.56 mmol) was slowly transferred into the reaction vessel. The reaction mixture was stirred at RT. After 1 h, the reaction mixture was concentrated and the residue was purified by flash chromatography (DCM/

Methanol (0-10%)/TEA (1%)) to give the title compound (57 mg). $^1$H NMR (400 MHz, CDCl$_3$) δ ppm 3.46 (s, 3H) 3.93 (dd, J=9.85, 6.57 Hz, 1H) 4.21-4.35 (m, 2H) 4.54 (ddd, J=9.73, 5.43, 4.04 Hz, 2H) 7.36 (t, J=10.11 Hz, 1H) 8.26-8.35 (m, 2H)

Step 10: (±)-tert-Butyl ((4aS*,7aS*)-7a-(2-fluoro-5-nitrophenyl)-3-methyl-4-oxo-3,4,4a,5,7,7a-hexahydrofuro[3,4-d]pyrimidin-2-yl)carbamate

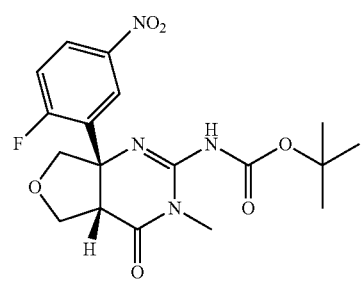

(±)-(4aS*,7aS*)-2-Amino-7a-(2-fluoro-5-nitrophenyl)-3-methyl-4a,5,7,7a-tetrahydrofuro[3,4-d]pyrimidin-4(3H)-one (150 mg, 0.48 mmol) was transferred into the reaction vessel followed by THF (2 mL). di-tert-Butyl dicarbonate (106 mg, 0.48 mmol), N,N-diethylethanamine (0.07 mL, 0.48 mmol), and N,N-dimethylpyridin-4-amine (6 mg, 0.05 mmol) were transferred into the reaction vessel. The reaction was stirred at RT. After 60 mins, the mixture was concentrated and the residue was purified by flash chromatography (EtOAc/Hexane, 0-50%) to give the title compound (196 mg). LCMS (Method A) Rt 4.23 min, ESI-MS: m/z 409 [M+H]$^+$.

Step 11: (±)-tert-Butyl ((4aS*,7aS*)-7a-(5-amino-2-fluorophenyl)-3-methyl-4-oxo-3,4,4a,5,7,7a-hexahydrofuro[3,4-d]pyrimidin-2-yl)carbamate

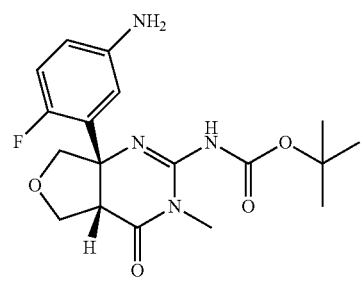 [SMILES: CN1C(=O)[C@@H]2COC[C@]2(c2cc([N+](=O)[O-])ccc2F)N=C1NC(=O)OC(C)(C)C]

(±)-tert-Butyl ((4aS*,7aS*)-7a-(2-fluoro-5-nitrophenyl)-3-methyl-4-oxo-3,4,4a,5,7,7a-hexahydrofuro[3,4-d]pyrimidin-2-yl)carbamate (60 mg, 0.14 mmol) was transferred into the reaction vessel. Zinc (100 mg, 1.53 mmol) was transferred into the reaction vessel. The reaction was stirred at 0° C. for 30 mins. The reaction was filtered, concentrated and the residue was purified by flash chromatography (EtOAc/Hexane, 20-100%) to give the title compound (56 mg). LCMS (Method A) Rt 2.33 min, ESI-MS: m/z 279 [MH-BOC]$^+$.

Step 12: (±)—N-(3-((4aS*,7aS*)-2-amino-3-methyl-4-oxo-3,4,4a,5,7,7a-hexahydrofuro[3,4-d]pyrimidin-7a-yl)-4-fluorophenyl)-5-(difluoromethyl)picolinamide

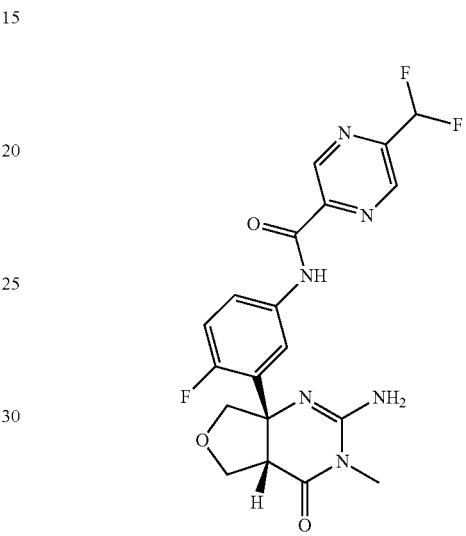

(±)-tert-Butyl ((4aS*,7aS*)-7a-(5-amino-2-fluorophenyl)-3-methyl-4-oxo-3,4,4a,5,7,7a-hexahydrofuro[3,4-d]pyrimidin-2-yl)carbamate (11 mg, 0.03 mmol) was dissolved in DCM (2 mL). 5-(difluoromethyl)pyrazine-2-carboxylic acid (8 mg, 0.04 mmol) was transferred into the reaction vessel. N-ethyl-N-(propan-2-yl)propan-2-amine (7.5 mg, 0.06 mmol) was transferred in to the reaction vessel. N-[3-(dimethylamino)propyl]-N'-ethylcarbodiimide (7 mg, 0.04 mmol) was transferred into the reaction vessel. After 15 mins the reaction mixture was washed with HCl (1M, 2×2 mL) then with saturated aqueous NaHCO$_3$ (2×2 mL). The organic phase was then concentrated and the crude mixture was taken directly to the next reaction. LCMS (Method A) Rt 5.44 min; ESI-MS: m/z 535 [M+H]$^+$.

The BOC acylguanidine derivative from above (15 mg, 0.03 mmol) was transferred into the reaction vessel. DCM (2 mL) was transferred into the reaction vessel followed by TFA (2 mL). After 60 mins the reaction was concentrated, 0.2 ml of triethylamine was added then the reaction mixture was reconcentrated. The residue was purified by flash chromatography (DCM/MeOH (10%)/Et$_3$N (1%)) to give the title compound (12 mg). $^1$H NMR (400 MHz, CDCl$_3$) δ ppm 3.34 (s, 3H) 3.83 (t, J=8.53 Hz, 1H) 4.14 (t, J=8.21 Hz, 1H) 4.26 (d, 1H) 4.37 (d, 1H) 4.48 (t, J=9.35 Hz, 1H) 6.82 (t, J=54.57 Hz, 1H) 7.16 (t, 1H) 7.71 (d, 1H) 7.84 (d, 1H) 8.95 (s, 1H) 9.53 (s, 1H) 9.69 (br. s., 1H).

EXAMPLE 2

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-(difluoromethyl)pyrazine-2-carboxamide

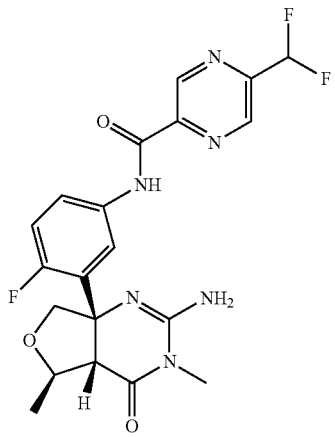 [SMILES: C[C@H]1OC[C@]2(c3cc(NC(=O)c4cnc(C(F)F)cn4)ccc3F)N=C(N)N(C)C(=O)[C@H]12]

Step 1: tert-Butyl ((3S,4R,5R)-3-(2-fluorophenyl)-4-(hydroxymethyl)-5-methyltetrahydrofuran-3-yl)carbamate

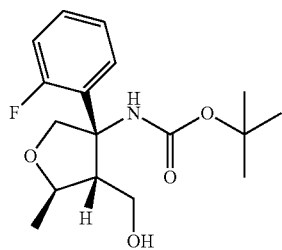 [SMILES: C[C@H]1OC[C@@](NC(=O)OC(C)(C)C)(c2ccccc2F)[C@@H]1CO]

di-tert-Butyl dicarbonate (4.0 g, 18.3 mmol) was added to a stirred solution of ((2R,3R,4S)-4-amino-4-(2-fluorophenyl)-2-methyltetrahydrofuran-3-yl)methanol (WO 2009091016, 3.75 g, 16.6 mmol) and triethylamine (2.78 mL, 20.0 mmol) in dry THF (40 mL) at RT under nitrogen. The reaction was stirred at this temperature for 3 days. The volatiles were removed in vacuo and the residue was suspended in 10% EtOAc/hexane (25 mL). The mixture was stirred at RT for 15 mins and then the solid was collected by filtration and dried in vacuo to give the title compound (4.58 g, colourless solid). $^1$H NMR (400 MHz, CDCl$_3$) δ ppm 1.32 (d, J=6.06 Hz, 3H) 1.38 (br. s., 9H) 3.55 (br. s., 0.5H) 3.69-3.94 (m, 3H) 4.06-4.25 (m, 2H) 5.81 (br. s., 0.5H) 7.02 (ddd, J=12.38, 8.34, 1.01 Hz, 1H) 7.14 (td, J=7.58, 1.26 Hz, 1H) 7.22-7.30 (m, 1H) 7.73-7.86 (m, 1H)

Step 2: (2R,3S,4S)-Methyl 4-amino-4-(2-fluorophenyl)-2-methyltetrahydrofuran-3-carboxylate

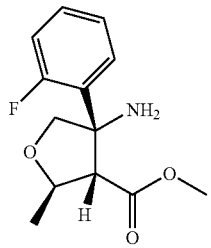 [SMILES: COC(=O)[C@@H]1[C@@H](C)OC[C@@]1(N)c1ccccc1F]

Chromium trioxide (1.38 g, 13.8 mmol) was added to a stirred solution of tert-butyl ((3S,4R,5R)-3-(2-fluorophenyl)-4-(hydroxymethyl)-5-methyltetrahydrofuran-3-yl)carbamate (4.5 g, 13.8 mmol) and sulphuric acid (1.6 mL, 30 mmol) in acetone (90 mL) and water (30 mL). The dark mixture was stirred at RT overnight. The volatiles were removed in vacuo and the residue was azeotroped with ethanol (×4) and then dried in vacuo. The residue was used without further manipulation.

Concentrated sulphuric acid (2 mL, 37 mmol) was added to a stirred solution of the crude amino acid from above in dry methanol (50 mL) at RT under nitrogen. The mixture was stirred and heated at reflux for 16 h. After cooling to RT, the volatiles were removed in vacuo and the residue was partitioned between DCM and saturated aqueous NaHCO$_3$. The aqueous layer was further extracted with DCM (×3). The combined extracts were dried (Na$_2$SO$_4$), filtered and evaporated. The residue was purified by column chromatography (normal phase, 50 g, Biotage SNAP cartridge KP-Sil, 50 mL per min, gradient 20% to 100% EtOAc in n-hexane) to give the title compound (1.27 g, light brown oil). $^1$H NMR (400 MHz, CDCl$_3$) δ ppm 1.41 (d, J=6.06 Hz, 3H) 2.00 (br. s., 2H) 3.28 (d, J=8.59 Hz, 1H) 3.71 (s, 3H) 3.94 (dd, J=9.22, 2.91 Hz, 1H) 4.31 (dd, J=9.09, 1.01 Hz, 1H) 4.57-4.64 (m, 1H) 7.07 (ddd, J=12.44, 8.15, 1.14 Hz, 1H) 7.15 (td, J=7.64, 1.14 Hz, 1H) 7.24-7.32 (m, 1H) 7.57 (td, J=8.08, 1.52 Hz, 1H).

Step 3: tert-Butyl ((4aS,5R,7aS)-7a-(2-fluorophenyl)-3,5-dimethyl-4-oxo-3,4,4a,5,7,7a-hexahydrofuro[3,4-d]pyrimidin-2-yl)carbamate

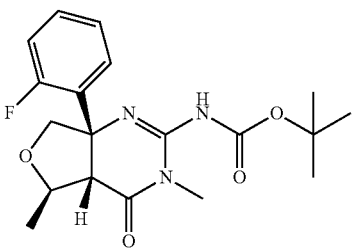 [SMILES: C[C@H]1OC[C@]2(c3ccccc3F)N=C(NC(=O)OC(C)(C)C)N(C)C(=O)[C@H]12]

tert-Butyl (methylcarbamothioyl)carbamate (2.13 g, 11.2 mmol) was added to a stirred mixture of (2R,3S,4S)-methyl 4-amino-4-(2-fluorophenyl)-2-methyltetrahydrofuran-3-carboxylate (2.27 g, 9.0 mmol), N-ethyl-N-(propan-2-yl)propan-2-amine (3.9 mL, 22.4 mmol) and N-[3-(dimethylamino)propyl]-N'-ethylcarbodiimide hydrochloride (1:1) (2.15 g, 11.2 mmol) in dry DMF (18 mL) at RT under nitrogen. The mixture was stirred at RT for 3 days, then partitioned between EtOAc (50 mL) and saturated aqueous NaHCO$_3$ (50 mL) and water (50 mL). The aqueous layer was further extracted with EtOAc (2×50 mL). The combined extracts were dried (Na₂SO₄), filtered and evaporated. The residue was purified by column chromatography (normal phase, 100 g, Biotage SNAP cartridge KP-Sil, 50 mL per min, gradient 10% to 25% EtOAc in n-hexane) to give the title compound (3.15 g, colourless foam). ¹H NMR (400 MHz, CDCl₃) δ ppm 1.51 (d, J=6.06 Hz, 3H) 1.54 (s, 9H) 3.28 (s, 3H) 3.40 (dd, J=9.09, 2.02 Hz, 1H) 4.31 (d, J=10.11 Hz, 1H) 4.36-4.45 (m, 2H) 7.10-7.24 (m, 3H) 7.33-7.40 (m, 1H) 10.53 (br. s., 1H).

Step 4: (4aS,5R,7aS)-2-Amino-7a-(2-fluoro-5-nitrophenyl)-3,5-dimethyl-4a,5,7,7a-tetrahydrofuro[3,4-d]pyrimidin-4(3H)-one

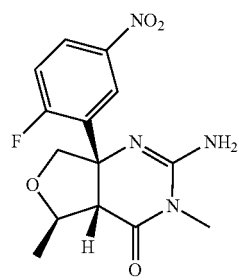 [SMILES: C[C@H]1OC[C@]2(c3cc([N+](=O)[O-])ccc3F)N=C(N)N(C)C(=O)[C@H]12]

tert-Butyl ((4aS,5R,7aS)-7a-(2-fluorophenyl)-3,5-dimethyl-4-oxo-3,4,4a,5,7,7a-hexahydrofuro[3,4-d]pyrimidin-2-yl)carbamate (2.15 g, 5.7 mmol) was taken up in fuming nitric acid (5 ml) at RT—note exotherm. The dark brown solution was stirred at RT overnight and then at 50° C. for 24 h. The reaction was allowed to cool to RT. Ice (~25 g) was added and then the mixture was basified with 50% aqueous NaOH with ice bath cooling. The pH was readjusted with saturated aqueous NH₄Cl and then the mixture was extracted with DCM (×4). The combined extracts were dried (Na₂SO₄), filtered and evaporated to give the title compound (1.8 g, yellow foam). LCMS (Method A) Rt 3.00 min; ESI-MS: m/z 323 [M+H]⁺. This material was used without further manipulation.

Step 5: tert-Butyl ((4aS,5R,7aS)-7a-(2-fluoro-5-nitrophenyl)-3,5-dimethyl-4-oxo-3,4,4a,5,7,7a-hexahydrofuro[3,4-d]pyrimidin-2-yl)(N-tert-butoxycarbonyl)carbamate

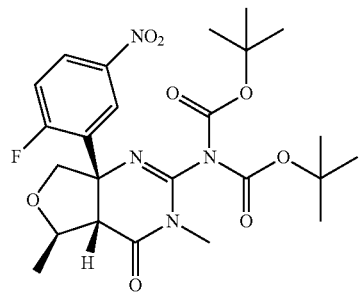

N,N-dimethylpyridin-4-amine (~2 mg) was added to a stirred solution of the (4aS,5R,7aS)-2-amino-7a-(2-fluoro-5-nitrophenyl)-3,5-dimethyl-4a,5,7,7a-tetrahydrofuro[3,4-d]pyrimidin-4(3H)-one (59 mg, 0.18 mmol), N,N-diethylethanamine (25 µL, 0.18 mmol) and di-tert-butyl dicarbonate (39 mg, 0.18 mmol) in dry THF (1.5 mL) at RT under nitrogen. The reaction was stirred at this temperature overnight. An additional portion of di-tert-butyl dicarbonate (50 mg) was added and the reaction was maintained at this temperature for 4 h. The volatiles were removed in vacuo and the residue was purified by column chromatography (normal phase, 10 g, Biotage SNAP cartridge KP-Sil, 12 mL per min, gradient 5% to 40% EtOAc in n-hexane) to give the title compound (77 mg, colourless oil). ¹H NMR (400 MHz, CDCl₃) δ ppm 1.45 (s, 9H) 1.50 (d, J=6.06 Hz, 3H) 1.54 (s, 9H) 3.16 (s, 3H) 3.21 (d, J=9.09 Hz, 1H) 4.22-4.30 (m, 1H) 4.34-4.39 (m, 1H) 4.50 (d, J=9.09 Hz, 1H) 7.21-7.26 (m, 1H) 8.19-8.25 (m, 1H) 8.44 (dd, J=6.57, 2.78 Hz, 1H)

Step 6: tert-Butyl ((4aS,5R,7aS)-7a-(5-amino-2-fluorophenyl)-3,5-dimethyl-4-oxo-3,4,4a,5,7,7a-hexahydrofuro[3,4-d]pyrimidin-2-yl)(N-tert-butoxycarbonyl)carbamate

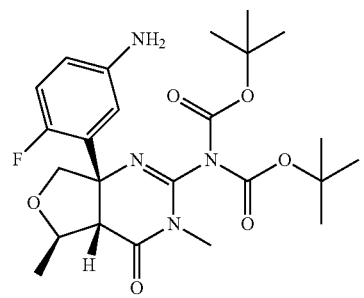 [SMILES: C[C@H]1OC[C@]2(c3cc([N+](=O)[O-])ccc3F)N=C(N(C(=O)OC(C)(C)C)C(=O)OC(C)(C)C)N(C)C(=O)[C@H]12]

A solution of tert-butyl ((4aS,5R,7aS)-7a-(2-fluoro-5-nitrophenyl)-3,5-dimethyl-4-oxo-3,4,4a,5,7,7a-hexahydrofuro[3,4-d]pyrimidin-2-yl)(N-tert-butoxycarbonyl)carbamate (77 mg) in ethanol (15 ml) was hydrogenated using the H-Cube® (ThalesNano) with full H₂ at RT and with a flow rate of 1 ml/min using Pd/C CatCart®. The resulting solution was evaporated and the residue was dried in vacuo to give the title compound (77 mg, pale yellow solid). LCMS (Method A) Rt 4.95 min. This material was used without further manipulation.

Step 7: tert-Butyl ((4aS,5R,7aS)-7a-(5-(5-(difluoromethyl)pyrazine-2-carboxamido)-2-fluorophenyl)-3,5-dimethyl-4-oxo-3,4,4a,5,7,7a-hexahydrofuro[3,4-d]pyrimidin-2-yl)(N-tert-butoxycarbonyl)carbamate

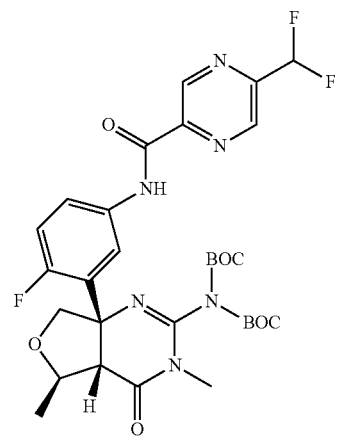 [SMILES: C[C@H]1OC[C@]2(c3cc(NC(=O)c4cnc(C(F)F)cn4)ccc3F)N=C(N(C(=O)OC(C)(C)C)C(=O)OC(C)(C)C)N(C)C(=O)[C@H]12]

A mixture of tert-butyl ((4aS,5R,7aS)-7a-(5-amino-2-fluorophenyl)-3,5-dimethyl-4-oxo-3,4,4a,5,7,7a-hexahydrofuro[3,4-d]pyrimidin-2-yl)(N-tert-butoxycarbonyl)carbamate (77 mg, 0.156 mmol), 5-(difluoromethyl)pyrazine-2-carboxylic acid (41 mg, 0.23 mmol), N-ethyl-N-(propan-2-yl)propan-2-amine (136 µl, 0.78 mmol) and (1H-benzotriazol-1-yloxy)(tripyrrolidin-1-yl)phosphonium hexafluorophosphate (122 mg, 0.23 mmol) in dry DMF (2 mL) was stirred at RT for 3 days. The mixture was partitioned between EtOAc/NaHCO₃ (aq.). The aqueous layer was extracted with EtOAc (×2). The combined extracts were washed with brine (×1), dried (Na₂SO₄), filtered and evaporated. The residue was purified by column chromatography (normal phase, 10 g, Biotage SNAP cartridge KP-Sil, 12 mL per min, gradient 5% to 50% EtOAc in n-hexane) to give the title compound (30 mg, solid). ¹H NMR (400 MHz, CDCl₃) δ ppm 1.38 (s, 9H) 1.49 (d, J=6.06 Hz, 3H) 1.54 (s, 9H) 3.16 (s, 3H) 3.50 (d, J=4.80 Hz, 1H) 4.25-4.33 (m, 1H) 4.46-4.54 (m, 2H) 6.80 (t, J=54.80 Hz, 1H) 7.15 (dd, J=10.86, 8.84 Hz, 1H) 7.56 (dd, J=6.57, 2.78 Hz, 1H) 8.05-8.11 (m, 1H) 8.84-8.89 (m, 1H) 9.53 (s, 1H) 9.65 (s, 1H).

Step 8: N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-(difluoromethyl)pyrazine-2

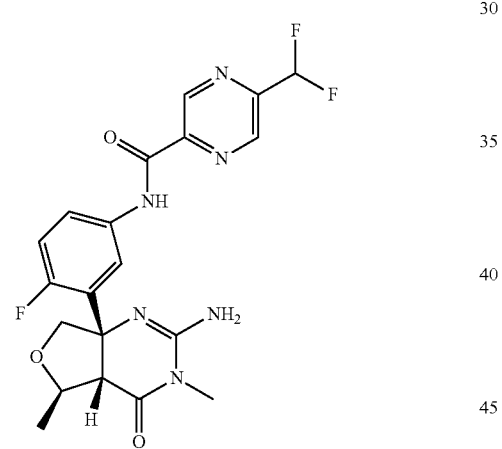

Trifluoroacetic acid (1 mL) was added to a stirred solution tert-butyl ((4aS,5R,7aS)-7a-(5-(5-(difluoromethyl)pyrazine-2-carboxamido)-2-fluorophenyl)-3,5-dimethyl-4-oxo-3,4,4a,5,7,7a-hexahydrofuro[3,4-d]pyrimidin-2-yl)(N-tert-butoxycarbonyl)carbamate (30 mg, 0.046 mmol) in DCM (2 mL) at RT. After 4 h the volatiles were removed in vacuo. The residue was azeotroped with toluene (×1) and then partitioned between DCM/NaHCO₃ (aq). The aqueous layer was extracted with DCM (×3). The combined extracts were dried by passing through a hydrophobic frit and then evaporated. The residue was triturated with Et₂O to give the title compound (18 mg) as a solid. ¹H NMR (400 MHz, MeOH-d4) δ ppm 1.42 (d, J=6.06 Hz, 3H) 3.21 (d, J=9.35 Hz, 1H) 3.23 (s, 3H) 4.23-4.32 (m, 2H) 4.33-4.37 (m, 1H) 6.88 (t, J=55.30 Hz, 1H) 7.16 (dd, J=11.49, 8.72 Hz, 1H) 7.76 (ddd, J=8.84, 4.29, 2.78 Hz, 1H) 7.82 (d, J=7.07, 2.53 Hz, 1H) 9.02 (s, 1H) 9.40 (s, 1H)

EXAMPLE 3

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methoxypyrazine-2-carboxamide

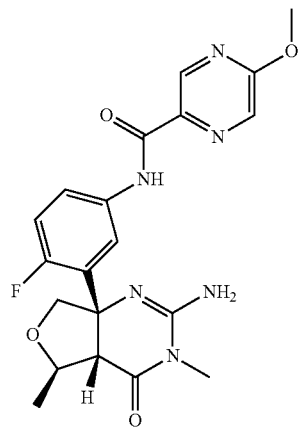 [SMILES: COc1cnc(C(=O)Nc2ccc(F)c([C@]34CO[C@H](C)[C@H]3C(=O)N(C)C(N)=N4)c2)cn1]

Step 1: tert-Butyl ((4aS,5R,7aS)-7a-(2-fluoro-5-nitrophenyl)-3,5-dimethyl-4-oxo-3,4,4a,5,7,7a-hexahydrofuro[3,4-d]pyrimidin-2-yl)carbamate

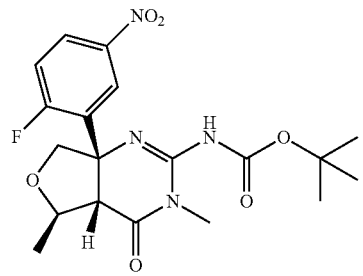 [SMILES: C[C@H]1OC[C@]2(c3cc([N+](=O)[O-])ccc3F)N=C(NC(=O)OC(C)(C)C)N(C)C(=O)[C@H]12]

A solution of di-tert-butyl dicarbonate (1.52 g, 7.0 mmol) in dry THF (5 mL) was added to a stirred solution of (4aS,5R,7aS)-2-amino-7a-(2-fluoro-5-nitrophenyl)-3,5-dimethyl-4a,5,7,7a-tetrahydrofuro[3,4-d]pyrimidin-4(3H)-one (Example 2, Step 4, 1.8 g, 5.6 mmol) and N-ethyl-N-(propan-2-yl)propan-2-amine (2.4 mL, 14.0 mmol) in dry THF (5 mL) at RT under nitrogen. The mixture was stirred at this temperature for 3 days. The volatiles were removed in vacuo and the residue was purified by column chromatography (normal phase, 100 g, Biotage SNAP cartridge KP-Sil, 50 mL per min, gradient 5% to 20 EtOAc in n-hexane) to give the title compound (1.63 g, colourless foam). ¹H NMR (400 MHz, CDCl₃) δ ppm 1.49-1.60 (m, 12H) 3.30 (s, 3H) 3.41 (dd, J=8.97, 1.89 Hz, 1H) 4.32-4.38 (m, 2H) 4.39-4.47 (m, 1H) 7.33 (dd, J=10.11, 9.09 Hz, 1H) 8.20 (dd, J=6.69, 2.65 Hz, 1H) 8.30 (ddd, J=8.84, 4.04, 2.78 Hz, 1H) 10.67 (s, 1H).

Step 2: tert-Butyl ((4aS,5R,7aS)-7a-(5-amino-2-fluorophenyl)-3,5-dimethyl-4-oxo-3,4,4a,5,7,7a-hexahydrofuro[3,4-d]pyrimidin-2-yl)carbamate

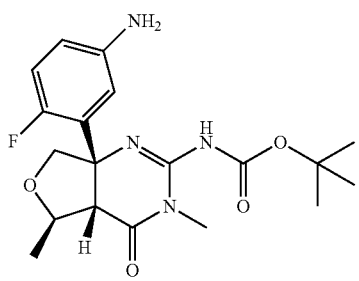

A solution of tert-butyl ((4aS,5R,7aS)-7a-(2-fluoro-5-nitrophenyl)-3,5-dimethyl-4-oxo-3,4,4a,5,7,7a-hexahydrofuro[3,4-d]pyrimidin-2-yl)carbamate (1.6 g, 3.77 mmol) in ethanol (30 ml) was hydrogenated over 10% Pd/C (200 mg) at RT under a balloon of hydrogen for 4 h. The catalyst was removed by filtration through Celite-washing with ethanol. The filtrate was evaporated to give the title compound (1.48 g, colourless foam). $^1$H NMR (400 MHz, CDCl$_3$) δ ppm 1.50 (d, J=6.06 Hz, 3H) 1.54 (s, 9H) 3.29 (s, 3H) 3.35 (dd, J=9.22, 1.89 Hz, 1H) 3.63 (s, 2H) 4.25-4.30 (m, 1H) 4.33-4.42 (m, 2H) 6.44 (dd, J=6.32, 2.78 Hz, 1H) 6.56-6.63 (m, 1H) 6.91 (dd, J=10.99, 8.72 Hz, 1H) 10.47 (br. s., 1H).

Step 3: tert-Butyl ((4aS,5R,7aS)-7a-(2-fluoro-5-(5-methoxypyrazine-2-carboxamido)phenyl)-3,5-dimethyl-4-oxo-3,4,4a,5,7,7a-hexahydrofuro[3,4-d]pyrimidin-2-yl)carbamate

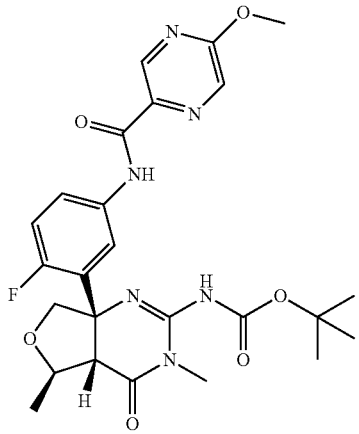 [SMILES: COc1cnc(C(=O)Nc2ccc(F)c([C@]34CO[C@H](C)[C@H]3C(=O)N(C)C(NC(=O)OC(C)(C)C)=N4)c2)cn1]

N-Ethyl-N-(propan-2-yl)propan-2-amine (0.33 mL, 1.9 mmol) was added to a stirred mixture of tert-butyl ((4aS,5R,7aS)-7a-(5-amino-2-fluorophenyl)-3,5-dimethyl-4-oxo-3,4,4a,5,7,7a-hexahydrofuro[3,4-d]pyrimidin-2-yl)carbamate (150 mg, 0.38 mmol), 5-methoxypyrazine-2-carboxylic acid (89 mg, 0.57 mmol) and (1H-benzotriazol-1-yloxy)(tripyrrolidin-1-yl)phosphonium hexafluorophosphate (300 mg, 0.57 mmol) in dry DCM (2 mL). The mixture was stirred at RT overnight. The reaction mixture was partitioned between DCM and NaHCO$_3$ (aq). The aqueous layer was extracted with DCM (×2). The combined extracts were dried by passing through a hydrophobic frit and then evaporated. The residue was purified by column chromatography (normal phase, 10 g, Biotage SNAP cartridge KP-Sil, 12 mL per min, gradient 5% to 30% EtOAc in n-hexane) to give the title compound (213 mg, foam). $^1$H NMR (400 MHz, CDCl$_3$) δ ppm 1.52 (d, J=6.06 Hz, 3H) 1.56 (s, 9H) 3.31 (s, 3H) 3.44 (dd, J=9.09, 1.77 Hz, 1H) 4.08 (s, 3H) 4.31 (d, J=9.85 Hz, 1H) 4.37-4.47 (m, 2H) 7.16 (dd, J=10.74, 8.97 Hz, 1H) 7.54 (dd, J=6.82, 2.53 Hz, 1H) 7.84 (ddd, J=8.78, 4.23, 2.65 Hz, 1H) 8.15 (d, J=1.26 Hz, 1H) 9.01 (d, J=1.26 Hz, 1H) 9.49 (s, 1H) 10.60 (s, 1H).

Step 4: N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methoxypyrazine-2-carboxamide

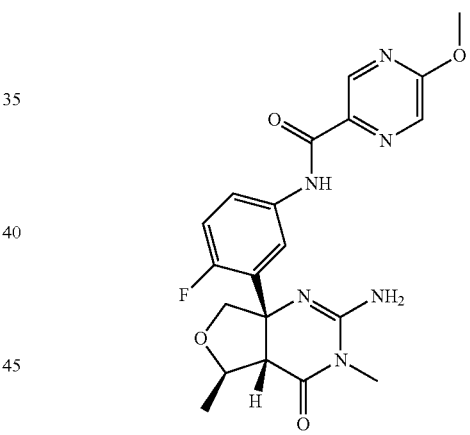

Trifluoroacetic acid (1 ml) was added to a stirred solution of tert-butyl ((4aS,5R,7aS)-7a-(2-fluoro-5-(5-methoxypyrazine-2-carboxamido)phenyl)-3,5-dimethyl-4-oxo-3,4,4a,5,7,7a-hexahydrofuro[3,4-d]pyrimidin-2-yl)carbamate (210 mg, 0.40 mmol) in DCM (2 mL) at RT. The mixture was stirred at RT for 1 h. The reaction mixture was evaporated and the residue was loaded on to a SCX cartridge (5 g). The cartridge was eluted with methanol (2×20 mL) and then 2M NH$_3$ in MeOH (1×20 mL). The ammonia-methanol fraction was evaporated. The residue was treated with Et$_2$O/hexanes and the resulting solid was collected by filtration and dried in vacuo to give the title compound (105 mg, colourless solid). $^1$H NMR (400 MHz, DMSO-d6) δ ppm 1.31 (d, J=6.06 Hz, 3H) 2.99 (d, J=8.84 Hz, 1H) 3.10 (s, 3H) 4.02 (s, 3H) 4.05-4.14 (m, 1H) 4.14-4.22 (m, 2H) 6.04 (br. s., 2H) 7.16 (dd, J=10.99, 9.22 Hz, 1H) 7.70-7.83 (m, 2H) 8.41 (d, J=1.26 Hz, 1H) 8.88 (d, J=1.26 Hz, 1H) 10.58 (s, 1H).

EXAMPLE 4

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-methylpyrazine-2-carboxamide

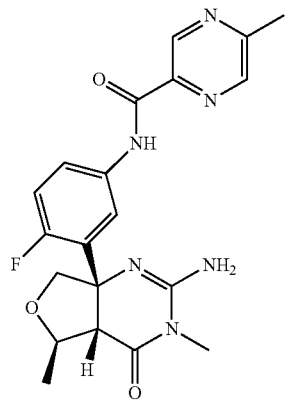 [SMILES: Cc1cnc(C(=O)Nc2ccc(F)c([C@]34CO[C@H](C)[C@H]3C(=O)N(C)C(N)=N4)c2)cn1]

This compound was prepared using the procedures described in Example 3, Steps 3 and 4, substituting 5-methylpyrazine-2-carboxylic acid for 5-methoxypyrazine-2-carboxylic acid. $^1$H NMR (400 MHz, DMSO-d6) δ ppm 1.31 (d, J=5.81 Hz, 3H) 2.63 (s, 3H) 2.98 (d, J=8.59 Hz, 1H) 3.10 (s, 3H) 4.01-4.13 (m, 1H) 4.17 (s, 2H) 6.02 (br. s., 2H) 7.17 (dd, J=10.61, 9.60 Hz, 1H) 7.70-7.86 (m, 2H) 8.67-8.72 (m, 1H) 9.15 (d, J=1.01 Hz, 1H) 10.76 (br. s., 1H)

EXAMPLE 5

N-(3-((4aS,5R,7aS)-2-Amino-3,5-dimethyl-4-oxo-3,4,4a,5,7,7a-hexahydrofuro[3,4-d]pyrimidin-7a-yl)-4-fluorophenyl)-5-methylpicolinamide

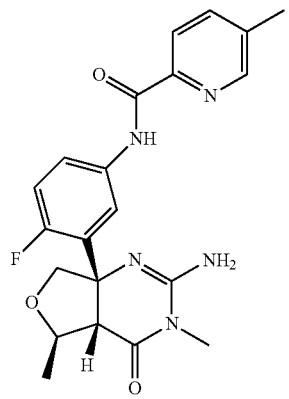 [SMILES: Cc1ccc(C(=O)Nc2ccc(F)c([C@]34CO[C@H](C)[C@H]3C(=O)N(C)C(N)=N4)c2)nc1]

This compound was prepared using the procedures described in Example 3, Steps 3 and 4, substituting 5-methylpyridine-2-carboxylic acid for 5-methoxypyrazine-2-carboxylic acid. $^1$H NMR (400 MHz, MeOH-d4) δ ppm 1.42 (d, J=6.06 Hz, 3H) 2.45 (s, 3H) 3.19-3.25 (m, 4H) 4.22-4.37 (m, 3H) 7.14 (dd, J=11.37, 8.84 Hz, 1H) 7.73 (ddd, J=8.84, 4.29, 2.78 Hz, 1H) 7.78 (dd, J=7.07, 2.53 Hz, 1H) 7.80-7.84 (m, 1H) 8.08 (d, J=7.83 Hz, 1H) 8.53 (s, 1H)

EXAMPLE 6

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-(trifluoromethyl)picolinamide

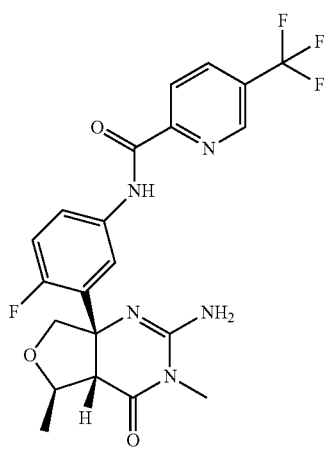 [SMILES: C[C@H]1OC[C@]2(c3cc(NC(=O)c4ccc(C(F)(F)F)cn4)ccc3F)N=C(N)N(C)C(=O)[C@H]12]

This compound was prepared using the procedures described in Example 3, Steps 3 and 4, substituting 5-(trifluoromethyl)picolinic acid for 5-methoxypyrazine-2-carboxylic acid. $^1$H NMR (400 MHz, MeOH-d4) δ ppm 1.42 (d, J=6.06 Hz, 3H) 3.19-3.25 (m, 4H) 4.22-4.31 (m, 2H) 4.32-4.37 (m, 1H) 7.16 (dd, J=11.62, 8.84 Hz, 1H) 7.76 (ddd, J=8.72, 4.17, 2.78 Hz, 1H) 7.82 (dd, J=6.95, 2.65 Hz, 1H) 8.33-8.41 (m, 2H) 9.02 (s, 1H)

EXAMPLE 7

N-(3-((4aS,5R,7aS)-2-amino-3,5-dimethyl-4-oxo-3,4,4a,5,7,7a-hexahydrofuro[3,4-d]pyrimidin-7a-yl)-4-fluorophenyl)-5-cyanopicolinamide

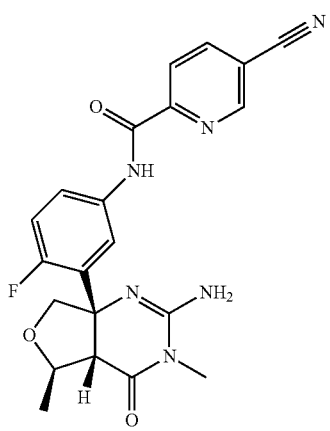 [SMILES: C[C@H]1OC[C@]2(c3cc(NC(=O)c4ccc(C#N)cn4)ccc3F)N=C(N)N(C)C(=O)[C@H]12]

This compound was prepared using the procedures described in Example 3, Steps 3 and 4, substituting 5-cyanopicolinic acid for 5-methoxypyrazine-2-carboxylic acid. $^1$H NMR (400 MHz, MeOH-d4) δ ppm 1.42 (d, J=6.06 Hz, 3H)

3.18-3.24 (m, 4H) 4.22-4.31 (m, 2H) 4.32-4.36 (m, 1H) 7.15 (dd, J=11.37, 8.84 Hz, 1H) 7.75 (ddd, J=8.84, 4.29, 2.78 Hz, 1H) 7.81 (dd, J=7.07, 2.53 Hz, 1H) 8.34 (dd, J=8.21, 0.88 Hz, 1H) 8.41 (dd, J=8.08, 2.02 Hz, 1H) 9.04 (dd, J=1.89, 0.88 Hz, 1H)

EXAMPLE 8

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide

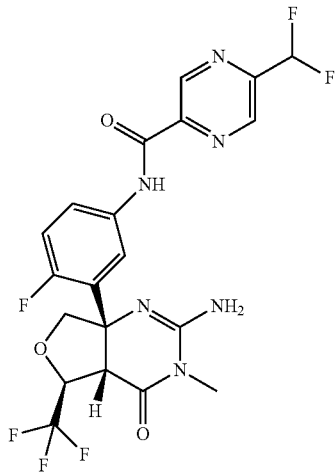

Step 1: tert-Butyl {[(2S)-1,1,1-trifluorobut-3-en-2-yl]oxy}acetate

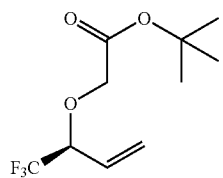

To a solution of trimethylsulfonium iodide (110 g) in THF (500 mL) at −30° C. was added lithium hexamethyldisilazide (530 mL, 1N in THF) portionwise over 45 mins. After stirring at −20° C. for 20 mins, (S)-2-trifluoromethyloxirane (37.97 g) was added at the same temperature over 15 mins, and the mixture was allowed to warm to RT and stirred for 3 h. The slurry was then added portionwise to an ice-cold solution of tert-butyl bromoacetate (105.68 g) in NMP (200 mL). The resulting mixture was allowed to warm to RT and stir for 2 days, before dilution with EtOAc (1 L). The organic layer was washed with sodium bicarbonate (sat., aq., 4×400 mL), dried over MgSO$_4$ and evaporated. The residue was purified by silica gel column chromatography (5% EtOAc in hexanes) to obtain the title compound (70.1 g) which was used in the subsequent step without purification. $^1$H NMR (400 MHz, CDCl$_3$) δ ppm: 1.30 (s, 9H) 3.83-3.96 (m, 2H) 4.14-4.21 (m, 1H) 5.34-5.48 (m, 2H) 5.56-5.71 (m, 1H)

Step 2: (S)—N-Methoxy-N-methyl-2-((1,1,1-trifluorobut-3-en-2-yl)oxy)acetamide

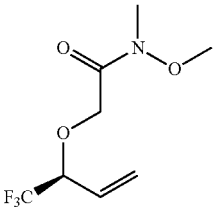

tert-Butyl {[(2S)-1,1,1-trifluorobut-3-en-2-yl]oxy}acetate (70.1 g, crude) was dissolved in ice-cold formic acid (200 mL). The mixture was allowed to warm to RT and stir overnight. The reaction mixture was then concentrated under reduced pressure, toluene (200 mL) was added, the mixture concentrated, before a second addition of toluene (200 mL) and concentration to an oil. The residue was dissolved in DCM (600 mL), cooled in an ice-bath, and N,N'-carbonyl diimidazole (35 g) was added portionwise over 20 mins. After stirring for 45 mins, N,O-dimethyl hydroxylamine hydrochloride (22 g) was added, and the reaction mixture was allowed to warm to RT and stir overnight. Saturated NaHCO$_3$ (500 mL) and brine (250 mL) were then added, and the mixture extracted with EtOAc (3×750 mL). The combined organic portions were dried over MgSO$_4$ and evaporated. The residue was purified by silica gel column chromatography (1% to 30% EtOAc in hexanes) to obtain the title compound (25.17 g). $^1$H NMR (400 MHz, CDCl$_3$) δ ppm 3.21 (s, 3H), 3.71 (m, 3H), 4.36-4.51 (m, 3H), 5.54-5.69 (m, 2H), 5.84 (ddd, J=17.7, 10.4, 7.3 Hz, 1H)

Step 3: (S)-1-(2-Fluorophenyl)-2-((1,1,1-trifluorobut-3-en-2-yl)oxy)ethanone

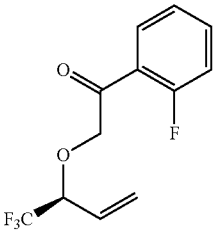 [SMILES: C=C[C@H](OCC(=O)c1ccccc1F)C(F)(F)F]

A solution of n-butyllithium in hexane (2.50 M; 90 mL) was added dropwise over 25 mins to a solution containing 2-bromofluorobenzene (40.35 g) in THF (250 mL) under a N$_2$ atmosphere at −78° C. The reaction solution was allowed to warm to −60° C. and stir for 60 min. (S)—N-methoxy-N-methyl-2-((1,1,1-trifluorobut-3-en-2-yl)oxy)acetamide (40 g) in THF (25 mL) was added dropwise to the reaction solution, and after stirring at −60° C. for 2 h, aqueous NH$_4$Cl (100 mL) was added to the reaction solution, followed by warming to RT. Brine (200 mL) was added to the reaction solution, and the mixture was extracted with EtOAc (3×400 mL). The combined organic portions were dried over MgSO$_4$, evaporated, and the residue was purified by silica gel column chromatography (1% to 10% EtOAc in hexanes) to obtain the title compound (33.59 g). ¹H NMR (400 MHz, CDCl₃) δ ppm: 4.40 (pentet, J=6.3 Hz, 1H) 4.81-4.87 (m, 2H), 5.54-5.69 (m, 2H), 5.86 (ddd, J 17.4, 10.4, 7.3 Hz, 1H) 7.12-7.22 (m, 1H) 7.24-7.34 (m, 1H) 7.54-7.63 (m, 1H) 7.94-8.02 (m, 1H).

Step 4: (S)-1-(2-Fluorophenyl)-2-((1,1,1-trifluorobut-3-en-2-yl)oxy)ethanone oxime

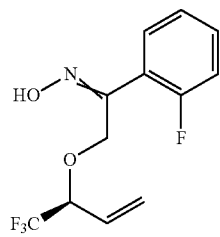 [SMILES: C=C[C@H](OCC(=NO)c1ccccc1F)C(F)(F)F]

(S)-1-(2-Fluorophenyl)-2-((1,1,1-trifluorobut-3-en-2-yl)oxy)ethanone (41.22 g) was dissolved in anhydrous methanol (400 mL) and hydroxylamine hydrochloride (14.0 g) and sodium acetate (19.0 g) were added. The reaction mixture was heated to 50° C. for 90 min, then cooled to RT, concentrated in vacuo and the residue purified by silica gel chromatography (2% to 15% EtOAc in hexanes) to afford the title compound as a mixture of geometric isomers. ¹H NMR (400 MHz, CDCl₃) δ ppm: 4.04-4.15 (m, 0.8H), 4.18-4.26 (s, 0.2H), 4.44-4.57 (m, 0.4H) 4.79-4.90 (m, 1.6H) 5.37-5.56 (m, 2H) 5.64-5.78 (m, 1H) 7.03-7.26 (m, 2H) 7.33-7.54 (m, 2H), 7.90 (br.s s, 0.2H), 8.51 (br s, 0.8H).

Step 5: (3aR,4S)-4-(Trifluoromethyl)-3,3a,4,6-tetrahydrofuro[3,4-c]isoxazole

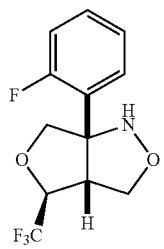

(S)-1-(2-Fluorophenyl)-2-((1,1,1-trifluorobut-3-en-2-yl)oxy)ethanone oxime (40.54 g) was dissolved in xylenes (400 mL) and hydroquinone (4.0 g) was added. The reaction mixture was heated to reflux (heating block temperature 140° C.) for 22 hrs, then cooled and evaporated. The residue was purified by silica gel column chromatography (1% to 30% EtOAc in hexanes) to obtain the title compound (28.76 g). ¹H NMR (400 MHz, CDCl₃) δ ppm: 3.71-3.81 (m, 1H), 4.04-4.35 (m, 3H), 4.51-4.62 (m, 1H), 5.38-5.54 (m, 1H), 7.07-7.26 (m, 2H), 7.32-7.42 (m, 1H), 7.54-7.67 (m, 1H).

Step 6: ((2S,3R,4S)-4-Amino-4-(2-fluorophenyl)-2-(trifluoromethyl)tetrahydrofuran-3

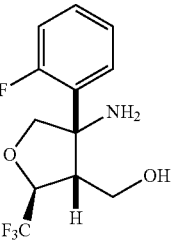

(3aR,4S)-4-(Trifluoromethyl)-3,3a,4,6-tetrahydrofuro[3,4-c]isoxazole (28.76 g) was dissolved in acetic acid (200 mL) and the reaction mixture cooled to 0° C. Zinc (50 g) was added, and the reaction was allowed to warm and stir at RT. The reaction mixture was then diluted with EtOAc (500 mL) and filtered through celite, washing with a further 500 mL of EtOAc. The combined organic portions were evaporated, dissolved in chloroform (200 mL), and ammonia (28% aq., 250 mL) was added slowly. The layers were separated, and the aqueous portion was further extracted with chloroform (2×250 mL). The combined organic extracts were dried over anhydrous MgSO₄ and evaporated to afford the title compound (31.12 g) which was used in the subsequent step without further purification. ¹H NMR (400 MHz, CDCl₃) δ ppm: 2.93 (ddd, J=7.7, 4.9, 2.5 Hz, 1H), 3.84 (dd, J=12.4, 4.8 Hz, 1H), 4.05 (dd, J=9.2, 3.2 Hz, 1H), 4.17 (dd, J=12.4, 2.3 Hz, 1H), 4.31 (d, J=9.3 Hz, 1H), 4.72 (quin, J=7.3 Hz, 1H), 7.13 (ddd, J=13.1, 8.8, 1.3 Hz, 1H), 7.22 (td, J=7.6, 1.3 Hz, 1H), 7.31-7.40 (m, 1H), 7.51 (td, J=8.0, 1.6 Hz, 1H)

Step 7: (2S,3S,4S)-Methyl 4-amino-4-(2-fluorophenyl)-2-(trifluoromethyl) tetrahydrofuran-3-carboxylate

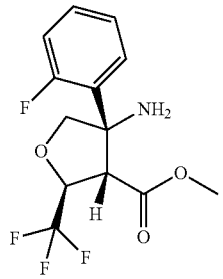 [SMILES: COC(=O)[C@@H]1[C@@H](C(F)(F)F)OC[C@@]1(N)c1ccccc1F]

Sulphuric acid (1.05 mL, 19.7 mmol) was added to a stirred mixture of ((2S,3R,4S)-4-amino-4-(2-fluorophenyl)-2-(trifluoromethyl)tetrahydrofuran-3-yl)methanol (2.5 g, 9.0 mmol) and chromium trioxide (0.98 g, 9.8 mmol) in acetone/water (3:1, 20 mL). The reaction was stirred at RT for 3 days. The volatiles were removed in vacuo. The residue was azeotroped with ethanol (×2) and then dried under vacuum to give the crude amino acid which was used without further manipulation.

Sulfuric acid (1 mL, 18.9 mmol) was added to a stirred mixture of the crude amino acid from above in dry methanol (20 mL), at RT under nitrogen. The mixture was stirred and heated at reflux for 16 h. The reaction was allowed to cool and additional sulfuric acid (1 mL) was added and then the mixture was stirred and heated at reflux for 48 h. [Additional sulfuric acid was added as required to drive the reaction to completion] The mixture was allowed to cool and the methanol was removed in vacuo. The residue was diluted with water and basified with $K_2CO_3$ (s). The mixture was extracted with DCM (×4). The combined extracts were dried by passing through a hydrophobic frit and then evaporated. The residue was purified by column chromatography (normal phase, 50 g, Biotage SNAP cartridge KP-Sil, 50 mL per min, gradient 0% to 50% EtOAc in n-hexane) to give the title compound (2.0 g, pale yellow oil). $^1$H NMR (400 MHz, CDCl$_3$) δ ppm 1.94 (br. s., 2H) 3.72 (s, 3H) 3.97 (dd, J=7.58, 1.26 Hz, 1H) 4.05 (dd, J=8.97, 2.40 Hz, 1H) 4.36 (d, J=8.84 Hz, 1H) 5.02 (quin, J=7.14 Hz, 1H) 7.11 (dd, J=12.63, 8.08 Hz, 1H) 7.19 (t, J=1.00 Hz, 1H) 7.30-7.38 (m, 1H) 7.66 (td, J=8.08, 1.52 Hz, 1H).

Step 8: tert-butyl ((4aS,5S,7aS)-7a-(5-amino-2-fluorophenyl)-3-methyl-4-oxo-5-(trifluoromethyl)-3,4,4a,5,7,7a-hexahydrofuro[3,4-d]pyrimidin-2-yl)carbamate

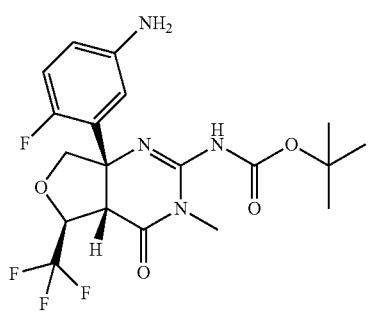 [SMILES: CN1C(=O)[C@@H]2[C@@H](C(F)(F)F)OC[C@]2(c2cc(N)ccc2F)N=C1NC(=O)OC(C)(C)C]

This material was prepared by analogy with the procedures described in example 2 (steps 3 and 4) and example 3 (steps 1 and 2) substituting (2S,3S,4S)-methyl 4-amino-4-(2-fluorophenyl)-2-(trifluoromethyl) tetrahydrofuran-3-carboxylate for (2R,3S,4S)-methyl 4-amino-4-(2-fluorophenyl)-2-methyltetrahydrofuran-3-carboxylate. $^1$H NMR (400 MHz, CDCl$_3$) δ ppm 1.54 (s, 9H) 3.33 (s, 3H) 3.68 (s, 2H) 3.98 (d, J=7.83 Hz, 1H) 4.31 (d, J=9.85 Hz, 1H) 4.45 (dd, J=9.85, 3.28 Hz, 1H) 4.51-4.59 (m, 1H) 6.46 (dd, J=6.32, 2.78 Hz, 1H) 6.61-6.67 (m, 1H) 6.94 (dd, J=11.12, 8.84 Hz, 1H) 10.50 (br. s., 1H)

Step 9: tert-Butyl ((4aS,5S,7aS)-7a-(5-(5-(difluoromethyl)pyrazine-2-carboxamido)-2-fluorophenyl)-3-methyl-4-oxo-5-(trifluoromethyl)-3,4,4a,5,7,7a-hexahydrofuro[3,4-d]pyrimidin-2-yl)carbamate

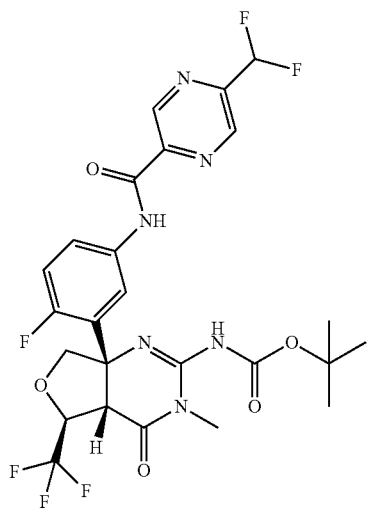 [SMILES: CN1C(=O)[C@@H]2[C@@H](C(F)(F)F)OC[C@]2(c2cc(NC(=O)c3cnc(C(F)F)cn3)ccc2F)N=C1NC(=O)OC(C)(C)C]

N-Ethyl-N-(propan-2-yl)propan-2-amine (300 μL, 1.7 mmol) was added to a stirred mixture of tert-butyl ((4aS,5S,7aS)-7a-(5-amino-2-fluorophenyl)-3-methyl-4-oxo-5-(trifluoromethyl)-3,4,4a,5,7,7a-hexahydrofuro[3,4-d]pyrimidin-2-yl)carbamate amine (150 mg, 0.34 mmol), 5-(difluoromethyl)pyrazine-2-carboxylic acid (90 mg, 0.50 mmol) and (1H-benzotriazol-1-yloxy)(tripyrrolidin-1-yl)phosphonium hexafluorophosphate (265 mg, 0.50 mmol) in dry DCM (2 mL) at RT under nitrogen. The reaction was stirred at this temperature for 16 h, then partitioned between DCM and NaHCO$_3$ (aq). The aqueous layer was extracted with DCM (×2). The combined extracts were dried by passing through a hydrophobic frit and then evaporated. The residue was purified by column chromatography (normal phase, 25 g, Biotage SNAP cartridge KP-Sil, 25 mL per min, gradient 5% to 30% EtOAc in n-hexane) to give the title compound (92 mg, light yellow solid). $^1$H NMR (400 MHz, CDCl$_3$) δ ppm 1.58 (s, 9H) 3.36 (s, 3H) 4.06 (d, J=7.83 Hz, 1H) 4.40 (d, J=9.85 Hz, 1H) 4.50 (dd, J=9.73, 2.91 Hz, 1H) 4.57-4.65 (m, 1H) 6.81 (t, J=54.60 Hz, 1H) 7.22 (dd, J=10.86, 9.09 Hz, 1H) 7.74 (dd, J=6.69, 2.65 Hz, 1H) 7.84 (ddd, J=8.84, 4.17, 2.65 Hz, 1H) 8.93 (s, 1H) 9.52 (s, 1H) 9.65 (s, 1H) 10.64 (s, 1H)

Step 10: N-(3-((4aS,5S,7aS)-2-Amino-3-methyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide

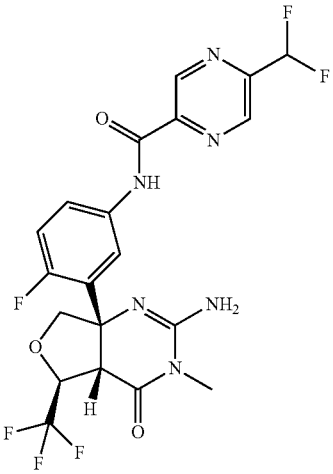 [SMILES: CN1C(=O)[C@@H]2[C@@H](C(F)(F)F)OC[C@]2(c2cc(NC(=O)c3cnc(C(F)F)cn3)ccc2F)N=C1N]

Trifluoroacetic acid (1 mL) was added to a stirred solution of tert-butyl ((4aS,5S,7aS)-7a-(5-(5-(difluoromethyl)pyrazine-2-carboxamido)-2-fluorophenyl)-3-methyl-4-oxo-5-(trifluoromethyl)-3,4,4a,5,7,7a-hexahydrofuro[3,4-d]pyrimidin-2-yl)carbamate (92 mg, 0.15 mmol) in DCM (2 mL) at RT. After 1 h at this temperature the volatiles were removed in vacuo and the residue was azeotroped with PhMe (×2). The residue was then taken up in MeOH and loaded on to a SCX cartridge (5 g). The cartridge was eluted with MeOH (2×20 mL) and then 2M $NH_3$ in MeOH (2×20 mL). The relevant fraction was evaporated to give the title compound (72 mg, beige solid). $^1$H NMR (400 MHz, MeOH-d4) δ ppm 3.25 (s, 3H) 3.80 (d, J=8.34 Hz, 1H) 4.29-4.34 (m, 1H) 4.35-4.40 (m, 1H) 4.62-4.71 (m, 1H) 6.95 (t, J=54.30 Hz, 1H) 7.18 (dd, J=11.62, 8.84 Hz, 1H) 7.80 (ddd, J=8.72, 4.17, 2.78 Hz, 1H) 7.89 (dd, J=6.82, 2.53 Hz, 1H) 9.02 (s, 1H) 9.40 (s, 1H).

EXAMPLE 9

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methoxypyrazine-2-carboxamide

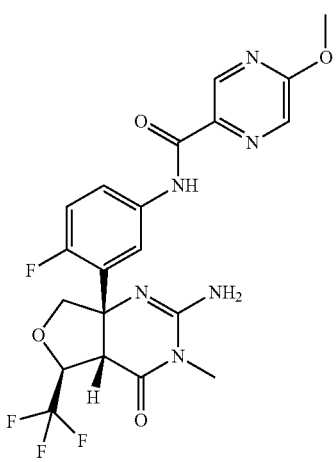 [SMILES: COc1cnc(C(=O)Nc2ccc(F)c([C@]34CO[C@H](C(F)(F)F)[C@H]3C(=O)N(C)C(N)=N4)c2)cn1]

This compound was prepared using the procedures described in Example 8, Steps 9 and 10, substituting 5-methoxypyrazine-2-carboxylic acid for 5-(difluoromethyl)pyrazine-2-carboxylic acid. $^1$H NMR (400 MHz, MeOH-d4) δ ppm 3.25 (s, 3H) 3.80 (d, J=8.34 Hz, 1H) 4.07 (s, 3H) 4.31 (dd, J=8.34, 2.27 Hz, 1H) 4.37 (d, J=8.08 Hz, 1H) 4.66 (quin, J=7.14 Hz, 1H) 7.16 (dd, J=11.62, 8.84 Hz, 1H) 7.74 (ddd, J=8.84, 4.29, 2.78 Hz, 1H) 7.84 (dd, J=7.07, 2.53 Hz, 1H) 8.28 (d, J=1.26 Hz, 1H) 8.90 (d, J=1.26 Hz, 1H)

EXAMPLE 10

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methylpicolinamide

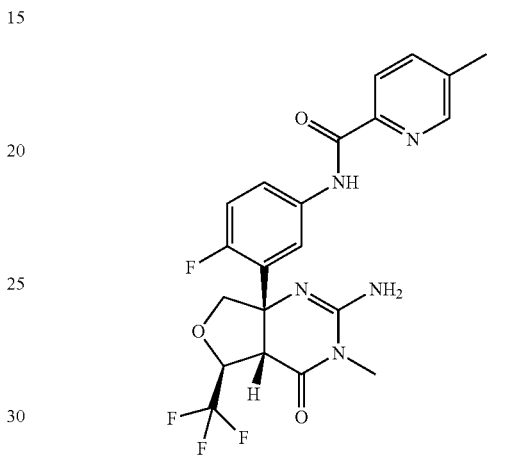

This compound was prepared using the procedures described in Example 8, Steps 9 and 10, substituting 5-methylpyridine-2-carboxylic acid for 5-(difluoromethyl)pyrazine-2-carboxylic acid. $^1$H NMR (400 MHz, MeOH-d4) δ ppm 2.45 (s, 3H) 3.25 (s, 3H) 3.81 (d, J=8.34 Hz, 1H) 4.32 (dd, J=8.34, 2.27 Hz, 1H) 4.37 (d, J=8.34 Hz, 1H) 4.62-4.72 (m, 1H) 7.16 (dd, J=11.62, 8.84 Hz, 1H) 7.76 (ddd, J=8.78, 4.23, 2.65 Hz, 1H) 7.79-7.90 (m, 2H) 8.08 (d, J=7.83 Hz, 1H) 8.53 (s, 1H).

EXAMPLE 11

N-(3-((4aS,5S,7aS)-2-Amino-3-methyl-4-oxo-5-(trifluoromethyl)-3,4,4a,5,7,7a-hexahydrofuro[3,4-d]pyrimidin-7a-yl)-4-fluorophenyl)-5-cyanopicolinamide

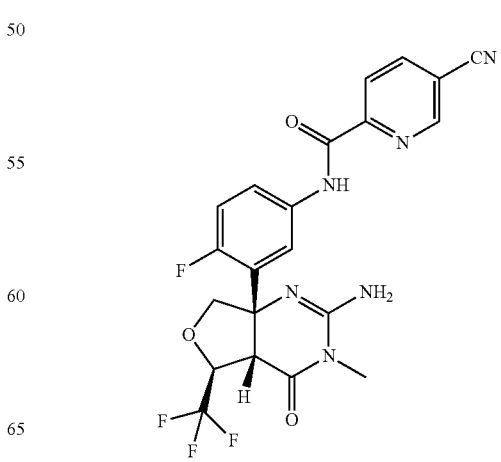

This compound was prepared using the procedures described in Example 8, Steps 9 and 10, substituting 5-cyanopicolinic acid for 5-(difluoromethyl)pyrazine-2-carboxylic acid. ¹H NMR (400 MHz, MeOH-d4) δ ppm 3.25 (s, 3H) 3.79 (d, J=8.34 Hz, 1H) 4.29-4.34 (m, 1H) 4.35-4.40 (m, 1H) 4.58-4.72 (m, 1H) 7.18 (dd, J=11.49, 8.97 Hz, 1H) 7.79 (ddd, J=8.84, 4.29, 2.78 Hz, 1H) 7.88 (dd, J=6.95, 2.40 Hz, 1H) 8.34 (dd, J=8.34, 1.01 Hz, 1H) 8.41 (dd, J=8.30, 2.00 Hz, 1H) 9.01-9.07 (m, 1H)

EXAMPLE 12

N-(3-((4aS,5S,7aS)-2-Amino-3-ethyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide

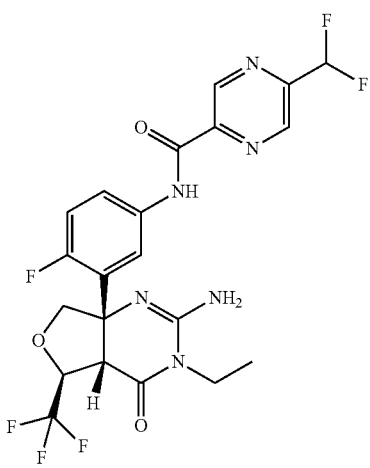 [SMILES: CCN1C(=O)[C@@H]2[C@@H](C(F)(F)F)OC[C@]2(c2cc(NC(=O)c3cnc(C(F)F)cn3)ccc2F)N=C1N]

Step 1: tert-Butyl (ethylcarbamothioyl)carbamate

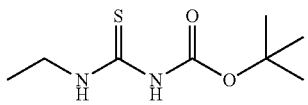

This material was prepared by analogy with the procedure for the preparation of tert-butyl (methylcarbamothioyl)carbamate (Andreani et al, Synthetic Communications 2008, 38, 3834-39).

A solution of tert-butyl carbamate (5.0 g, 42.7 mmol) and isothiocyanatoethane (3.7 mL, 42.7 mmol) in dry DMF (30 mL) was added slowly to a stirred solution of sodium hydride (60% suspension, 1.9 g, 47 mmol) in dry DMF (15 mL) under nitrogen, such that the internal temperature was maintained <5° C. After complete addition the reaction was stirred in an ice bath for 1 h. The cooling bath was removed and the reaction was stirred at RT overnight, and then poured on to ice (25 g) and diluted with water (150 mL). The aqueous mixture was extracted with Et₂O (3×100 mL). The combined extracts were washed with brine (1×50 mL), dried (MgSO₄), filtered and evaporated. The residue was purified by column chromatography (normal phase, 100 g, Biotage SNAP cartridge KP-Sil, 50 mL per min, gradient 4% to 8% EtOAc in n-hexane) to give the title compound (6.0 g, colourless solid). ¹H NMR (400 MHz, CDCl₃) δ ppm 1.29 (t, J=7.33 Hz, 3H) 1.50 (s, 9H) 3.54-3.78 (m, 2H) 7.82 (br. s., 1H) 9.63 (br. s., 1H).

Step 2: tert-Butyl ((4aS,5S,7aS)-3-ethyl-7a-(2-fluorophenyl)-4-oxo-5-(trifluoromethyl)-3,4,4a,5,7,7a-hexahydrofuro[3,4-d]pyrimidin-2-yl)carbamate

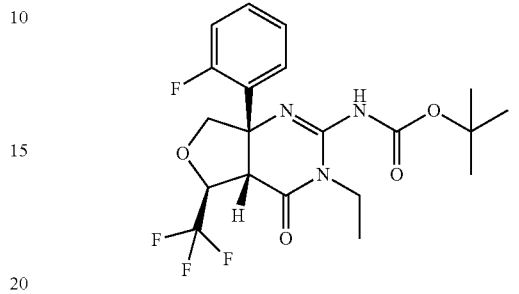

tert-Butyl (ethylcarbamothioyl)carbamate (290 mg, 1.4 mmol) was added to a stirred mixture of (2S,3S,4S)-methyl 4-amino-4-(2-fluorophenyl)-2-(trifluoromethyl) tetrahydrofuran-3-carboxylate (290 mg, 0.94 mmol), N-ethyl-N-(propan-2-yl)propan-2-amine (410 µL, 2.4 mmol) and N-[3-(dimethylamino)propyl]-N'-ethylcarbodiimide hydrochloride (1:1) (230 mg, 1.2 mmol) in dry DMF (1 mL) at RT under nitrogen. The mixture was then stirred and heated at 50° C. for 1.5 h and then allowed to stand at RT overnight. The reaction mixture was partitioned between EtOAc and NaHCO₃ (aq.). The aqueous layer was extracted with EtOAc (×2). The combined extracts were washed with brine (×1), dried (Na₂SO₄), filtered and evaporated. The residue was purified by column chromatography (normal phase, 25 g, Biotage SNAP cartridge KP-Sil, 25 mL per min, gradient 4% to 15% EtOAc in n-hexane) to give the title compound (301 mg, colourless foam). ¹H NMR (400 MHz, CDCl₃) δ ppm 1.12 (t, J=7.07 Hz, 3H) 1.54 (s, 9H) 3.92-4.03 (m, 2H) 4.03-4.11 (m, 1H) 4.37 (d, J=9.60 Hz, 1H) 4.48 (dd, J=9.60, 3.28 Hz, 1H) 4.51-4.59 (m, 1H) 7.13-7.26 (m, 3H) 7.38-7.45 (m, 1H) 10.55 (br. s., 1H)

Step 3: (4aS,5S,7aS)-2-Amino-3-ethyl-7a-(2-fluoro-5-nitrophenyl)-5-(trifluoromethyl)-4a,5,7,7a-tetrahydrofuro[3,4-d]pyrimidin-4(3H)-one

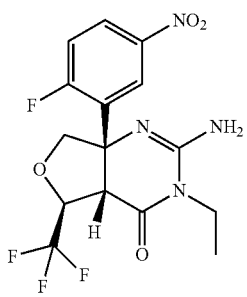 [SMILES: CCN1C(=O)[C@@H]2[C@@H](C(F)(F)F)OC[C@]2(c2cc([N+](=O)[O-])ccc2F)N=C1N]

tert-Butyl ((4aS,5S,7aS)-3-ethyl-7a-(2-fluorophenyl)-4-oxo-5-(trifluoromethyl)-3,4,4a,5,7,7a-hexahydrofuro[3,4-d]pyrimidin-2-yl)carbamate (300 mg, 0.67 mmol) was taken up in fuming nitric acid (2 mL) at RT. The mixture was stirred at RT for 24 h, then poured on to ice and basified slowly with 50% aq. NaOH (~3 mL). The aqueous mixture was extracted with DCM (×4). The combined extracts were dried by passing through a hydrophobic frit and then evaporated to give the title compound (200 mg, pale yellow foam). $^1$H NMR (400 MHz, CDCl$_3$) δ ppm 1.21 (t, J=7.20 Hz, 3H) 3.69-3.80 (m, 1H) 3.83-3.94 (m, 2H) 4.29 (dd, J=8.08, 1.77 Hz, 1H) 4.41-4.50 (m, 2H) 4.67 (br. s., 2H) 7.25 (dd, J=10.61, 9.09 Hz, 1H) 8.23 (ddd, J=8.84, 4.04, 2.78 Hz, 1H) 8.32 (dd, J=6.69, 2.91 Hz, 1H).

Step 4: tert-Butyl ((4aS,5S,7aS)-3-ethyl-7a-(2-fluoro-5-nitrophenyl)-4-oxo-5-(trifluoromethyl)-3,4,4a,5,7,7a-hexahydrofuro[3,4-d]pyrimidin-2-yl)carbamate

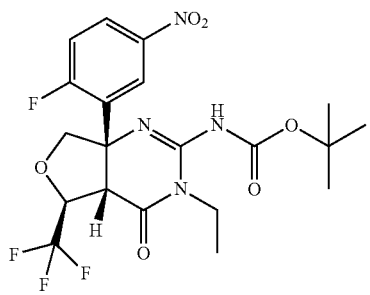 [SMILES: CCN1C(=O)[C@@H]2[C@@H](C(F)(F)F)OC[C@]2(c2cc([N+](=O)[O-])ccc2F)N=C1NC(=O)OC(C)(C)C]

N-Ethyl-N-(propan-2-yl)propan-2-amine (0.22 mL, 1.25 mmol) was added to a stirred solution of di-tert-butyl dicarbonate (140 mg, 0.62 mmol) and (4aS,5S,7aS)-2-amino-3-ethyl-7a-(2-fluoro-5-nitrophenyl)-5-(trifluoromethyl)-4a,5,7,7a-tetrahydrofuro[3,4-d]pyrimidin-4(3H)-one (195 mg, 0.50 mmol) in dry THF (2 mL) at RT under nitrogen. The pale yellow solution was stirred at this temperature overnight. The volatiles were removed in vacuo and the residue was purified by column chromatography (normal phase, 10 g, Biotage SNAP cartridge KP-Sil, 12 mL per min, gradient 5% to 30% EtOAc in n-hexane) to give the title compound. (226 mg, colourless foam). $^1$H NMR (400 MHz, CDCl$_3$) δ ppm 1.14 (t, J=7.07 Hz, 3H) 1.56 (s, 9H) 3.95-4.11 (m, 3H) 4.40-4.48 (m, 2H) 4.55-4.64 (m, 1H) 7.37 (dd, J=10.36, 9.09 Hz, 1H) 8.23 (dd, J=6.57, 2.78 Hz, 1H) 8.35 (ddd, J=8.97, 4.17, 2.78 Hz, 1H) 10.69 (s, 1H).

Step 5: tert-Butyl ((4aS,5S,7aS)-7a-(5-amino-2-fluorophenyl)-3-ethyl-4-oxo-5-(trifluoromethyl)-3,4,4a,5,7,7a-hexahydrofuro[3,4-d]pyrimidin-2-yl)carbamate

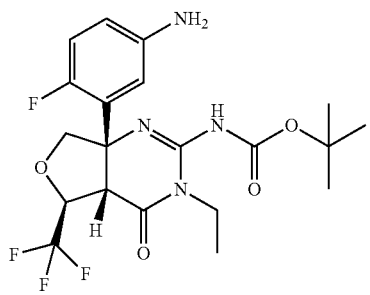 [SMILES: CCN1C(=O)[C@@H]2[C@@H](C(F)(F)F)OC[C@]2(c2cc(N)ccc2F)N=C1NC(=O)OC(C)(C)C]

A solution of tert-butyl ((4aS,5S,7aS)-3-ethyl-7a-(2-fluoro-5-nitrophenyl)-4-oxo-5-(trifluoromethyl)-3,4,4a,5,7,7a-hexahydrofuro[3,4-d]pyrimidin-2-yl)carbamate (0.225 g, 0.46 mmol) in ethanol (30 mL) was hydrogenated over 10% Pd/C (50 mg) at RT under a balloon of hydrogen for 2 h. The catalyst was removed by filtration through Celite-washing with ethanol. The filtrate was evaporated to give the title compound (0.21 g, colourless foam). $^1$H NMR (400 MHz, CDCl$_3$) δ ppm 1.14 (t, J=6.95 Hz, 3H) 1.53 (s, 9H) 3.90-4.12 (m, 3H) 4.31 (d, J=9.60 Hz, 1H) 4.45 (dd, J=9.60, 3.28 Hz, 1H) 4.47-4.56 (m, 1H) 6.46 (dd, J=6.32, 2.78 Hz, 1H) 6.63 (ddd, J=8.59, 3.79, 2.78 Hz, 1H) 6.94 (dd, J=11.12, 8.84 Hz, 1H) 10.49 (br. s., 1H).

Step 6: tert-Butyl ((4aS,5S,7aS)-7a-(5-(5-(difluoromethyl)pyrazine-2-carboxamido)-2-fluorophenyl)-3-ethyl-4-oxo-5-(trifluoromethyl)-3,4,4a,5,7,7a-hexahydrofuro[3,4-d]pyrimidin-2-yl)carbamate

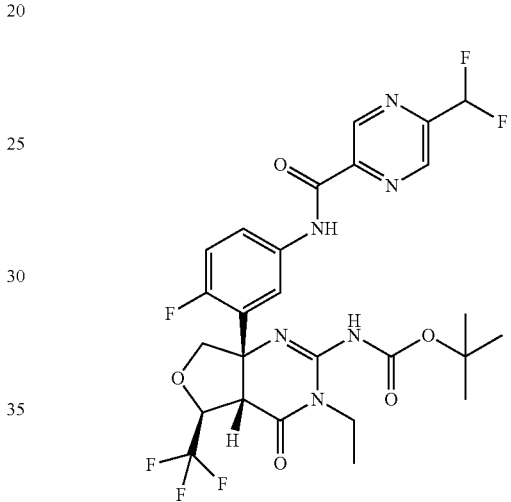

N-Ethyl-N-(propan-2-yl)propan-2-amine (190 μL, 1.1 mmol) was added to a stirred mixture of tert-butyl ((4aS,5S,7aS)-7a-(5-amino-2-fluorophenyl)-3-ethyl-4-oxo-5-(trifluoromethyl)-3,4,4a,5,7,7a-hexahydrofuro[3,4-d]pyrimidin-2-yl)carbamate (100 mg, 0.21 mmol), 5-(difluoromethyl)pyrazine-2-carboxylic acid (57 mg, 0.33 mmol) and (1H-benzotriazol-1-yloxy)(tripyrrolidin-1-yl)phosphonium hexafluorophosphate (170 mg, 0.33 mmol) in dry DCM (1 mL) at RT under nitrogen. The reaction was stirred at this temperature for 16 h, and then partitioned between DCM and NaHCO$_3$ (aq.). The aqueous layer was extracted with DCM (×2). The combined extracts were dried by passing through a hydrophobic frit and then evaporated. The residue was purified by column chromatography (normal phase, 10 g, Biotage SNAP cartridge KP-Sil, 12 mL per min, gradient 5% to 30% EtOAc in n-hexane) to give the title compound (118 mg, cream foam). $^1$H NMR (400 MHz, CDCl$_3$-d) δ ppm 1.14 (t, J=7.07 Hz, 3H) 1.56 (s, 9H) 3.96-4.15 (m, 3H) 4.39 (d, J=9.60 Hz, 1H) 4.50 (dd, J=9.73, 2.91 Hz, 1H) 4.53-4.62 (m, 1H) 6.81 (t, J=54.60 Hz, 1H) 7.22 (dd, J=10.74, 8.97 Hz, 1H) 7.76 (dd, J=6.69, 2.65 Hz, 1H) 7.79-7.84 (m, 1H) 8.93 (s, 1H) 9.52 (s, 1H) 9.65 (s, 1H) 10.64 (s, 1H).

Step 7: N-(3-((4aS,5S,7aS)-2-Amino-3-ethyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide

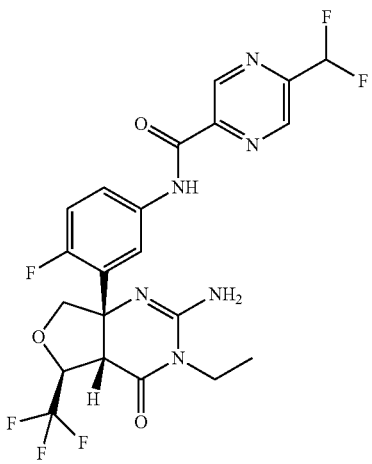 [SMILES: CCN1C(=O)[C@@H]2[C@@H](C(F)(F)F)OC[C@]2(c2cc(NC(=O)c3cnc(C(F)F)cn3)ccc2F)N=C1N]

Trifluoroacetic acid (1 mL) was added to a stirred solution of tert-butyl ((4aS,5S,7aS)-7a-(5-(5-(difluoromethyl)pyrazine-2-carboxamido)-2-fluorophenyl)-3-ethyl-4-oxo-5-(trifluoromethyl)-3,4,4a,5,7,7a-hexahydrofuro[3,4-d]pyrimidin-2-yl)carbamate (115 mg, 0.19 mmol) in DCM (1 mL) at RT. The volatiles were removed in vacuo and the residue was azeotroped with toluene (×1). The free base was isolated by loading this material on to a SCX cartridge (5 g) and eluting with MeOH (2×20 mL) and then 2M $NH_3$ in MeOH (1×20 mL). The ammonia-methanol fraction was evaporated and the residue was treated with $Et_2O$-hexanes to give a solid which was isolated by filtration and dried in vacuo to give the title compound (85 mg, cream solid). $^1$H NMR (400 MHz, MeOH-d4) δ ppm 1.12 (t, J=7.07 Hz, 3H) 3.65-3.81 (m, 2H) 3.94-4.03 (m, 1H) 4.29-4.35 (m, 1H) 4.36-4.41 (m, 1H) 4.56-4.66 (m, 1H) 6.95 (t, J=55.30 Hz, 1H) 7.19 (dd, J=11.49, 8.97 Hz, 1H) 7.74-7.81 (m, 1H) 7.97 (dd, J=6.95, 2.40 Hz, 1H) 9.02 (s, 1H) 9.40 (s, 1H).

EXAMPLE 13

N-(3-((4aS,5R,7aS)-2-Amino-3-ethyl-5-methyl-4-oxo-3,4,4a,5,7,7a-hexahydrofuro[3,4-d]pyrimidin-7a-yl)-4-fluorophenyl)-5-(difluoromethyl)pyrazine-2

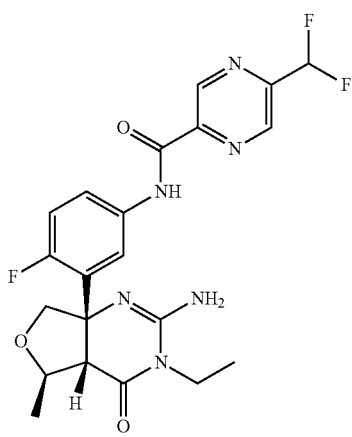 [SMILES: CCN1C(=O)[C@@H]2[C@@H](C)OC[C@]2(c2cc(NC(=O)c3cnc(C(F)F)cn3)ccc2F)N=C1N]

This material was prepared by analogy with the procedures used to prepare example 12, starting from (2R,3S,4S)-methyl 4-amino-4-(2-fluorophenyl)-2-methyltetrahydrofuran-3-carboxylate (Example 2, Step 2). $^1$H NMR (400 MHz, MeOH-d4) δ ppm 1.11 (t, J=7.07 Hz, 3H) 1.42 (d, J=6.06 Hz, 3H) 3.19 (d, J=9.09 Hz, 1H) 3.69-3.82 (m, 1H) 3.86-4.00 (m, 1H) 4.20-4.30 (m, 2H) 4.32-4.38 (m, 1H) 6.95 (t, J=54.60 Hz, 1H) 7.16 (dd, J=11.49, 8.97 Hz, 1H) 7.74 (ddd, J=8.78, 4.23, 2.65 Hz, 1H) 7.89 (dd, J=7.07, 2.53 Hz, 1H) 9.02 (s, 1H) 9.40 (s, 1H)

TEST EXAMPLE 1

Quantification of Aβ Peptide in Culture of Neurons from Rat Fetus Brain
(1) Rat Primary Neuronal Culture
Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (such as Invitrogen Corp. Cat #11415-064, Carlsbad, Calif., USA, or SIGMA L1518). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 mL of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) were used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μL/well at an initial cell density of 5×10$^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/mL of a poly-L-lysine (SIGMA P2636, St. Louis, Mo., USA) solution was aseptically prepared with a 0.15 M borate buffer (pH 8.5). 100 μg/well of the solution was added to the 96-well polystyrene culture plate and incubated at room temperature for one or more hours or at 4° C. overnight or longer. Thereafter, the coated 96-well polystyrene culture plate was washed with sterile water four or more times, and then dried or rinsed with, for example, sterile PBS or medium, and used for cell plating. The plated cells were cultured in the culture plate at 37° C. in 5% $CO_2$-95% air for one day. Then, the total amount of the medium was replaced with a fresh Neurobasal™/B27/2-ME medium, and then the cells were cultured for a further three days.

(2) Addition of Compound

The drug was added to the culture plate on Day 4 of culture as follows. The total amount of the medium was removed from the wells, and 180 μL/well of Neurobasal medium not containing 2-ME and containing 2% B-27 (Neurobasal/B27) was added thereto. A solution of the test compound in DMSO was diluted with Neurobasal/B27 to a concentration 10-fold higher than the final concentration. 20 μL/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μL/well of a pre-warmed medium was added to the wells. Further, 8 μL/well of a solution of 8 mg/mL of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μL/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate, sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μL each of concentrated hydrochloric acid and acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of $CTRL = (A550\_sample - A550\_bkg)/(A550\_CTRL - bkg) \times 100$ (A550_sample: absorbance at 550 nm of sample well, A550_bkg: absorbance at 550 nm of background well, A550_CTRL: absorbance at 550 nm of control group well)

(5) Aβ ELISA

Human/Rat β Amyloid (42) ELISA Kit Wako (#290-62601) and Human/Rat β Amyloid (40) ELISA Kit Wako (#294-62501) from Wako Pure Chemical Industries, Ltd. were used for Aβ ELISA. Aβ ELISA was carried out according to the protocols recommended by the manufacturers, described in the documents accompanying the kits. However, the Aβ calibration curve was created using beta-amyloid peptide 1-42, rat and beta-amyloid peptide 1-40, rat (Calbiochem, #171596 [Aβ$_{42}$], #171593 [Aβ$_{40}$]). The results would be shown as percentage to the Aβ concentration in the medium of the control group (% of CTRL).

The compounds of the present invention have an Aβ42 production reducing effect.

The compound of the general formula (I) or pharmaceutically acceptable salt thereof or solvate thereof according to the present invention has an Aβ42 production reducing effect. Thus, the present invention can particularly provide a prophylactic or therapeutic agent for a neurodegenerative disease caused by Aβ such as Alzheimer-type dementia or Down's syndrome.

As measured by Test Example 1, compound Examples 1 to 13 showed $IC_{50}$ values of less than 1 μM.

The invention claimed is:

1. A compound represented by the formula (I):

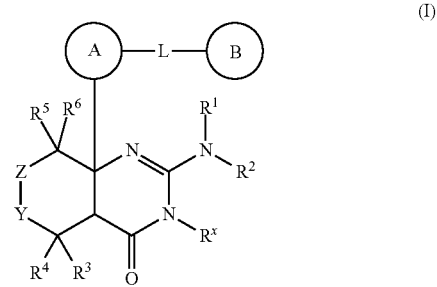

(I)

or a pharmaceutically acceptable salt thereof or a solvate thereof, wherein

Ring A is a $C_{6-14}$ aryl group which optionally has 1 to 3 substituents selected from Substituent Group α, a 5- to 6-membered heteroaryl group which optionally has 1 to 3 substituents selected from Substituent Group α or a 9- to 10-membered benzo-fused heterocyclic group which optionally has 1 to 3 substituents selected from Substituent Group α;

L is —NR$^e$CO— (wherein R$^e$ is a hydrogen atom or a $C_{1-6}$ alkyl group);

Ring B is a $C_{3-8}$ cycloalkyl group which optionally has 1 to 3 substituents selected from Substituent Group α, a $C_{6-14}$ aryl group which optionally has 1 to 3 substituents selected from Substituent Group α or a 5- to 10-membered heterocyclic group which optionally has 1 to 3 substituents selected from Substituent Group α;

Y is an oxygen atom;

Z is a single bond;

$R^1$ and $R^2$ are each independently a hydrogen atom, a $C_{1-6}$ alkyl group; which optionally has 1 to 3 substituents selected from Substituent Group α, a $C_{1-6}$ alkylcarbonyl group which optionally has 1 to 3 substituents selected from Substituent Group α, a $C_{6-14}$ arylcarbonyl group which optionally has 1 to 3 substituents selected from Substituent Group α, a $C_{1-6}$ alkylsulfonyl group which optionally has 1 to 3 substituents selected from Substituent Group α, a $C_{6-14}$ arylsulfonyl group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; and $R^3$, $R^4$, $R^5$ and $R^6$ are independently a hydrogen atom, a halogen atom, a hydroxy group, a C1-6 alkyl group which optionally has 1 to 3 substituents selected from Substituent Group α, a $C_{1-6}$ alkoxy group which optionally has 1 to 3 substituents selected from Substituent Group α, a 3- to 10-membered carbocyclic group which optionally has 1 to 3 substituents selected from Substituent Group α or a 5- to 10-membered heterocyclic group which optionally has 1 to 3 substituents selected from Substituent Group α; or $R^4$ and $R^6$ together form a ring represented by the formula (II):

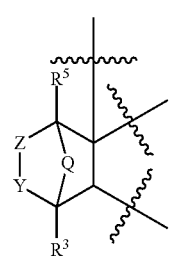

(II)

wherein Y, Z, $R^5$ and $R^3$ are the same as defined above and Q is an oxygen atom, a methylene group or an ethylene group;

$R^X$ is a hydrogen atom, a $C_{1-6}$ alkyl group; which optionally has 1 to 3 substituents selected from Substituent Group α, a $C_{3-8}$ cycloalkyl group which optionally has 1 to 3 substituents selected from Substituent Group α, a $C_{6-14}$ aryl group which optionally has 1 to 3 substituents selected from Substituent Group α, a 5- to 10-membered heterocyclic group which optionally has 1 to 3 substituents selected from Substituent Group α, a $C_{3-8}$ cycloalkyl-$C_{1-6}$ alkyl group which optionally has 1 to 3 substituents selected from Substituent Group α, a $C_{6-14}$ aryl-$C_{1-6}$ alkyl group which optionally has 1 to 3 substituents selected from Substituent Group α, a 5- to 10-membered heterocyclic-$C_{1-6}$ alkyl group which optionally has 1 to 3 substituents selected from Substituent Group α, wherein Substituent Group α consists of a hydrogen atom, a halogen atom, a hydroxy group, a nitro group, a $C_{1-6}$ alkylthio group, a $C_{6-14}$ aryl group, a $C_{6-14}$ aryloxycarbonyl group, a $C_{6-14}$ arylcarbonyl group, a cyano group, a $C_{3-8}$ cycloalkoxy group, a $C_{3-8}$ cycloalkyl group, a $C_{3-8}$ cycloalkylthio group, a sulfonylamino group (wherein the sulfonylamino group is optionally substituted with a $C_{1-6}$ alkyl group), a $C_{2-6}$ alkenyl group which optionally has 1 to 3 substituents selected from Substituent Group β, a $C_{2-6}$ alkynyl group which optionally has 1 to 3 substituents selected from Substituent Group β, a carbamoyl group which is optionally substituted with one or two $C_{1-6}$ alkyl groups, a $C_{1-6}$ alkoxy group which optionally has 1 to 3 substituents selected from Substituent Group β, a $C_{1-6}$ alkyl group which optionally has 1 to 3 substituents selected from Substituent Group β and a 5- to 10-membered heterocyclic group which optionally has 1 to 3 substituents selected from Substituent Group β; and wherein Substituent Group β consists of a halogen atom, a cyano group, a hydroxy group, a $C_{1-6}$ alkoxy group, a $C_{1-6}$ alkyl group, a $C_{3-8}$ cycloalkyl group and an oxo group.

2. The compound or pharmaceutically acceptable salt thereof or solvate thereof according to claim 1 wherein L is —NHCO—.

3. The compound or pharmaceutically acceptable salt thereof or solvate thereof according to claim 1 wherein Ring A is a $C_{6-14}$ aryl group which optionally has 1 to 3 substituents selected from Substituent Group α.

4. The compound or pharmaceutically acceptable salt thereof or solvate thereof according to claim 1 wherein Ring B is a 5 to 10-membered heterocyclic group which optionally has 1 to 3 substituents selected from Substituent Group α.

5. The compound or pharmaceutically acceptable salt thereof or solvate thereof according to claim 1 wherein the compound is selected from:

N-(3-(2-amino-3-methyl-4-oxo-3,4,4a,5,7,7a-hexahydrofuro [3,4-d]pyrimidin-7a-yl)-4-fluorophenyl)-5-(difluoromethyl)pyrazine-2-carboxamide;

N-(3-(2-amino-3-methyl-4-oxo-3,4,4a,5,7,7a-hexahydrofuro [3,4-d]pyrimidin-7a-yl)-4-fluorophenyl)-5-methoxypyrazine-2-carboxamide;

N-(3-(2-amino-3-methyl-4-oxo-3,4,4a,5,7,7a-hexahydrofuro [3,4-d]pyrimidin-7a-yl)-4-fluorophenyl)-5-(difluoromethoxy)pyrazine-2-carboxamide;

N-(3-(2-amino-3-methyl-4-oxo-3,4,4a,5,7,7a-hexahydrofuro [3,4-d]pyrimidin-7a-yl)-4-fluorophenyl)-5-(fluoromethoxy)pyrazine-2-carboxamide;

N-(3-(2-amino-3-methyl-4-oxo-3,4,4a,5,7,7a-hexahydrofuro [3,4-d]pyrimidin-7a-yl)-4-fluorophenyl)-5-ethoxypyrazine-2-carboxamide;

N-(3-(2-amino-3-methyl-4-oxo-3,4,4a,5,7,7a-hexahydrofuro [3,4-d]pyrimidin-7a-yl)-4-fluorophenyl)-5-fluoropicolinamide;

N-(3-(2-amino-3-methyl-4-oxo-3,4,4a,5,7,7a-hexahydrofuro [3,4-d]pyrimidin-7a-yl)-4-fluorophenyl)-5-cyanopicolinamide;

N-(3-(2-amino-3-methyl-4-oxo-3,4,4a,5,7,7a-hexahydrofuro [3,4-d]pyrimidin-7a-yl)-4-fluorophenyl)-5-chloropicolinamide;

N-(3-(2-amino-3-methyl-4-oxo-3,4,4a,5,7,7a-hexahydrofuro [3,4-d]pyrimidin-7a-yl)-4-fluorophenyl)-5-(trifluoromethyl)picolinamide;

N-(3-(2-amino-3-methyl-4-oxo-3,4,4a,5,7,7a-hexahydrofuro [3,4-d]pyrimidin-7a-yl)-4-fluorophenyl)-5-(difluoromethyl)picolinamide;

N-(3-(2-amino-3-methyl-4-oxo-3,4,4a,5,7,7a-hexahydrofuro [3,4-d]pyrimidin-7a-yl)-4-fluorophenyl)-5-(fluoromethyl)picolinamide;

N-(3-(2-amino-3-methyl-4-oxo-3,4,4a,5,7,7a-hexahydrofuro [3,4-d]pyrimidin-7a-yl)-4-fluorophenyl)-5-methoxypicolinamide;

N-(3-(2-amino-3-methyl-4-oxo-3,4,4a,5,7,7a-hexahydrofuro [3,4-d]pyrimidin-7a-yl)-4-fluorophenyl)-5-(difluoromethoxy)picolinamide;

N-(3-((4aS,5R,7aS)-2-Amino-3,5-dimethyl-4-oxo-3,4,4a, 5,7,7a-hexahydrofuro[3,4-d]pyrimidin-7a-yl)-4-fluorophenyl)-5-(difluoromethyl)pyrazine-2-carboxamide;

N-(3-((4aS,5R,7aS)-2-Amino-3,5-dimethyl-4-oxo-3,4,4a, 5,7,7a-hexahydrofuro[3,4-d]pyrimidin-7a-yl)-4-fluorophenyl)-5-methoxypyrazine-2-carboxamide;

N-(3-((4aS,5R,7aS)-2-amino-3,5-dimethyl-4-oxo-3,4,4a, 5,7,7a-hexahydrofuro[3,4-d]pyrimidin-7a-yl)-4-fluorophenyl)-5-methylpyrazine-2-carboxamide;

N-(3-((4aS,5R,7aS)-2-Amino-3,5-dimethyl-4-oxo-3,4,4a, 5,7,7a-hexahydrofuro[3,4-d]pyrimidin-7a-yl)-4-fluorophenyl)-5-methylpicolinamide;

N-(3-((4aS,5R,7aS)-2-amino-3,5-dimethyl-4-oxo-3,4,4a, 5,7,7a-hexahydrofuro[3,4-d]pyrimidin-7a-yl)-4-fluorophenyl)-5-(trifluoromethyl)picolinamide;

N-(3-((4aS,5R,7aS)-2-amino-3,5-dimethyl-4-oxo-3,4,4a, 5,7,7a-hexahydrofuro[3,4-d]pyrimidin-7a-yl)-4-fluorophenyl)-5-cyanopicolinamide;

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide;

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methoxypyrazine-2-carboxamide;

N-(3-((4aS,5S,7aS)-2-amino-3-methyl-4-oxo-5-(trifluoromethyl)-3,4,4a,5,7,7a-hexahydrofuro[3,4-d]pyrimidin-7a-yl)-4-fluorophenyl)-5-methylpicolinamide;

N-(3-((4aS,5S,7aS)-2-Amino-3-methyl-4-oxo-5-(trifluoromethyl)-3,4,4a,5,7,7a-hexahydrofuro[3,4-d]pyrimidin-7a-yl)-4-fluorophenyl)-5-cyanopicolinamide;

N-(3-((4aS,5S,7aS)-2-Amino-3-ethyl-4-oxo-5-(trifluoromethyl)-3,4,4a,5,7,7a-hexahydrofuro[3,4-d]pyrimidin-7a-yl)-4-fluorophenyl)-5-(difluoromethyl)pyrazine-2-carboxamide; and N-(3-((4aS,5R,7aS)-2-Amino-3-ethyl-5-methyl-4-oxo-3,4,4a,5,7,7a-hexahydrofuro[3,4-d]pyrimidin-7a-yl)-4-fluorophenyl)-5-(difluoromethyl)pyrazine-2-carboxamide.

6. The compound or pharmaceutically acceptable salt thereof or solvate thereof according to claim 1 wherein the compound has the following stereochemistry:

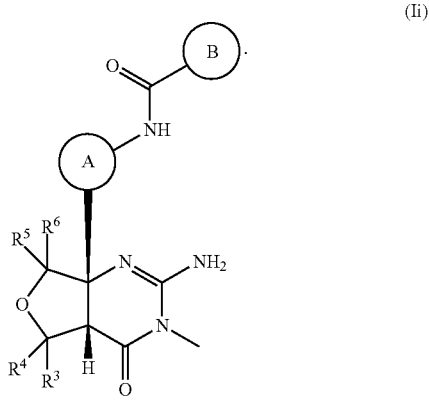

(Ii)

7. A pharmaceutical composition comprising the compound or pharmaceutically acceptable salt thereof or solvate thereof according to claim 1 as an active ingredient.

8. A method of inhibiting production of amyloid-βprotein, comprising administering to a human subject an effective amount of the pharmaceutical composition according to claim 7.

9. A method of inhibiting beta-site amyloid-βprecursor protein cleaving enzyme 1 (BACE1), comprising administering to a human subject an effective amount of the pharmaceutical composition according to claim 7.

10. A method of treating Alzheimer's-type dementia, comprising administering to a human subject suffering from Alzheimer's-type dementia an effective amount of the pharmaceutical composition according to claim 7.

11. A pharmaceutical composition comprising the compound or pharmaceutically acceptable salt thereof or solvate thereof according to claim 5 as an active ingredient.

12. A method of treating Alzheimer's-type dementia, comprising administering to a human subject suffering from Alzheimer's-type dementia an effective amount of the pharmaceutical composition according to claim 11.

* * * * *

UNITED STATES PATENT AND TRADEMARK OFFICE
CERTIFICATE OF CORRECTION

PATENT NO. : 9,139,594 B2
APPLICATION NO. : 13/386199
DATED : September 22, 2015
INVENTOR(S) : Jose Luis Castro Pineiro et al.

It is certified that error appears in the above-identified patent and that said Letters Patent is hereby corrected as shown below:

In the Claims

Column 102, Claim 1

Line 33, delete "$R^e$is" and insert -- $R^e$ is --.

Line 59, delete "C1-6" and insert -- $C_{1-6}$ --.

Column 103, Claim 1

Line 47, delete "βand" and insert -- β and --.

Column 106, Claim 8

Line 5, delete "βprotein," and insert -- β protein, --.

Column 106, Claim 9

Line 11, delete "βprecursor" and insert -- β precursor --.

Signed and Sealed this
Twenty-first Day of June, 2016

Michelle K. Lee
*Director of the United States Patent and Trademark Office*